(12) United States Patent
Arasappan et al.

(10) Patent No.: US 10,934,294 B2
(45) Date of Patent: *Mar. 2, 2021

(54) SUBSTITUTED PYRAZOLO[3,4-D]PYRIMIDINES AS PDE9 INHIBITORS

(71) Applicant: Merck Sharp & Dohme Corp., Rahway, NJ (US)

(72) Inventors: Ashok Arasappan, Bridgewater, NJ (US); Jason M. Cox, Whitehouse Station, NJ (US); John S. Debenham, Scotch Plains, NJ (US); Zhuyan Guo, Scotch Plains, NJ (US); Jiafang He, Dayton, NJ (US); Zahid Hussain, Dayton, NJ (US); Zhong Lai, East Brunswick, NJ (US); Derun Li, Scotch Plains, NJ (US); Dongfang Meng, Morganville, NJ (US); Subharekha Raghavan, Teaneck, NJ (US); Sriram Tyagarajan, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/001,295

(22) Filed: Jun. 6, 2018

(65) Prior Publication Data
US 2018/0354955 A1 Dec. 13, 2018

Related U.S. Application Data

(60) Provisional application No. 62/516,903, filed on Jun. 8, 2017, provisional application No. 62/665,840, filed on May 2, 2018.

(51) Int. Cl.
A61K 31/519 (2006.01)
C07D 487/04 (2006.01)
A61P 9/00 (2006.01)
A61P 25/00 (2006.01)
A61P 13/12 (2006.01)
A61P 25/18 (2006.01)

(52) U.S. Cl.
CPC .............. C07D 487/04 (2013.01); A61P 9/00 (2018.01); A61P 13/12 (2018.01); A61P 25/00 (2018.01); A61P 25/18 (2018.01)

(58) Field of Classification Search
CPC ............................ A61K 31/519; C07D 487/04
USPC .......................................... 514/22.1; 544/262
See application file for complete search history.

(56) References Cited

U.S. PATENT DOCUMENTS 5,294,612 A 3/1994 Bacon et al.
5,541,187 A 7/1996 Bacon
6,174,884 B1 1/2001 Haning et al.
6,552,192 B1 4/2003 Hanus et al.
6,770,645 B2 8/2004 Denton et al.
6,967,204 B2 11/2005 Fryburg
7,022,709 B2 4/2006 Boess
7,488,733 B2 2/2009 Hendrix
7,737,156 B2 6/2010 Boe
7,964,607 B2 6/2011 Verhoest
8,101,624 B2 1/2012 Asagarasu
8,168,639 B2 5/2012 Kogan
8,278,295 B2 10/2012 Claffey
8,299,080 B2 10/2012 Okada
8,377,944 B2 2/2013 Gotanda
8,618,117 B2 12/2013 Claffey
8,623,879 B2 1/2014 Giovannini
8,623,901 B2 1/2014 Giovannini
8,648,085 B2 2/2014 Eickmeier
(Continued)

FOREIGN PATENT DOCUMENTS

WO WO2012/020022 2/2012
WO WO2012/110440 8/2012
(Continued)

OTHER PUBLICATIONS

Jordan, V. C. Nature Reviews: Drug Discovery, Feb. 2003, 205.*
(Continued)

Primary Examiner — Douglas M Willis
(74) Attorney, Agent, or Firm — J. Eric Thies; John C. Todaro

(57) ABSTRACT

The present invention is directed to pyrazolopyrimidine compounds of the general structural formula I:

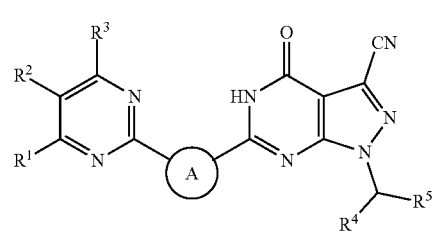

which may be useful as therapeutic agents for the treatment of disorders associated with phosphodiesterase 9 (PDE9). The present invention also relates to the use of such compounds for treating cardiovascular and cerebrovascular diseases, such as hypertension, chronic kidney disease and heart failure, and neurological and psychiatric disorders, such as schizophrenia, psychosis or Huntington's disease, and those associated with striatal hypofunction or basal ganglia dysfunction.

13 Claims, No Drawings

(56) References Cited

U.S. PATENT DOCUMENTS

| | | |
|---|---|---|
| 8,809,345 B2 | 8/2014 | Heine |
| 8,912,201 B2 | 12/2014 | Heine |
| 8,987,473 B2 | 3/2015 | Nagai |
| 9,079,905 B2 | 7/2015 | Fuchs |
| 9,089,572 B2 | 7/2015 | Brown |
| 9,096,603 B2 | 8/2015 | Giovannini |
| 9,102,679 B2 | 8/2015 | Giovannini |
| 9,174,992 B2 | 11/2015 | Allen |
| 9,338,437 B2 | 5/2016 | Bae |
| 9,643,970 B2 | 5/2017 | Svenstrup |
| 9,993,477 B2 | 6/2018 | Svenstrup |
| 10,160,762 B2 | 12/2018 | Shen |
| 10,174,032 B2 | 1/2019 | Morales |
| 10,287,293 B2 | 5/2019 | Stachel |
| 2003/0195205 A1 | 10/2003 | Deninno |
| 2011/0212960 A1 | 9/2011 | Heine |
| 2018/0162874 A1 | 6/2018 | Morriello |
| 2018/0208557 A1 | 7/2018 | Cofre |
| 2018/0214439 A1 | 8/2018 | Converso |
| 2018/0258046 A1 | 9/2018 | Converso |

FOREIGN PATENT DOCUMENTS

| | | |
|---|---|---|
| WO | WO2014024125 | 2/2014 |
| WO | WO 18/226771 | * 12/2018 |

OTHER PUBLICATIONS

Hackam, et al. JAMA, 296(14), 2006, 1731-1732.*
International Search Report and Written Opinion for PCT/US2018/036172 dated Sep. 21, 2018; 8 pages.

* cited by examiner

SUBSTITUTED PYRAZOLO[3,4-D]PYRIMIDINES AS PDE9 INHIBITORS

CROSS REFERENCE TO RELATED APPLICATIONS

This application claims priority under 35 U.S.C. § 119(e) from U.S. Ser. No. 62/516,903, filed Jun. 8, 2017, and claims priority under 35 U.S.C. § 119(e) from U.S. Ser. No. 62/665,840, filed May 2, 2018.

BACKGROUND OF THE INVENTION

The phosphodiesterases enzyme family hydrolyzes the cyclic nucleotides cyclic adenosine monophosphate (cAMP) and cyclic guanosine monophosphate (cGMP). cGMP and cAMP are central to the control and regulation of a multitude of cellular events, both physiological and pathophysiological. One pathway for affecting the levels of cyclic nucleotides, such as cAMP and cGMP, is to alter or regulate the enzymes that degrade these enzymes, known as 3', 5'-cyclic nucleotide specific phosphodiesterases (PDEs). The PDE superfamily includes twenty one genes that encode for eleven families of PDEs. These families are further subdivided based on catalytic domain homology and substrate specificity and include the: (1) cAM112 P specific, PDE4A-D, 7A and 7B, and 8A and 8B; (2) cGMP specific, PDE 5A, 6A-C, and 9A; and (3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of the phosphodiesterase PDE9 has been reported and was distinguished from other PDEs on the basis of its amino acid sequence, functional properties, and tissue distribution. PDE9V is encoded by two genes (PDE9A and PDE9B) and is cGMP specific. At least 20 different splice variants have been discovered (PDE9A1-PD9A20) in human and in mouse. Structural study of PDE9A have been shown that its cDNA of the different splice variants share a high percentage of amino acid identity in the catalytic domain. However, despite its highest specificity for cGMP among all the PDEs, PDE9A lacks a GAF domain, whose binding of cGMP usually activates catalytic activity. Besides its expression in the kidney, spleen, and other peripheral organs, PDE9 is widespread through the brain in mice, rats and humans, and has been found to be present in a variety of human tissues, including the testes, small intestine, skeletal muscle, smooth muscle in the vasculature, heart, lung, and thymus.

Inhibition of PDE9 is believed to be useful in the treatment of cardiovascular and cerebrovascular diseases, such as hypertension and heart failure, and cognitive deficit associated with neurodegenerative and psychiatric disorders and a variety of conditions or disorders that would benefit from increasing levels of cGMP within neurons, including including Alzheimer's disease, schizophrenia, and depression.

SUMMARY OF THE INVENTION

The present invention is directed to pyrazolopyrimidine compounds which may be useful as therapeutic agents for the treatment of disorders associated with phosphodiesterase 9 (PDE9). The present invention also relates to the use of such compounds for treating cardiovascular and cerebrovascular diseases, such as hypertension and heart failure, and neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

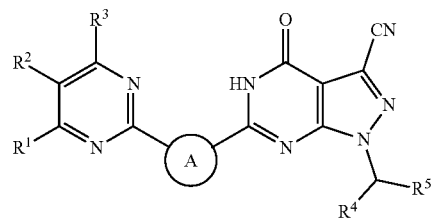

wherein:

A is a cyclobutyl ring, which is unsubstituted or or substituted with substituents selected from: fluoro and methyl;

$R^1$, $R^2$ and $R^3$ are independently selected from:
(1) hydrogen,
(2) halogen,
(3) hydroxyl,
(4) $C_{1-6}$alkyl, which is unsubstituted or substituted with substituents selected from: hydroxy and fluoro,
(5) —O—$C_{1-6}$alkyl, which is unsubstituted or substituted with substituents selected from fluoro,
(6) $C_{3-6}$cycloalkyl,
(7) $C_{2-6}$alkynyl, and
(8) —CN;

$R^4$ is selected from:
(1) hydrogen,
(2) —$CH_3$,
(3) —$CF_3$,
(4) —$CH_2OH$,
(5) —$CO_2H$, and
(6) —$CH_2CH_3$;

$R^5$ is a phenyl, pyridyl, pyrazinyl, pyrazolyl, pyrimidinyl, pyridazinyl, thiazolyl, cyclohexyl or tetrahydropyranyl ring, wherein the phenyl, pyridyl, pyrazinyl, pyrazolyl, pyrimidinyl, pyridazinyl, thiazolyl, cyclohexyl or tetrahydropyranyl ring is substituted with $R^{1a}$, $R^{1b}$ and $R^{1c}$, wherein $R^{1a}$, $R^{1b}$ and $R^{1c}$ are independently selected from:
(1) hydrogen,
(2) halogen,
(3) hydroxyl,
(4) $C_{1-6}$alkyl, which is unsubstituted or substituted with substituents selected from: hydroxy and fluoro,
(5) —O—$C_{1-6}$alkyl, which is unsubstituted or substituted with substituents selected from fluoro,
(6) $C_{3-6}$cycloalkyl, and
(7) —CN;

or a pharmaceutically acceptable salt thereof.

An embodiment of the present invention includes compounds of the formula Ia:

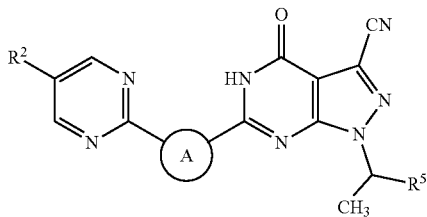

Ia wherein A, $R^2$ and $R^5$ are defined herein; or a pharmaceutically acceptable salt thereof.

An embodiment of the present invention includes compounds of the formula Iaa:

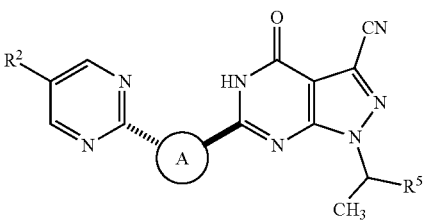

Iaa wherein A, $R^2$ and $R^5$ are defined herein; or a pharmaceutically acceptable salt thereof.

An embodiment of the present invention includes compounds of the formula Iaa':

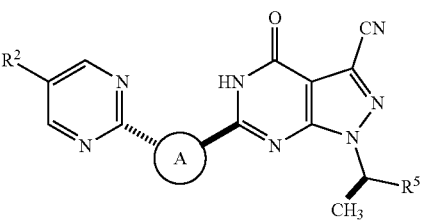

Iaa' wherein A, $R^2$ and $R^5$ are defined herein; or a pharmaceutically acceptable salt thereof.

An embodiment of the present invention includes compounds of the formula Iaa":

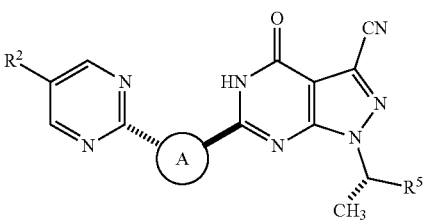

Iaa"

wherein A, $R^2$ and $R^5$ are defined herein; or a pharmaceutically acceptable salt thereof.

An embodiment of the present invention includes compounds of the formula Iab:

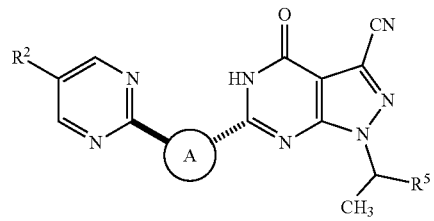

Iab wherein A, $R^2$ and $R^5$ are defined herein; or a pharmaceutically acceptable salt thereof.

An embodiment of the present invention includes compounds of the formula Iab':

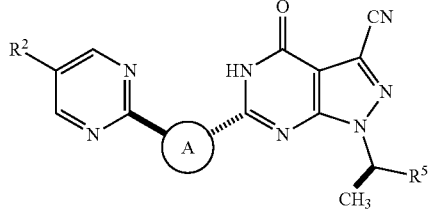

Iab' wherein A, $R^2$ and $R^5$ are defined herein; or a pharmaceutically acceptable salt thereof.

An embodiment of the present invention includes compounds of the formula Iab":

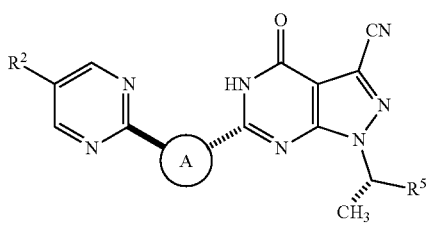

Iab"

wherein A, $R^2$ and $R^5$ are defined herein; or a pharmaceutically acceptable salt thereof.

An embodiment of the present invention includes compounds of the formula Ib:

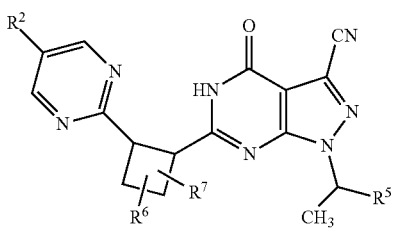

Ib wherein $R^2$, $R^5$, $R^6$ and $R^7$ are defined herein; or a pharmaceutically acceptable salt thereof.

An embodiment of the present invention includes compounds wherein A is a cyclobutyl ring, which is unsubstituted or substituted with $R^6$ and $R^7$, wherein $R^6$ and $R^7$ are selected from:

(1) hydrogen,
(2) fluoro, and
(3) —CH$_3$.

An embodiment of the present invention includes compounds wherein A is a cyclobutyl ring, which is unsubstituted or substituted with one or more fluoro.

An embodiment of the present invention includes compounds wherein R$^1$, R$^2$ and R$^3$ are independently selected from:
(1) hydrogen,
(2) halogen,
(3) hydroxyl,
(4) C$_{1-6}$alkyl, which is unsubstituted or substituted with substituents selected from: hydroxy and fluoro,
(5) —O—C$_{1-6}$alkyl, which is unsubstituted or substituted with substituents selected from fluoro,
(6) C$_{3-6}$cycloalkyl,
(7) C$_{2-4}$alkynyl, and
(8) —CN.

An embodiment of the present invention includes compounds wherein R$^1$, R$^2$ and R$^3$ are independently selected from:
(1) hydrogen,
(2) fluoro,
(3) chloro,
(4) hydroxyl,
(5) C$_{1-2}$alkyl, which is unsubstituted or substituted with one or more fluoro,
(6) —O—C$_{1-2}$alkyl, which is unsubstituted or substituted with one or more fluoro,
(7) C$_{3-5}$cycloalkyl, and
(8) C$_{2-3}$alkynyl.

An embodiment of the present invention includes compounds wherein R$^1$ is hydrogen and R$^3$ is hydrogen.

An embodiment of the present invention includes compounds wherein R$^1$ is hydrogen, R$^3$ is hydrogen and R$^2$ is selected from:
(1) hydrogen,
(2) fluoro,
(3) chloro,
(4) hydroxyl,
(5) C$_{1-2}$alkyl, which is unsubstituted or substituted with one or more fluoro,
(6) —O—C$_{1-2}$alkyl, which is unsubstituted or substituted with one or more fluoro, and
(7) C$_{3-5}$cycloalkyl, and
(8) C$_{2-3}$alkynyl.

An embodiment of the present invention includes compounds wherein R$^1$ is hydrogen, R$^3$ is hydrogen and R$^2$ is selected from:
(1) hydrogen,
(2) fluoro,
(3) chloro,
(4) bromo,
(5) hydroxyl,
(6) —CH$_3$,
(7) —OCH$_3$,
(8) —CHF$_2$,
(9) —CF$_3$,
(10) —OCHF$_2$,
(11) —OCF$_3$,
(12) —CH$_2$CH$_3$,
(13) —CH(CH$_3$)$_2$,
(14) —C(CH$_3$)$_3$,
(15) —C≡CH, and
(16) cyclopropyl.

An embodiment of the present invention includes compounds wherein R$^4$ is hydrogen. An embodiment of the present invention includes compounds wherein R$^4$ is —CH$_3$.

An embodiment of the present invention includes compounds wherein R$^5$ is a phenyl, pyridyl, pyrazinyl, pyrazolyl, pyrimidinyl, pyridazinyl or thiazolyl ring, wherein the phenyl, pyridyl, pyrazinyl, pyrazolyl, pyrimidinyl, pyridazinyl or thiazolyl ring is substituted with R$^{1a}$, R$^{1b}$ and R$^{1c}$, wherein R$^{1a}$, R$^{1b}$ and R$^{1c}$ are independently selected from:
(1) hydrogen,
(2) halogen,
(3) hydroxyl,
(4) C$_{1-6}$alkyl, which is unsubstituted or substituted with substituents selected from: hydroxy and fluoro,
(5) —O—C$_{1-6}$alkyl, which is unsubstituted or substituted with substituents selected from fluoro,
(6) C$_{3-6}$cycloalkyl, and
(7) —CN.

An embodiment of the present invention includes compounds wherein R$^5$ is a phenyl, pyridyl, pyrazinyl, pyrazolyl, pyrimidinyl, pyridazinyl or thiazolyl ring, wherein the phenyl, pyridyl, pyrazinyl, pyrazolyl, pyrimidinyl, pyridazinyl or thiazolyl ring is substituted with R$^{1a}$, R$^{1b}$ and R$^{1c}$, wherein R$^{1a}$, R$^{1b}$ and R$^{1c}$ are independently selected from:
(1) hydrogen,
(2) fluoro,
(3) C$_{1-2}$alkyl, which is unsubstituted or substituted with one or more fluoro,
(4) —O—C$_{1-2}$alkyl, which is unsubstituted or substituted with one or more fluoro,
(5) cyclopropyl, and
(6) —CN.

An embodiment of the present invention includes compounds wherein R$^5$ is a phenyl, pyridyl, pyrazinyl, pyrazolyl, pyrimidinyl, pyridazinyl or thiazolyl ring, wherein the phenyl, pyridyl, pyrazinyl, pyrazolyl, pyrimidinyl, pyridazinyl or thiazolyl ring is substituted with R$^{1a}$, R$^{1b}$ and R$^{1c}$, wherein R$^{1a}$, R$^{1b}$ and R$^{1c}$ are independently selected from:
(1) hydrogen,
(2) fluoro,
(3) —CH$_3$,
(4) —CHF$_2$,
(5) —CF$_3$,
(6) —OCHF$_2$,
(7) —OCF$_3$,
(8) —OCHF$_2$,
(9) —OCF$_3$,
(10) cyclopropyl, and
(11) —CN.

An embodiment of the present invention includes compounds wherein R$^5$ is a phenyl ring. An embodiment of the present invention includes compounds wherein R$^5$ is a pyridyl ring. An embodiment of the present invention includes compounds wherein R$^5$ is a pyrazinyl ring. An embodiment of the present invention includes compounds wherein R$^5$ is a pyrazolyl ring. An embodiment of the present invention includes compounds wherein R$^5$ is a pyrimidinyl ring. An embodiment of the present invention includes compounds wherein R$^5$ is a pyridazinyl ring. An embodiment of the present invention includes compounds wherein R$^5$ is a thiazolyl ring. An embodiment of the present invention includes compounds wherein R$^5$ is a cyclohexyl ring. An embodiment of the present invention includes compounds wherein R$^5$ is a tetrahydropyranyl ring.

An embodiment of the present invention includes compounds R$^{1b}$ is hydrogen and R$^{1c}$ is hydrogen, and R$^{1a}$ is selected from:

(1) hydrogen,
(2) fluoro,
(3) —CH₃,
(4) —CHF₂,
(5) —CF₃,
(6) —OCHF₂,
(7) —OCF₃,
(8) cyclopropyl, and
(9) —CN.

An embodiment of the present invention includes compounds wherein $R^5$ is selected from:
(1) 4-fluorophenyl,
(2) 4-cyanophenyl,
(3) 3-(trifluoromethyl)phenyl,
(4) 4-(trifluoromethyl)phenyl,
(5) 3,4-difluorophenyl, and
(6) 6-(trifluoromethyl)pyridin-3-yl.

An embodiment of the present invention includes a compound which is selected from:

1-(1-(4-fluorophenyl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(4-fluorophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(4-fluorophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(4-fluorophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(4-fluorophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

4-oxo-6-(2-(pyrimidin-2-yl)cyclobutyl)-1-(1-(6-(trifluoromethyl)pyridin-3-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(6-(trifluoromethyl)pyridin-3-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(6-(trifluoromethyl)pyridin-3-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(6-(trifluoromethyl)pyridin-3-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(6-(trifluoromethyl)pyridin-3-yl)ethyl)-4,5-dihydro-1H-pyrazolo[3,4-d]pyrimidine-3-carbonitrile;

4-oxo-6-(2-(pyrimidin-2-yl)cyclobutyl)-1-((6-(trifluoromethyl)pyridin-3-yl)methyl)-4,5-dihydro-1H-pyrazolo[3,4-d]pyrimidine-3-carbonitrile;

4-oxo-6-((1R,2R)-2-(pyrimidin-2-yl)cyclobutyl)-1-((6-(trifluoromethyl)pyridin-3-yl)methyl)-4,5-dihydro-1H-pyrazolo[3,4-d]pyrimidine-3-carbonitrile;

4-oxo-6-((1S,2S)-2-(pyrimidin-2-yl)cyclobutyl)-1-((6-(trifluoromethyl)pyridin-3-yl)methyl)-4,5-dihydro-1H-pyrazolo[3,4-d]pyrimidine-3-carbonitrile;

1-[1-(4-cyanophenyl)ethyl]-4-oxo-6-(2-pyrimidin-2-ylcyclobutyl)-4,5-dihydro-1H-pyrazolo[3,4-d]pyrimidine-3-carbonitrile;

1-((S)-1-(4-cyanophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(4-cyanophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(4-cyanophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(4-cyanophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-(1-(3,4-difluorophenyl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(3,4-difluorophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(3,4-difluorophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(3,4-difluorophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(3,4-difluorophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

4-oxo-6-[2-pyrimidin-2-ylcyclobutyl]-1-{1-[4-(trifluoromethyl)phenyl]ethyl}-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(4-(trifluoromethyl)phenyl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(4-(trifluoromethyl)phenyl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(4-(trifluoromethyl)phenyl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(4-(trifluoromethyl)phenyl)ethyl)-4,5-dihydro-1H-pyrazolo[3,4-d]pyrimidine-3-carbonitrile;

4-oxo-6-[2-pyrimidin-2-ylcyclobutyl]-1-{1-[3-(trifluoromethyl)phenyl]ethyl}-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(3-(trifluoromethyl)phenyl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(3-(trifluoromethyl)phenyl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(3-(trifluoromethyl)phenyl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(3-(trifluoromethyl)phenyl)ethyl)-4,5-dihydro-1H-pyrazolo[3,4-d]pyrimidine-3-carbonitrile;

4-oxo-6-(2-(pyrimidin-2-yl)cyclobutyl)-1-(1-(5-(trifluoromethyl)pyrazin-2-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(5-(trifluoromethyl)pyrazin-2-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(5-(trifluoromethyl)pyrazin-2-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(5-(trifluoromethyl)pyrazin-2-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(5-(trifluoromethyl)pyrazin-2-yl)ethyl)-4,5-dihydro-1H-pyrazolo[3,4-d]pyrimidine-3-carbonitrile;

6-(2-(5-methylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-methylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-methylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

4-oxo-6-(2-(pyrimidin-2-yl)cyclobutyl)-1-(1-(2-(trifluoromethyl)pyrimidin-5-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(2-(trifluoromethyl)pyrimidin-5-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(2-(trifluoromethyl)pyrimidin-5-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(2-(trifluoromethyl)pyrimidin-5-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(2-(trifluoromethyl)pyrimidin-5-yl)ethyl)-4,5-dihydro-1H-pyrazolo[3,4-d]pyrimidine-3-carbonitrile;

1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(6-(difluoromethyl)pyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(6-(difluoromethyl)pyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(6-(difluoromethyl)pyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(6-(difluoromethyl)pyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((S)-1-(6-(difluoromethyl)pyridin-3-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((S)-1-(6-(difluoromethyl)pyridin-3-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

1-((R)-1-(6-(difluoromethyl)pyridin-3-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((R)-1-(6-(difluoromethyl)pyridin-3-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

4-oxo-6-(2-(pyrimidin-2-yl)cyclobutyl)-1-(1-(tetrahydro-2H-pyran-4-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(tetrahydro-2H-pyran-4-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(tetrahydro-2H-pyran-4-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(tetrahydro-2H-pyran-4-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(tetrahydro-2H-pyran-4-yl)ethyl)-4,5-dihydro-1H-pyrazolo[3,4-d]pyrimidine-3-carbonitrile;

1-(1-(6-cyclopropylpyridin-3-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(6-cyclopropylpyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(6-cyclopropylpyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(6-cyclopropylpyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(6-cyclopropylpyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((S)-1-(6-cyclopropylpyridin-3-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((S)-1-(6-cyclopropylpyridin-3-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

1-((R)-1-(6-cyclopropylpyridin-3-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((R)-1-(6-cyclopropylpyridin-3-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

6-(2-(5-bromopyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-bromopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-bromopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-bromopyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-bromopyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-(difluoromethoxy)pyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-(difluoromethoxy)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-(difluoromethoxy)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-(difluoromethoxy)pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-(difluoromethoxy)pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-ethylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-ethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-ethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-ethylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-ethylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

1-(1-(5-fluoropyridin-3-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(5-fluoropyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(5-fluoropyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(5-fluoropyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(5-fluoropyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-(1-(1-methyl-1H-pyrazol-4-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(1-methyl-1H-pyrazol-4-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(1-methyl-1H-pyrazol-4-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(1-methyl-1H-pyrazol-4-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(1-methyl-1H-pyrazol-4-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-(1-(6-cyclopropylpyridin-3-yl)ethyl)-6-(2-(5-fluoropyrimidin-2-yl)cyclobutyl)-4-oxo-4,5-dihydro-1H-pyrazolo[3,4-d]pyrimidine-3-carbonitrile;

1-((S)-1-(6-cyclopropylpyridin-3-yl)ethyl)-6-((1R,2R)-2-(5-fluoropyrimidin-2-yl)cyclobutyl)-4-oxo-4,5-dihydro-1H-pyrazolo[3,4-d]pyrimidine-3-carbonitrile;

1-((S)-1-(6-cyclopropylpyridin-3-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile;

1-((R)-1-(6-cyclopropylpyridin-3-yl)ethyl)-6-((1R,2R)-2-(5-fluoropyrimidin-2-yl)cyclobutyl)-4-oxo-4,5-dihydro-1H-pyrazolo[3,4-d]pyrimidine-3-carbonitrile;

1-((R)-1-(6-cyclopropylpyridin-3-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile;

4-oxo-6-(2-(pyrimidin-2-yl)cyclobutyl)-1-(1-(2-(trifluoromethyl)thiazol-5-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(2-(trifluoromethyl)thiazol-5-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(2-(trifluoromethyl)thiazol-5-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(2-(trifluoromethyl)thiazol-5-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(2-(trifluoromethyl)thiazol-5-yl)ethyl)-4,5-dihydro-1H-pyrazolo[3,4-d]pyrimidine-3-carbonitrile;

1-(1-(2-cyclopropylpyrimidin-5-yl)ethyl)-6-(2-(5-fluoropyrimidin-2-yl)cyclobutyl)-4-oxo-4,5-dihydro-1H-pyrazolo[3,4-d]pyrimidine-3-carbonitrile;

1-((S)-1-(2-cyclopropylpyrimidin-5-yl)ethyl)-6-((1R,2R)-2-(5-fluoropyrimidin-2-yl)cyclobutyl)-4-oxo-4,5-dihydro-1H-pyrazolo[3,4-d]pyrimidine-3-carbonitrile;

1-((S)-1-(2-cyclopropylpyrimidin-5-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile;

1-((R)-1-(2-cyclopropylpyrimidin-5-yl)ethyl)-6-((1R,2R)-2-(5-fluoropyrimidin-2-yl)cyclobutyl)-4-oxo-4,5-dihydro-1H-pyrazolo[3,4-d]pyrimidine-3-carbonitrile;

1-((R)-1-(2-cyclopropylpyrimidin-5-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile;

6-(2-(5-ethynylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-ethynylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-ethynylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-ethynylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-ethynylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-fluoropyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-fluoropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-fluoropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-fluoropyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-fluoropyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-fluoropyrimidin-2-yl)cyclobutyl)-4-oxo-1-(1-(tetrahydro-2H-pyran-4-yl)ethyl)-4,5-dihydro-1H-pyrazolo[3,4-d]pyrimidine-3-carbonitrile;

6-((1R,2R)-2-(5-fluoropyrimidin-2-yl)cyclobutyl)-4-oxo-1-((S)-1-(tetrahydro-2H-pyran-4-yl)ethyl)-4,5-dihydro-1H-pyrazolo[3,4-d]pyrimidine-3-carbonitrile;

6-((1S,2S)-2-(5-fluoropyrimidin-2-yl)cyclobutyl)-4-oxo-1-((S)-1-(tetrahydro-2H-pyran-4-yl)ethyl)-4,5-dihydro-1H-pyrazolo[3,4-d]pyrimidine-3-carbonitrile;

6-((1R,2R)-2-(5-fluoropyrimidin-2-yl)cyclobutyl)-4-oxo-1-((R)-1-(tetrahydro-2H-pyran-4-yl)ethyl)-4,5-dihydro-1H-pyrazolo[3,4-d]pyrimidine-3-carbonitrile;

6-((1S,2S)-2-(5-fluoropyrimidin-2-yl)cyclobutyl)-4-oxo-1-((R)-1-(tetrahydro-2H-pyran-4-yl)ethyl)-4,5-dihydro-1H-pyrazolo[3,4-d]pyrimidine-3-carbonitrile;

6-(1-methyl-2-(pyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-1-methyl-2-(pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-1-methyl-2-(pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-1-methyl-2-(pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-1-methyl-2-(pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-cyanopyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-cyanopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-cyanopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-cyanopyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-cyanopyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-cyclopropylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-cyclopropylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-cyclopropylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-cyclopropylpyrimidin-2-yl)cyclobutyl)-4-oxo-1-4R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-cyclopropylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(2-cyclopropylpyrimidin-5-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(2-cyclopropylpyrimidin-5-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(2-cyclopropylpyrimidin-5-yl)ethyl)-4-oxo-6-41R,2R)-2-(pyrimidin-2-yl)cyclobutyl)-4,5-dihydro-1H-pyrazolo[3,4-d]pyrimidine-3-carbonitrile;

1-((R)-1-(2-cyclopropylpyrimidin-5-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

6-(2-(5-methoxypyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-methoxypyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-methoxypyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-methoxypyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-methoxypyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

1-(1-(5-fluoropyridin-2-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(5-fluoropyridin-2-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(5-fluoropyridin-2-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((S)-1-(5-fluoropyridin-2-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((S)-1-(5-fluoropyridin-2-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

6-(2-(5-(difluoromethyl)pyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-(difluoromethyl)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-(difluoromethyl)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2S)-2-(5-(difluoromethyl)pyrimidin-2-yl)cyclobutyl)-4-oxo-1-4S)-1-(6-(trifluoromethyl)pyridin-3-yl)ethyl)-4,5-dihydro-1H-pyrazolo[3,4-d]pyrimidine-3-carbonitrile;

6-((1S,2R)-2-(5-(difluoromethyl)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-(2-(5-chloropyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-chloropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-chloropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-chloropyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-chloropyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(4-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(4,6-dimethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(4-(difluoromethyl)pyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;
6-((1S,2S)-2-(4,6-di-tert-butylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;
6-((1S,2S)-2-(4-cyclopropylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;
6-((1R,2R)-2-(4-(difluoromethyl)pyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile;
6-((1R,2R)-2-(4,6-bis(difluoromethyl)pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;
6-((1R,2R)-2-(4-methylpyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile;
6-((1R,2R)-2-(4,6-di-tert-butylpyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile;
6-((1R,2R)-2-(4-methylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;
6-((1R,2R)-2-(4,6-dimethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;
6-(2-(4-(tert-butyl)pyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;
6-((1R,2R)-2-(4,6-di-tert-butylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;
6-((1R,2R)-2-(4-(difluoromethyl)pyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile; and
6-((1R,2R)-2-(4-cyclopropylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;
or a pharmaceutically acceptable salt thereof.

Certain embodiments of the present invention include a compound which is selected from the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The compounds of the present invention may exist in different tautomeric forms, and all such forms are embraced within the scope of the invention. Also, for example, all keto-enol, lactam-lactim and amide-imidic acid forms of the compounds are included in the invention. Thus, for example, the compounds of the invention of the formula:

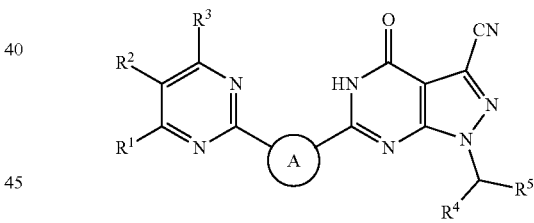

and their tautomers:

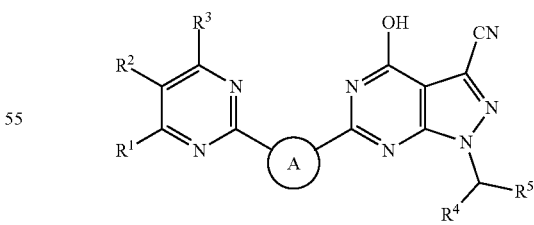

are both contemplated as being within the scope of the compounds of the invention, and the depiction of a particular tautomeric form embraces all other tautomeric forms.

As appreciated by those of skill in the art, halogen or halo as used herein are intended to include fluoro, chloro, bromo and iodo. The term $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Substituents (such as $R^1$, $R^2$, $R^3$, $R^{1a}$, $R^{1b}$, $R^{1c}$, $R^6$ and $R^7$) may be absent if the valency of the group to which they are attached does not permit such substitution. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes that can be incorporated into the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention.

Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, trifluoroacetic, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

The subject compounds may be useful in a method of treating a cardiovascular or cerebrovascular disease, or a neurological or psychiatric disorder associated with PDE9 dysfunction in a patient such as a mammal in need of such inhibition comprising the administration of an effective amount of the compound. In addition to primates, especially humans, a variety of other mammals may be treated according to the method of the present invention. The subject compounds may be useful in a method of inhibiting PDE9 activity in a patient such as a mammal in need of such inhibition comprising the administration of an effective amount of the compound. The subject compounds may also may be useful for treating a neurological or psychiatric disorder associated with striatal hypofunction or basal ganglia dysfunction in a mammalian patient in need thereof. The subject compounds may also may be useful for treating a cardiovascular and cerebrovascular disease, such as hypertension and heart failure. In addition to primates, especially humans, a variety of other mammals may be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE9 dysfunction in a mammalian patient in need thereof. The present invention is further directed to a use of a compound of the present invention or a pharmaceutically acceptable salt thereof for the manufacture of a medicament for treating neurological and psychiatric disorders, such as schizophrenia, psychosis or Huntington's disease, and those associated with striatal hypofunction or basal ganglia dysfunction, and cardiovascular and cerebrovascular diseases, such as hypertension and heart failure, in a mammalian patient in need thereof.

As used herein, the terms "treatment" and "treating" refer to processes wherein there may be a slowing, interrupting, arresting, controlling, or stopping of the progression of the diseases or disorders described herein, but does not necessarily indicate a total elimination of all disease or disorder symptoms, as well as the prophylactic therapy to retard the progression or reduce the risk of the noted conditions, particularly in a patient who is predisposed to such disease or disorder, but does not yet experience or display symptoms of the disease state, inhibiting the disease state, i.e., arresting the development of the disease state or its clinical symptoms, or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Inhibitors of PDE9, and in particular inhibitors of PDE9A, may provide therapeutic benefit to those individuals suffering from psychiatric and cognitive disorders. The conserved localization of PDE9 in cortex and hippocampus of rodents and humans, brain regions that play a key role in memory and learning, together with the previously described role for NO/cGMP/PKG signaling in synaptic plasticity and cognition has focused attention on a possible role for PDE9 in cognitive function and consequently as a therapeutic target for cognitive dysfunction in Alzheimer's disease and schizophrenia. The mechanism by which PDE9 inhibition improve cognitive function through the modulation of glutamate and/or cholinergic neuron signaling is potentially feasible given that both glutamate (NMDA) and cholinergic receptor activation enhance the formation of cGMP in brain and both neural substrates are involved in cognitive function.

As used herein, the term "selective PDE9 inhibitor" refers to an organic molecule that effectively inhibits an enzyme from the PDE9 family to a greater extent than enzymes from the PDE 1-8 or PDE10-11 families. In one embodiment, a selective PDE9 inhibitor is an organic molecule having a Ki for inhibition of PDE9 that is less than or about one-tenth that for a substance that is an inhibitor for another PDE enzyme. In other words, the organic molecule inhibits PDE9 activity to the same degree at a concentration of about one-tenth or less than the concentration required for any other PDE enzyme. Preferably, a selective PDE9 inhibitor is an organic molecule, having a Ki for inhibition of PDE9 that is less than or about one-hundredth that for a substance that is an inhibitor for another PDE enzyme. In other words, the organic molecule inhibits PDE9 activity to the same degree at a concentration of about one-hundredth or less than the concentration required for any other PDE enzyme. A "selective PDE9 inhibitor" can be identified, for example, by comparing the ability of an organic molecule to inhibit PDE9 activity to its ability to inhibit PDE enzymes from the other PDE families. For example, an organic molecule may be assayed for its ability to inhibit PDE9 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8A, PDE8B, PDE10A, and/or PDE11A.

Phosphodiesterase enzymes including PDE9 have been implicated in a wide range of biological functions. This has suggested a potential role for these enzymes in a variety of disease processes in humans or other species. The compounds of the present invention may have utility in treating a variety of neurological and psychiatric disorders, such as schizophrenia, psychosis or Huntington's disease, and those associated with striatal hypofunction or basal ganglia dysfunction, and cardiovascular and cerebrovascular diseases, such as hypertension and heart failure.

In an embodiment, compounds of the present invention may provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another embodiment, the compounds of the present invention may provide a method for treating cognitive disorders or enhancing cognition comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another embodiment, compounds of the present invention may provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another embodiment, compounds of the present invention may provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another embodiment, compounds of the present invention may provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another embodiment, compounds of the present invention may provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another embodiment, compounds of the present invention may provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other embodiments, compounds of the invention may provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

In another embodiment, compounds of the present invention may provide a method for treating hypertension, such as essential hypertension (also known as primary or idiopathic hypertension) which is a form of hypertension for which no cause can be found, systemic hypertension, pulmonary hypertension (e.g. pulmonary arterial hypertension, pulmonary hypertension of the neonate), and heart failure (which includes both acute heart failure and chronic heart failure, the latter also known as congestive heart failure). The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of the present invention could be used in methods for treatment of, prevention of or reduction of risk for developing one or more disorders such as pulmonary hypertension, particularly pulmonary arterial hypertension, cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions.

In a specific embodiment, compounds of the present invention may provide a method for treating thrombosis, atherosclerosis, restenosis, hypertension, angina pectoris, angiogenesis related disorders, arrhythmia, a cardiovascular or circulatory disease or condition, acute coronary syndrome, coronary artery disease, thrombosis, conditions of reduced blood vessel patency (for example post percutaneous transluminal coronary angioplasty), peripheral vascular disease, renal disease (especially that occurring with diabetes), angina (including stable, unstable and variant (Prinzmetal) angina), myocardial ischaemia, myocardial infarction, secondary prevention of myocardial infarction or stroke, urgent coronary revascularization, glomerulonephritis, thrombotic stroke, thromboembolytic stroke, peripheral artery disease, deep vein thrombosis, venous thromboembolism, cardiovascular disease associated with hormone replacement therapy, atherosclerosis, hypercholesterolemia, coronary heart disease, metabolic syndrome, acute coronary syndrome, disseminated intravascular coagulation syndrome, cerebral infarction, and conditions associated with cardiopulmonary bypass surgery, cardiac valve repair and replacement surgery, pericardial and aortic repair surgeries, such as bleeding, thrombotic vascular events (such as thrombosis or restenosis), vein graft failure, artery graft failure, atherosclerosis, angina pectoris, myocardial ischemia, acute coronary syndrome, myocardial infarction, heart failure, arrhythmia, hypertension, transient ischemic attack, cerebral function impairment, thromboembolic stroke, cerebral ischemia, cerebral infarction, thrombophlebitis, deep vein thrombosis and peripheral artery disease.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE9 inhibitors may be readily determined without undue experimentation using a fluorescence polarization (FP) methodology that is well known in the art (Huang, W., et al., *J. Biomol Screen,* 2002, 7: 215). In particular, the compounds of the following examples had activity in reference assays by exhibiting the ability to inhibit the hydrolysis of the phosphosphate ester bond of a cyclic nucleotide.

In a typical experiment the PDE9 inhibitory activity of the compounds of the present invention was determined in accordance with the following experimental method.

Human PDE9 (PDE9A2, GenBank Accession No. NM_001001567), full length with N-terminal GST tag, was purchased from BPS Bioscience. The fluorescence polarization assay for cyclic nucleotide phosphodiesterases was performed using an IMAP® FP kit supplied by Molecular Devices, Sunnyvale, Calif. (product #R8139). IMAP® technology has been applied previously to phosphodiesterase assays (Huang, W., et al., *J. Biomol Screen,* 2002, 7: 215). Assays were performed at room temperature in 384-well microtiter plates with an incubation volume of 20.2 µL.

Solutions of test compounds were prepared in DMSO and serially diluted with DMSO to yield 8 µL of each of 10 solutions differing by 3-fold in concentration, at 32 serial dilutions per plate. 100% inhibition is determined using a known PDE9 inhibitor, such as 1-(2-chlorophenyl)-6-[(2R)-3,3,3-trifluoro-2-methylpropyl]-1,5-dihydro-4H-pyrazolo[3,4-d]pyrimidine-4-one (BAY 73-6691) (Wunder et al, Mol. Pharmacol., 2005, 68(6): 1775-81), (6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one (PF-04447943) (Wager et al., ACS Chemical Neuroscience, 2010, 1:435-449). 0% of inhibition is determined by using DMSO (1% final concentrations). A Labcyte Echo 555 (Labcyte, Sunnyvale, Calif.) is used to dispense 200 nL from each well of the titration plate to the 384 well assay plate. Human PDE9A2 membrane preps were diluted to 1 ng/ml. FAM-labeled cGMP substrate (Molecular Devices, Sunnyvale, Calif.) was at a concentration of 100 nM (Km of PDE9 for cGMP is 70-170 nM) in the assay buffer (10 mM Tris HCl, pH 7.2, 10 mM $MgCl_2$, 0.05% $NaN_3$ 0.01% Tween-20, and 1 mM DTT). PDE9 enzyme mix and compounds were mixed and incubated at room temperature for 30 min. Following which, FAMcGMP substrate was added, shaken and incubated for an additional 60 min at room temperature. The final concentration of human PDE9 membrane preparations were 0.5 ng/ml. The final concentration of FAM-cGMP was 50 nM. After the incubation period, the enzymatic reaction was stopped by addition of binding solution (IMAP-FP, Molecular Devices, comprised of 80% Solution A, 20% Solution B and a 1:600 dilution of binding reagent) to each well. The plates were shaken then incubated at room temperature for 1 h prior to determining the fluorescence polarization (mP) using a Perkin Elmer EnVision™ plate reader (Waltham, Mass.).

Fluorescence polarization (mP) was calculated from the parallel (S) and perpendicular (P) fluorescence of each sample well and the analogous values for the median control well, containing only substrate (So and Po), using the following equation:

Polarization(mP)=1000*(S/So−P/Po)/(S/So+P/Po).

Dose-inhibition profiles for each compound were characterized by fitting the mP data to a four-parameter equation given below. The apparent inhibition constant ($K_I$) the maximum inhibition at the low plateau relative to "100% Inhibition Control" (Imax; e.g. 1=> same as this control), the minimum inhibition at the high plateau relative to the "0% Inhibition Control" (Imin, e.g. 0=> same as the no drug control) and the Hill slope (nH) are determined by a nonlinear least squares fitting of the mP values as a function of dose of the compound using an in-house software based on the procedures described by Mosser et al., *JALA*, 2003, 8: 54-63, using the following equation:

$$mP = \frac{(0\%\ mP - 100\%\ mP)(Imax - Imin)}{1 + \left[\frac{[Drug]}{\left(10^{-pK_I}\left(1 + \frac{[Substrate]}{K_M}\right)\right)}\right]^{nH}} +$$

$$100\%\ mP + (0\%\ mP - 100\%\ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE9, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat #60010), PDE3A (Cat #60030), PDE4A1A (Cat #60040), PDE5A1 (Cat #60050), PDE6C (Cat #60060), PDE7A (Cat #60070), PDE8A1 (Cat #60080), PDE9A2 (Cat #60090), PDE11A4 (Cat #60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product #R7506 or cGMP #R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour. The parallel and perpendicular fluorescence of each well of the plate was measured using a Perkin Elmer EnVision™ plate reader (Waltham, Mass.).

The apparent inhibition constants for the compounds against all 11 PDE's was determined from the parallel and perpendicular fluorescent readings as described for PDE FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

The compounds of the following examples had activity in inhibiting the human PDE9 enzyme in the aforementioned assays, generally with a Ki of less than about 500 nM. Many of compounds within the present invention had activity in inhibiting the human PDE9 enzyme in the aforementioned assays with a Ki of less than about 100 nM, and wherein some of the compounds have a Ki of less than about 10 nM. Additional data are provided in the following Examples.

Such a result is indicative of the intrinsic activity of the compounds in use as inhibitors of the PDE9 enzyme. In general, one of ordinary skill in the art would appreciate that a substance is considered to effectively inhibit PDE9 activity if it has a Ki of less than or about 500 nM, where more potent inhinbitors have a Ki of less than or about 100 nM. The present invention also includes compounds within the scope of the invention which possess activity as inhibitors of other phosphodiesterase enzymes.

The subject compounds may be further useful in a method for the prevention, treatment, control, amelioration, or reduction of risk of the diseases, disorders and conditions noted herein. The subject compounds may be further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In one embodiment, the subject compound may be employed in combination with thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors; pepstatin derivatives and fluoro- and chloro-derivatives of statone-containing peptides; enalkrein; aliskiren (2(S), 4(S), 5(S), 7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate)); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholytics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), SGLT2 inhibitors (e.g. sotagliflozin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of the present invention, or the active agent(s) therein could be used in a fixed dose drug combination including a compound of the present invention.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds may be further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 100 mg per patient per day which may be administered in single or multiple doses. In one embodiment, the dosage range will be about 0.5 mg to 50 mg per patient per day; in another embodiment about 0.5 mg to 20 mg per patient per day; and in yet another embodiment about 0.5 mg to 5 mg per patient per day. Pharmaceutical compositions of the present invention may be provided in a solid dosage formulation such as comprising about 0.5 mg to 100 mg active ingredient, or comprising about 0.5 mg to 50 mg active ingredient. The pharmaceutical composition may be provided in a solid dosage formulation comprising about 0.5 mg, 1 mg, 5 mg, 10 mg, 25 mg, 50 mg, or 100 mg active ingredient. For oral administration, the compositions may be provided in the form of tablets containing 0.5 to 100 milligrams of the active ingredient, such as 0.5, 1, 5, 10, 15, 20, 25, 50, 75, and 100 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; ACN: acetonitrile; TFA: trifluoroacetic acid; DCM: dichloromethane; DMSO: dimethyl sulfoxide; MTBE: methyl tert-butyl ether; DMPU: 1,3-Dimethyl-3,4,5,6-tetrahydro-2(1H)-pyrimidinone; DAST: Diethylaminosulfur trifluoride; TBAI: tetrabutylamonium iodide; HATU: (1-[Bis(dimethylamino)methylene]-1H-1,2,3-triazolo[4,5-b]pyridinium 3-oxid hexafluorophosphate; ttbtpy: 4,4',4"-Tri-tert-Butyl-2,2':6',2"-terpyridine; CAN: Ceric ammonium nitrate; rt: room temperature; HPLC: high performance liquid chromatography; NMR: nuclear magnetic resonance; TLC: thin-layer chromatography.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

SCHEME 1

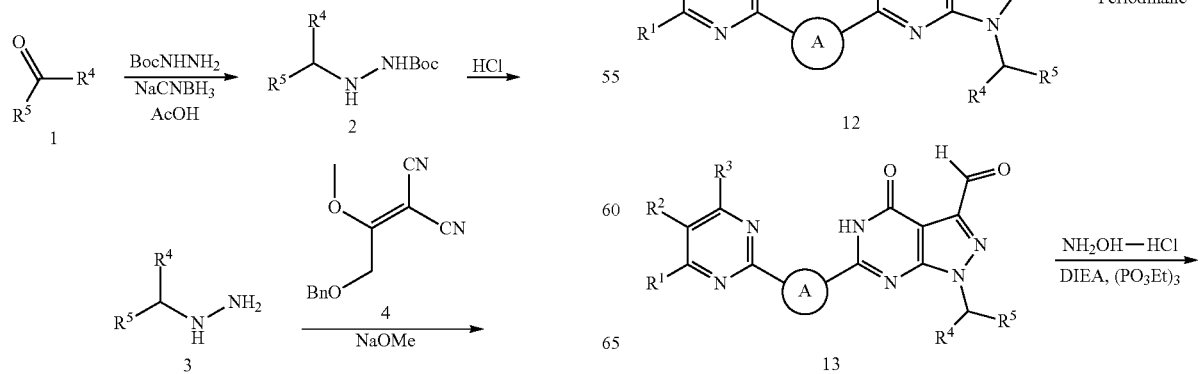
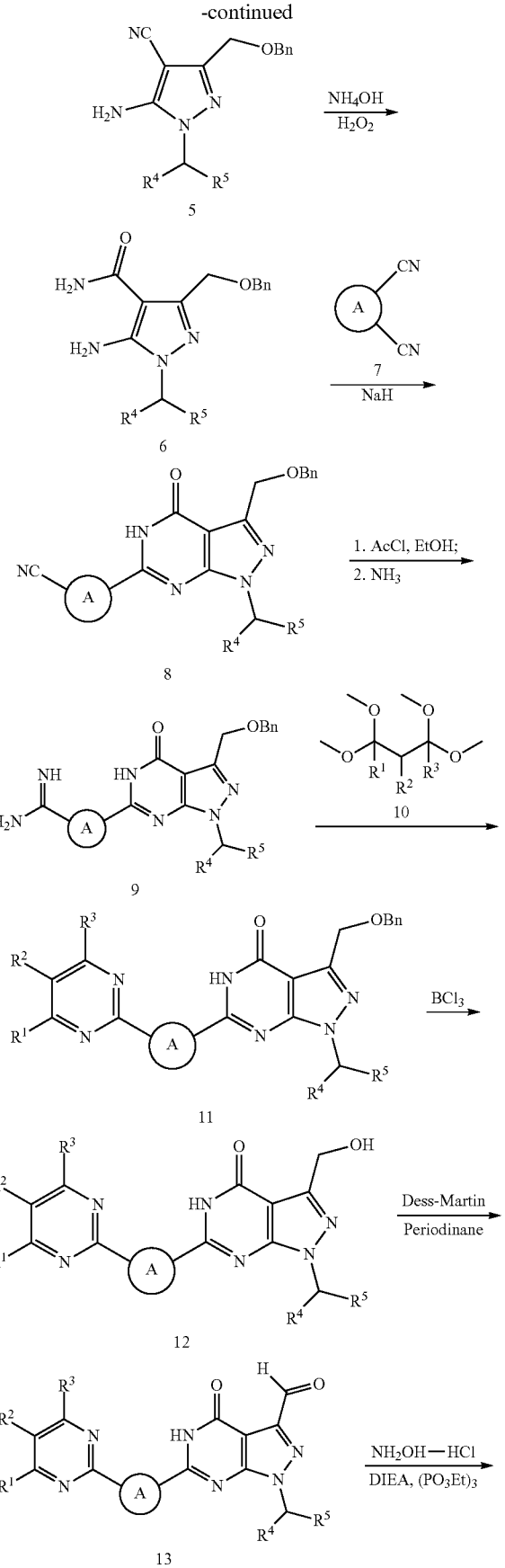

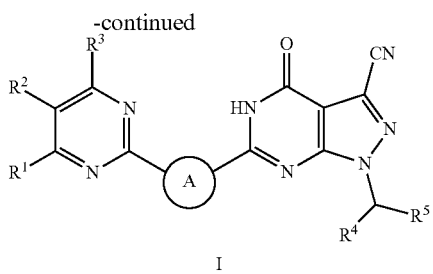

I

Compounds of the Formula I may be prepared by first reacting ketones or aldehydes 1 with Boc-hydrazine to afford 2 which can be treated with an acid, such as HCl to afford hydrazines 3. Reaction of hydrazines 3 with olefin 4 under basic conditions affords pyrazoles 5. Treatment of 5 with ammonium hydroxide and hydrogen peroxide provides 6 which is subsequently reacted with trans racemic 7 to afford trans racemic 8. The nitrile of 8 is then converted to pyrimidine 11 by first treatment with acidic ethanol followed by ammonia to afford 9 and annulation with diacetal 10 to provide 11. Conversion to I occurs in three steps, first benzyl group removal using $BCl_3$ to provide 12, followed by oxidation using an oxidant such as, for example, Dess-Martin Periodinane to afford 13 and finally nitrile formation to generate I.

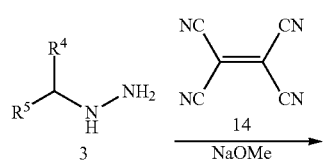

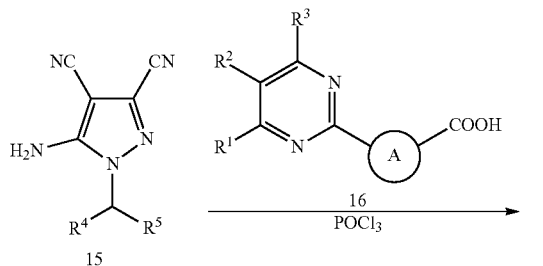

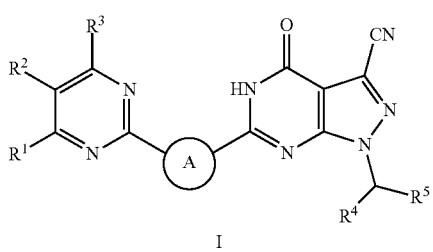

I

Alternatively, compounds of the Formula I may be prepared by first reaction of hydrazines 3 with olefin 14 to generate pyrazole 15. Reaction of 15 with acids 16 in the presence of $POCl_3$ can generate compounds I.

SCHEME 3

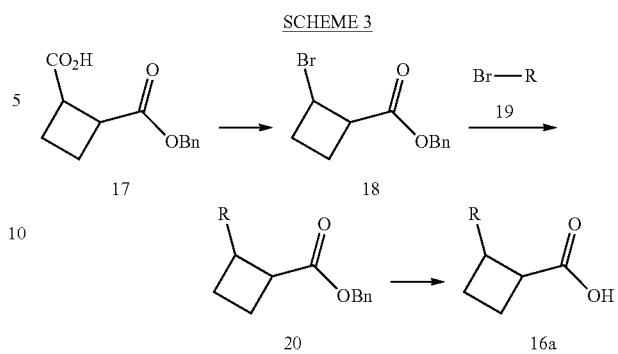

Cyclobutanecarboxylic acid 16a was prepared as depicted in Scheme 3. Benzyl 2-bromocyclobutanecarboxylate 18, obtained by the decarboxylative bromination of 17, was mixed with TBAI, nickel(II) iodide, ttbtpy, zinc, pyridine, and substituted bromide such as 19 in degassed DMPU to afford benzyl 2-cyclobutanecarboxylate such as 20. The latter was then hydrolyzed using LiOH to afford 2-cyclobutanecarboxylic acid such as 16a.

Intermediate 1

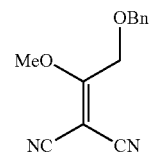

2-(2-(Benzyloxy)-1-methoxyethylidene)malononitrile

Step A: 2-(Benzyloxy)acetyl chloride. Into a 5000-mL 4-necked round-bottom flask purged and maintained with an inert atmosphere of nitrogen, was placed 2-(benzyloxy) acetic acid (500 g, 3.01 mol), dichloromethane (2500 mL), N,N-dimethylformamide (5 mL). This was followed by the addition of oxalic dichloride (458.3 g, 3.61 mol) at room temperature. The resulting solution was stirred overnight at room temperature. The resulting mixture was concentrated under vacuum. The resulting solution was diluted with 200 mL of DCM. The resulting mixture was concentrated under vacuum. The resulting solution was diluted with 200 mL of DCM. The resulting mixture was concentrated under vacuum. The crude material was used in next step without further purification.

Step B: 2-[2-(Benzyloxy)-1-hydroxyethylidene]propanedinitrile. Into a 3000-mL 4-necked round-bottom flask purged and maintained with an inert atmosphere of nitrogen, was placed tetrahydrofuran (1100 mL), propanedinitrile (195 g, 2.95 mol). This was followed by the addition of sodium hydride (236.16 g, 5.90 mol, 60%) in several batches at 0° C. over 20 min. To this was added 2-(benzyloxy)acetyl chloride (545 g, 2.95 mol) dropwise with stirring at 0° C. The resulting solution was stirred for 2 h at 0° C. The reaction was then quenched by the addition of 500 mL of water at 0° C. The resulting solution was diluted with 2000 mL of hydrogen chloride (1 mol/L). The resulting solution was extracted with 3×1000 mL of ethyl acetate and the organic layers combined. The resulting mixture was washed with 2×1000 mL of brine. The mixture was dried over anhydrous magnesium sulfate and concentrated under vacuum. The residue was applied onto a silica gel column with ethyl acetate/petroleum ether (1:10) to afford the title compound. LCMS (ES, m/z): 215.2 [M+H]⁺.

Step C: 2-[2-(benzyloxy)-1-methoxyethylidene]propanedinitrile. Into a 20-L 4-necked round-bottom flask purged and maintained with an inert atmosphere of nitrogen, was placed 2-[2-(benzyloxy)-1-hydroxyethylidene]propanedinitrile (457 g, 2.13 mol), dioxane (7000 mL), sodium bicarbonate (609.3 g, 7.25 mol), dimethyl sulfate (376.7 g, 2.99 mol). The resulting solution was stirred overnight at 85° C. The solids were filtered out. The filtrate was concentrated under vacuum. The resulting solution was diluted with 2000 mL of water. The resulting solution was extracted with 3×2000 mL of ethyl acetate and the organic layers combined. The resulting mixture was washed with 2×1000 mL of brine. The mixture was dried over anhydrous magnesium sulfate and concentrated under vacuum. The residue was applied onto a silica gel column with ethyl acetate/petroleum ether (1:10) and afforded the title compound. LCMS (ES, m/z): 229.0 [M+H]⁺.

Intermediate 2

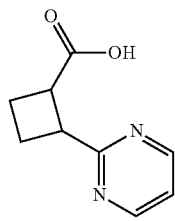 [SMILES: O=C(O)C1CCC1c1ncccn1]

trans-2-(Pyrimidin-2-yl)cyclobutane-1-carboxylic acid

Step A: Diethyl 1-cyanocyclobutane-1,2-dicarboxylate. An oven dried round bottom flask was charged with diethyl 2,5-dibromohexanedioate (25 g, 69.4 mmol) in ethanol (50 mL). Potassium cyanide (12.75 g, 196 mmol) was added and the contents were stirred at 90° C., for 28 h. The reaction mixture was cooled to 0° C., brine (300 mL) was added and the mixture extracted with diethyl ether (3×300 mL). The combined organic fractions were dried over anhydrous sodium sulfate, filtered and concentrated under reduced pressure to yield the crude title compound which was taken to next step without further purification.

Step B: Ethyl 2-cyanocyclobutanecarboxylate. An oven dried round bottom flask (500 mL) was charged with diethyl 1-cyanocyclobutane-1,2-dicarboxylate (15.7 g, 69.7 mmol) in DMSO (80 mL). Sodium chloride (8.15 mL, 139 mmol), water (3.14 mL, 174 mmol) were added and the contents were stirred at 150° C., for 4 h. The reaction mixture was cooled to 0° C., quenched with brine, extracted with diethyl ether (3×200 mL), dried over anhydrous sodium sulfate, filtered and concentrated under reduced pressure to yield the crude title compound which was taken to next step without further purification.

Step C: 2-Carbamimidoylcyclobutanecarboxylic acid hydrochloride. An oven dried round bottom flask (2000 mL) was charged with ethanol (300 mL) in chloroform (300 mL) cooled to 0° C., acetyl chloride (139 mL, 1959 mmol) was added drop wise and the contents were stirred at 0° C. for 20 minutes. Ethyl 2-cyanocyclobutanecarboxylate (10.0 g, 65.3 mmol) in chloroform (50 mL) was added and the contents were stirred at room temperature for 12 h. The reaction mixture was concentrated under reduced pressure, the crude was dissolved in ethanol (300 mL) cooled to 0° C., ammonia in methanol (410 mL, 2872 mmol) was added and the contents were stirred at room temperature for 12 h, and concentrated under reduced pressure to yield the crude title compound.

Step D: Methyl-2-(pyrimidin-2-yl)cyclobutanecarboxylate. An oven dried pressure tube (250 mL) was charged with crude 2-carbamimidoylcyclobutanecarboxylic acid (13.0 g, 91 mmol) in 1,1,3,3-tetramethoxypropane (50 mL) and the contents were stirred at 160° C., for 18 h. The reaction mixture was cooled to room temperature, concentrated under reduced pressure. The crude was purified by column chromatography on silica eluted with 20-80% ethyl acetate in petroleum ether to yield the title compound. LCMS (ES, m/z): 193.4 [M+H]⁺.

Step E: 2-(Pyrimidin-2-yl)cyclobutanecarboxylic acid. An oven dried round bottom flask (100 mL) was charged with methyl 2-(pyrimidin-2-yl)cyclobutanecarboxylate (4.0 g, 20.81 mmol), water (40.0 mL) and tetrahydrofuran (40.00 mL) at room temperature. Lithium hydroxide (1.495 g, 62.4 mmol) was added and the contents were stirred at room temperature for 72 h. The reaction mixture was concentrated under reduced pressure, and the aqueous reaction mixture was washed with diethyl ether (2×20 mL), aqueous mass was cooled to 0° C. and neutralized with 10% potassium hydrogen sulfate, extracted with ethyl acetate (3×100 mL). The combined organic layers were washed with brine (50 mL), dried over anhydrous sodium sulfate, filtered and concentrated under reduced pressure to yield the title compound. ¹H NMR (CDCl₃, 400 MHz): δ 8.79 (d, J=5.20 Hz, 2H), 7.32 (t, J=4.80 Hz, 1H), 4.04-4.02 (m, 1H), 3.50-3.50 (m, 1H), 2.43-2.37 (m, 4H). LCMS (ES, m/z): 179.0 [M+H]⁺.

Intermediate 3

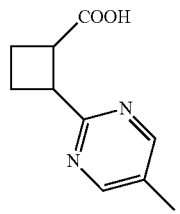

2-(5-Methylpyrimidin-2-yl)cyclobutanecarboxylic acid

Step A: To a solution of ethanol (9.61 mL, 0.17 mol) and DCM (8.4 mL) was added AcCl (11.70 mL, 0.17 mol) at 0° C. under N₂. The reaction solution was stirred at 0° C. for 30 min before ethyl 2-cyanocyclobutanecarboxylate (1.68 g, 10.97 mmol) was added. The reaction solution was stirred at 0° C. for 3 h, and was then gradually warmed to 15° C.-20° C. and stirred for 6 h at this temperature before being concentrated under vacuum to afford the crude product which was used for next step directly. To a solution of the crude product in MeOH (4 mL) was added ammonia (40 mL, 0.28 mol) (7 M in MeOH) at 0° C. under N₂, and the reaction solution was stirred at room temperature for 2 h before being concentrated under vacuum to afford 2-carbamimidoylcyclobutanecarboxylic acid, which was used directly for next step without further purification. (ES, m/z): 143.1 [M+H]$^+$.

Step B: To a solution of 2-carbamimidoylcyclobutanecarboxylic acid (1.30 g, 9.14 mmol) in MeOH (2 mL) were added sodium methanolate (0.99 g, 18.29 mmol) and (Z)-3-(dimethylamino)-2-methylacrylaldehyde (1.24 g, 10.97 mmol) at room temperature under $N_2$. The reaction mixture was degassed with $N_2$ for 3 times and stirred at 80° C. for 16 h. The resulting mixture was concentrated under vacuum. The residue was dissolved in MeOH (5 mL) and purified by C18 column under the following conditions: Mobile Phase A: waters with 0.5% TFA, Mobile Phase B: ACN; Flow rate: 50 mL/min; Gradient: 0% B to 60% B in 20 min; 254/210 nm. The fractions containing desired product were combined and concentrated under vacuum to afford 2-(5-methylpyrimidin-2-yl)cyclobutanecarboxylic acid. (ES, m/z): 193.1 [M+H]$^+$.

Intermediate 4

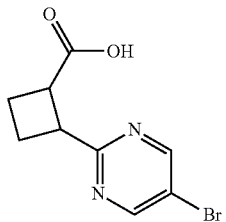 [SMILES: O=C(O)C1CCC1c1ncc(Br)cn1]

2-(5-Bromopyrimidin-2-yl)cyclobutanecarboxylic acid

Step A: To a solution of $CHCl_3$ (16.30 mL) and EtOH (16.30 mL) was added acetyl chloride (5.36 mL, 75.00 mmol) dropwise at 0° C. over 20 minutes. Ethyl 2-cyanocyclobutanecarboxylate (0.50 g, 3.26 mmol) in $CHCl_3$ (13 mL) was then added at 0° C. dropwise to the previous solution, and the reaction solution was stirred at room temperature for 20 h. The resulting solution was concentrated under vacuum to afford ethyl 2-(ethoxy(imino)methyl)-cyclobutanecarboxylate which was used directly for next step without further purification. (ES, m/z): 200.1 [M+H]$^+$.

Step B: To a solution of 5-bromo-1,2,3-triazine (3.98 g, 24.88 mmol) in ACN (25 mL) was added ethyl 2-(ethoxy(imino)methyl)cyclobutanecarboxylate (8.40 g, 42.20 mmol), and the reaction mixture was stirred at room temperature for 5 minutes before heated to 80° C. and stirred for 24 h. The resulting mixture was concentrated under vacuum. The residue was purified by a silica gel column chromatography, eluted with gradient 5%-25% EtOAc in petroleum ether. The fractions containing desired product were combined and concentrated under vacuum to afford ethyl 2-(5-bromopyrimidin-2-yl)cyclobutanecarboxylate. (ES, m/z): 285.0, 287.0 [M+H]$^+$.

Step C: To a solution of ethyl 2-(5-bromopyrimidin-2-yl)cyclobutanecarboxylate (1.00 g, 3.51 mmol) in THF (10 mL) was added LiOH (1M in water; 5.26 mL, 5.26 mmol) at room temperature. The reaction mixture was stirred at room temperature overnight before being concentrated under vacuum. The residue was dissolved in MeOH (5 mL) and purified by Prep-HPLC with the following conditions: column: X Bridge C18 OBD Prep Column 60 Å, 40-60 μm, 19 mm×250 mm; Mobile Phase A: water with 5 mmol/L TFA, Mobile Phase B: ACN; Flow rate: 70 mL/min; Gradient: 5% B to 95% B in 8 min; 254/210 nm. The fractions containing desired product were combined and concentrated under vacuum to afford 2-(5-bromopyrimidin-2-yl)cyclobutanecarboxylic acid. (ES, m/z): 257.0, 259.0 [M+H]$^+$.

Intermediate 5

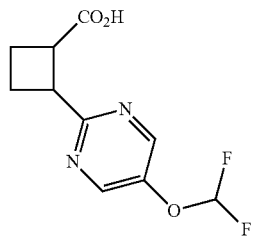 [SMILES: O=C(O)C1CCC1c1ncc(OC(F)F)cn1]

2-(5-(Difluoromethoxy)pyrimidin-2-yl)cyclobutanecarboxylic acid

Step A: To a solution of ethyl 2-(5-bromopyrimidin-2-yl) cyclobutanecarboxylate (0.20 g, 0.70 mmol) in DMF (2.5 mL) were added $Cs_2CO_3$ (0.46 g, 1.40 mmol), RockPhos Pd $G_3$ (17.64 mg, 0.02 mmol) and (E)-benzaldehyde oxime (0.11 g, 0.91 mmol). The reaction mixture was degassed with $N_2$ for 3 times and stirred at 90° C. for 16 h. The resulting mixture was diluted with water (20 mL) and extracted with EtOAc (3×20 mL). The combined organic layers was washed with brine (3×20 mL), dried over anhydrous $Na_2SO_4$ and filtered. The filtrate was concentrated under vacuum. The residue was purified by reverse phase (C18) column with gradient 1%-40% ACN in water with 0.05% TFA as eluent. The fractions containing desired product were combined and concentrated under vacuum to afford ethyl 2-(5-hydroxypyrimidin-2-yl)cyclobutanecarboxylate. (ES, m/z): 223.2 [M+H]$^+$.

Step B: To a solution of ethyl 2-(5-hydroxypyrimidin-2-yl)cyclobutanecarboxylate (80 mg, 0.36 mmol) in DMF (1.2 mL) were added ethyl 2-bromo-2,2-difluoroacetate (0.22 g, 1.08 mmol) and $Cs_2CO_3$ (0.24 g, 0.72 mmol) at room temperature. The reaction mixture was stirred at 80° C. for 48 h. The resulting mixture was cooled to room temperature and filtered. The filtrate was purified by Prep-HPLC with the following conditions: Column: X Bridge C18 OBD Prep Column 100 Å, 10 μm, 19 mm×150 mm; Mobile Phase A: water with 0.05% TFA, Mobile Phase B: ACN; Flow rate: 25 mL/min; Gradient: 10% B to 35% B in 6.5 min; 254/210 nm. The fractions containing desired product were combined and concentrated under vacuum to afford ethyl 2-(5-(difluoromethoxy)pyrimidin-2-yl) cyclobutanecarboxylate. (ES, m/z): 273.2 [M+H]$^+$.

Step C: To a solution of ethyl 2-(5-(difluoromethoxy) pyrimidin-2-yl)cyclobutanecarboxylate (60.00 mg, 0.22 mmol) in THF (0.5 mL) was added LiOH (1 M in water; 0.33 mL, 0.33 mmol) at room temperature. The reaction mixture was stirred at room temperature for 16 h before being concentrated under vacuum. The residue was dissolved in DMF and purified by Prep-HPLC with the following conditions: column: X Bridge C18 OBD Prep Column 100 Å, 10 μm, 19 mm×150 mm; Mobile Phase A: water with 0.05% TFA, Mobile Phase B: ACN; Flow rate: 25 mL/min; Gradient: 10% B to 35% B in 7 min; 254/210 nm. The fractions containing desired product were combined and concentrated under vacuum to afford 2-(5-(difluoromethoxy)-pyrimidin-2-yl) cyclobutanecarboxylic acid. (ES, m/z): 245.1 [M+H]$^+$.

Intermediate 6

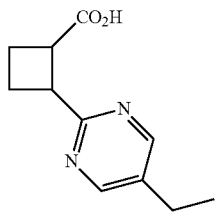

2-(5-Ethylpyrimidin-2-yl)cyclobutanecarboxylic acid

Step A: To a solution of ethyl 2-(5-bromopyrimidin-2-yl)cyclobutanecarboxylate (0.10 g, 0.35 mmol) in THF (0.50 mL) were added Pd(PPh$_3$)$_4$ (40.50 mg, 0.035 mmol) and triethylaluminum (60.10 mg, 0.53 mmol). The reaction mixture was degassed with N$_2$ for 3 times and stirred at 70° C. for 20 h. The resulting mixture was quenched with MeOH (2 mL), filtered and washed with EtOAc (10 mL). The filtrate was concentrated and the residue was purified by Prep-TLC (petroleum ether/EtOAc=2/1). The fractions containing desired product were combined and concentrated under vacuum to afford ethyl 2-(5-ethylpyrimidin-2-yl)cyclobutanecarboxylate. (ES, m/z): 235.1 [M+H]$^+$.

Step B: To a solution of ethyl 2-(5-ethylpyrimidin-2-yl) cyclobutanecarboxylate (60.00 mg, 0.26 mmol) in THF (0.5 mL) and water (0.5 mL) was added LiOH (9.2 mg, 0.38 mmol) at room temperature. The reaction mixture was stirred at room temperature for 16 h. The resulting mixture was concentrated under vacuum and the residue was purified by Prep-HPLC with the following conditions: column: Sunfire Prep C18 OBD Column, 10 um, 19*250 mm; Mobile Phase A: water with 0.05% TFA, Mobile Phase B: ACN; Flow rate: 25 mL/min; Gradient: 12% B to 60% B in 8 min; 254/210 nm. The fractions containing desired product were combined and concentrated under vacuum to afford 2-(5-ethylpyrimidin-2-yl)cyclobutanecarboxylic acid. (ES, m/z): 207.1 [M+H]$^+$.

Intermediate 7

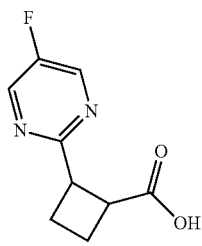 [SMILES: O=C(O)C1CCC1c1ncc(F)cn1]

2-(5-Fluoropyrimidin-2-yl)cyclobutanecarboxylic acid

Step A: TBAI (86 mg, 0.23 mmol), nickel(II) iodide (29 mg, 0.09 mmol), ttbtpy (37 mg, 0.09 mmol) and zinc (0.12 g, 1.86 mmol) was added to a vial. The mixture was degassed with N$_2$. Degassed DMPU (3 mL) was added followed by pyridine (7.51 μL, 0.09 mmol). The reaction mixture was stirred for 2 h followed by the addition of the solution of 2-bromo-5-fluoropyrimidine (0.25 g, 1.39 mmol) and benzyl 2-bromocyclobutanecarboxylate (0.25 g, 0.93 mmol) in DMPU (2 mL). The resulting mixture was stirred at room temperature for 2 days before being quenched with 1 M NaHSO$_4$, and extracted with MTBE (2×20 mL). The combined organic layer was washed with water (2×20 ml), brine (20 mL), dried over anhydrous MgSO$_4$ and filtered. The filtrate was concentrated under vacuum. The residue was purified by silica gel column chromatography, eluting withEtOAc/hexanes (1:20 to 1:5). The fractions containing desired product were combined and concentrated under vacuum to afford benzyl 2-(5-fluoropyrimidin-2-yl)cyclobutanecarboxylate (~11:1 trans:cis mixture). LCMS (m/z): 287.1 [M+H]$^+$.

Step B: To a mixture of benzyl 2-(5-fluoropyrimidin-2-yl)cyclobutanecarboxylate (0.25 g, 0.87 mmol) in MeOH (0.30 mL), THF (0.30 mL) and water (0.30 mL) was added LiOH (62.70 mg, 2.62 mmol) at room temperature. The reaction mixture was stirred at room temperature for 1 h. The resulting mixture was diluted with MTBE and extracted with 1 N NaOH. The pH value of the solution was adjusted to 1-2 with 6 N HCl, and extracted with MTBE (2×10 mL). The combined organic layer was washed with brine (3×10 mL), dried over anhydrous Na$_2$SO$_4$ and filtered. The filtrate was concentrated under vacuum. The residue was purified by silica gel column chromatography, eluted with gradient 0%-40% EtOAc in petroleum ether. The fractions containing desired product were combined and concentrated under vacuum to afford 2-(5-fluoropyrimidin-2-yl)cyclobutanecarboxylic acid. (ES, m/z): 197.0 [M+H]$^+$.

Intermediate 8

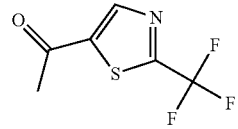

1-(2-(Trifluoromethyl)thiazol-5-yl)ethanone

Step A: To a suspension of ethyl 2-(trifluoromethyl)thiazole-5-carboxylate (11.00 g, 48.80 mmol) (prepared as described by U.S. Pat. No. 5,034,404, 1991) in THF (3.00 mL) and water (1.50 mL) was added NaOH (9.77 g, 244.00 mmol). The reaction mixture was stirred at 20° C. for 4 h. The pH value of the mixture was adjusted to 2-3 by 2N HCl, and the resulting mixture was extracted with EtOAc (3×10 mL). The combined organic layer was washed with brine (3×10 mL), dried over anhydrous Na2SO4 and filtered. The filtrate was concentrated under vacuum. The residue was purified by C18 Phase reversal column (water:ACN=1:1). The fractions containing desired product were combined and concentrated under vacuum to afford 2-(trifluoromethyl)thiazole-5-carboxylic acid. (ES, m/z): 198.0 [M+H]⁺.

Step B: To the mixture of 2-(trifluoromethyl)thiazole-5-carboxylic acid (1.20 g, 6.09 mmol) in DCM (15 mL) was added N,O-dimethylhydroxylamine hydrochloride (0.59 g, 6.09 mmol). The reaction mixture was stirred at room temperature for 5 minutes. HATU (3.47 g, 9.13 mmol) was added to the mixture followed by the addition of Et₃N (3.39 mL 24.35 mmol) after 3 minutes stirring. The reaction mixture was stirred at 20° C. for 4 h before being concentrated under vacuum. The residue was diluted with water (10 mL) and extracted with DCM (3×30 mL). The combined organic layer was washed with brine (3×10 mL), dried over anhydrous Na₂SO₄ and filtered. The filtrate was concentrated under vacuum. The residue was purified by silica gel column chromatography, eluted with gradient 5%-25% EtOAc in petroleum ether. The fractions containing desired product were combined and concentrated under vacuum to afford N-methoxy-N-methyl-2-(trifluoromethyl)thiazole-5-carboxamide. (ES, m/z): 241.0 [M+H]⁺.

Step C: To a solution of N-methoxy-N-methyl-2-(trifluoromethyl)thiazole-5-carboxamide (4.40 g, 18.32 mmol) in THF (20 mL) at 0° C. under N₂ was slowly added a solution of methylmagnesium bromide (1 M in THF) (27.50 mL, 27.50 mmol). The reaction mixture was stirred at 0° C. for 3 h before being poured into aq. NH₄Cl (sat.; 15 mL) and extracted with EtOAc (3×50 mL). The combined organic layer was washed with brine (3×30 mL), dried over anhydrous Na₂SO₄ and filtered. The filtrate was concentrated under vacuum. The residue was purified by silica gel column chromatography eluted with gradient 5%-25% EtOAc in petroleum ether. The fractions containing desired product were combined and concentrated under vacuum to afford 1-(2-(trifluoromethyl)thiazol-5-yl)ethanone. (ES, m/z): 196.0 [M+H]⁺.

Intermediate 9

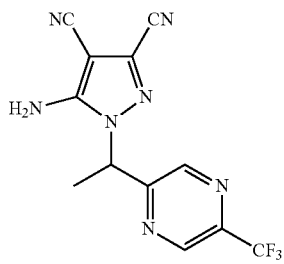 [SMILES: CC(c1cnc(C(F)(F)F)cn1)n1nc(C#N)c(C#N)c1N]

5-Amino-1-(1-(5-(trifluoromethyl)pyrazin-2-yl)ethyl)-1H-pyrazole-3,4-dicarbonitrile To a solution of 2-(1-hydrazinylethyl)-5-(trifluoromethyl)pyrazine (2.20 g, 5.07 mmol) in EtOH (80 mL) was added a solution of NaOH (0.41 g, 10.10 mmol) in EtOH (20 mL) and ethene-1,1,2,2-tetracarbonitrile (0.71 g, 5.57 mmol) at 0° C. The reaction mixture was stirred at 0° C. for 1 h. To the reaction solution was added aq. NaHCO₃ (sat.; 30 mL). The organic solvent was removed under vacuum. The resulting mixture was extracted with EtOAc (3×30 mL). The combined organic layer was washed with brine (3×20 mL), dried over anhydrous Na₂SO₄ and filtered. The filtrate was concentrated under vacuum. The residue was purified by a silica gel column chromatography, eluted with gradient 0%-60% EtOAc in petroleum ether. The fractions containing desired product were combined and concentrated to afford 5-amino-1-(1-(5-(trifluoromethyl)-pyrazin-2-yl)ethyl)-1H-pyrazole-3,4-dicarbonitrile. (ES, m/z): 308.1 [M+H]⁺.

TABLE 1

| Intermediate | Structure | Exact Mass [M + H]⁺ | SFC Column; Peak # |
|---|---|---|---|
| 10 | enantiomer A | 308.1 | Chiralpak-IC; 1 |
| 11 | enantiomer B | 308.1 | Chiralpak IC; 2 |
| 12 | enatiomer A | 289.1 | Chiralpak AS-H; 1 |
| 13 | enatiomer B | 289.1 | Chiralpak AS-H; 2 |

TABLE 1-continued

| Intermediate | Structure | Exact Mass [M + H]+ | SFC Column; Peak # |
|---|---|---|---|
| 14 | enantiomer A | 246.1 | Phenomenex Lux Cellulose-4; 1 |
| 15 | enantiomer B | 246.1 | Phenomenex Lux Cellulose-4; 2 |
| 16 | enantiomer A | 279.1 | Chiralpak AD-H; 1 |
| 17 | enantiomer B | 279.1 | Chiralpak AD-H; 2 |
| 18 | 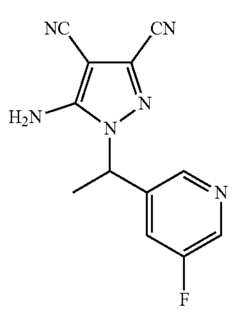 [SMILES: CC(c1cncc(F)c1)n1nc(C#N)c(C#N)c1N] | 257.1 | No separation |
| 19 | 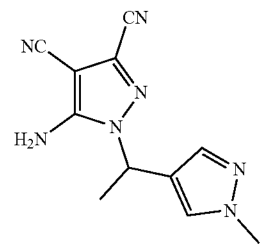 [SMILES: CC(c1cnn(C)c1)n1nc(C#N)c(C#N)c1N] | 242.1 | No separation |
| 20 | 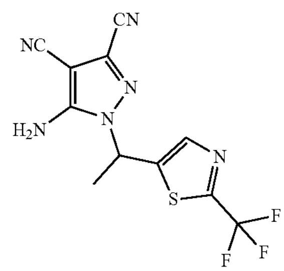 [SMILES: CC(c1cnc(C(F)(F)F)s1)n1nc(C#N)c(C#N)c1N] | 313.0 | No separation |

The following compounds were prepared according to the general procedure provided in the examples and procedures herein using known or prepared starting materials, as described in the reaction schemes and examples herein, such as described for Intermediate 9. The requisite starting materials are either prepared as described herein, commercially available, or may be prepared from commercially available reagents using conventional reactions well known in the art without undue experimentation.

Intermediate 21

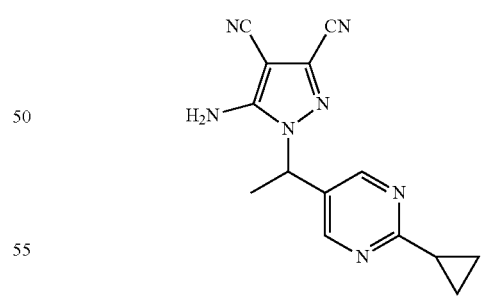

5-Amino-1-(1-(2-cyclopropylpyrimidin-5-yl)ethyl)-1H-pyrazole-3,4-dicarbonitrile

Step A: To a solution of 1-(2-chloropyrimidin-5-yl)ethanone (5.00 g, 31.9 mmol), tert-butyl hydrazinecarboxylate (4.22 g, 31.9 mmol) in EtOH (2 mL) was added AcOH (0.64 mL, 11.18 mmol) at room temperature. The reaction solution was stirred for 1 h. The reaction was concentrated under vacuum to afford (Z)-tert-butyl 2-(1-(2-chloropyrimidin-5-yl)ethylidene)-hydrazinecarboxylate. The crude product was used for next step directly. (ES, m/z): 271.1 [M+H]$^+$.

Step B: To a solution of (Z)-tert-butyl 2-(1-(2-chloropyrimidin-5-yl)ethylidene)-hydrazinecarboxylate (11.50 g, 42.5 mmol) in AcOH (200 mL) was added NaCNBH$_4$ (3.20 g, 51.0 mmol) at room temperature. The reaction solution was stirred overnight at room temperature. The reaction mixture was quenched by NH$_4$Cl (aq.) and then was concentrated. The resulted mixture was extracted with ethyl acetate (3×200 mL), washed with brine (3×200 mL), dried over with anhydrous Na$_2$SO$_4$ and filtered. The filtrate was concentrated under vacuum. The residue was purified by silica gel column chromatography, eluted with gradient 0-50% ethyl acetate in petroleum ether. The fractions containing desired product were combined and concentrated to afford tert-butyl 2-(1-(2-chloropyrimidin-5-yl)ethyl)hydrazinecarboxylate. (ES, m/z): 273.1 [M+H]$^+$.

Step C: To a solution of tert-butyl 2-(1-(2-chloropyrimidin-5-yl)ethyl)hydrazinecarboxylate (0.40 g, 1.47 mmol) in 1,4-dioxane (4 mL) and water (2.00 mL) were added cyclopropylboronic acid (0.38 g, 4.40 mmol), triphenylphosphine (77 mg, 0.29 mmol) and Pd(OAc)$_2$ (32.9 mg, 0.15 mmol) at room temperature. The reaction mixture was degassed with N$_2$ for 3 times and stirred for 16 h at 120° C. The reaction mixture was diluted with water (30 mL) and extracted with ethyl acetate (3×30 mL). The combined organic layer was washed with brine (3×30 mL), dried over anhydrous Na$_2$SO$_4$ and filtered. The filtrate was concentrated under vacuum. The residue was purified by silica gel column chromatography, eluted with gradient 0-50% ethyl acetate in petroleum ether. The fractions containing desired product were combined and concentrated to afford tert-butyl 2-(1-(2-cyclopropylpyrimidin-5-yl)ethyl)hydrazinecarboxylate. (ES, m/z): 279.2 [M+H]$^+$.

Step D: To a solution of tert-butyl 2-(1-(2-cyclopropylpyrimidin-5-yl)ethyl)hydrazinecarboxylate (0.50 g, 1.80 mmol) in 1,4-dioxane (8 mL) was added 4 N HCl (13.92 mL, 55.7 mmol) in 1,4-dioxane at room temperature. The resulting solution was stirred for 2 h at room temperature. The reaction mixture was concentrated under vacuum to afford 2-cyclopropyl-5-(1-hydrazinylethyl)pyrimidine dihydrochloride, which was used next step without purification. (ES, m/z): 179.1 [M+H]$^+$.

Step E: To a solution of the 2-cyclopropyl-5-(1-hydrazinylethyl)pyrimidine (0.15 g, 0.60 mmol) in EtOH (6 mL) were added a solution of NaOH (47.8 mg, 1.19 mmol) (in EtOH, 2 mL) and ethene-1,1,2,2-tetracarbonitrile (77 mg, 0.60 mmol) at 0° C. The reaction mixture was stirred at 0° C. for 1 h. The resulting mixture was extracted with ethyl acetate (3×50 mL). The combined organic layer was washed with brine (3×50 mL), dried over anhydrous Na$_2$SO$_4$ and filtered. The filtrate was concentrated under vacuum. The residue was purified by a silica gel column chromatography, eluted with gradient 0%-70% ethyl acetate in petroleum ether. The fractions containing desired product were combined and concentrated to afford 5-amino-1-(1-(2-cyclopropylpyrimidin-5-yl)ethyl)-1H-pyrazole-3,4-dicarbonitrile. (ES, m/z): 280.1 [M+H]$^+$.

Intermediate 22

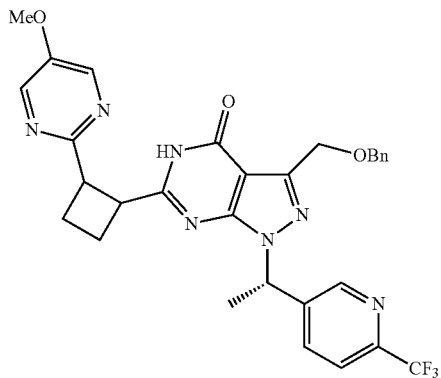 [SMILES: COc1cnc(C2CCC2c2nc3c(c(COCc4ccccc4)nn3[C@@H](C)c3ccc(C(F)(F)F)nc3)c(=O)[nH]2)nc1]

3-((Benzyloxy)methyl)-6-(2-(5-methoxypyrimidin-2-yl)cyclobutyl)-1-((S)-1-(6-(trifluoromethyl)pyridin-3-yl)ethyl)-1H-pyrazolo[3,4-d]pyrimidin-4(5H)-one Step A: To a solution of 1,1,3,3-tetraethoxypropan-2-ol (0.20 g, 0.85 mmol) in THF (5 mL) were added NaH (0.051 g, 1.27 mmol) and MeI (0.079 mL, 1.27 mmol). The reaction mixture was stirred at room temperature for 16 h before being concentrated under vacuum. The residue was diluted with water (10 mL) and extracted with EtOAc (3×15 mL). The combined organic layer was washed with brine (3×10 mL), dried over anhydrous Na$_2$SO$_4$ and filtered. The filtrate was concentrated under vacuum to afford 1,1,3,3-tetraethoxy-2-methoxypropane, which was used directly to next step without further purification.

Step B: To 2-(3-((benzyloxy)methyl)-4-oxo-1-((S)-1-(6-(trifluoromethyl)pyridin-3-yl)ethyl)-4,5-dihydro-1H-pyrazolo[3,4-d]pyrimidin-6-yl)cyclobutanecarboximidamide (0.050 g, 0.095 mmol) was added 1,1,3,3-tetraethoxy-2-methoxypropane (0.24 g, 0.95 mmol). The reaction mixture was stirred at 170° C. for 5 h. The resulting mixture was purified by prep. TLC (EtOAc/Petrol ether=1/1) to afford 3-((benzyloxy)methyl)-6-(2-(5-methoxypyrimidin-2-yl)cyclobutyl)-1-((S)-1-(6-(trifluoromethyl)pyridin-3-yl)ethyl)-1H-pyrazolo[3,4-d]pyrimidin-4(5H)-one. (ES, m/z): 592.2 [M+H]$^+$.

Intermediate 23

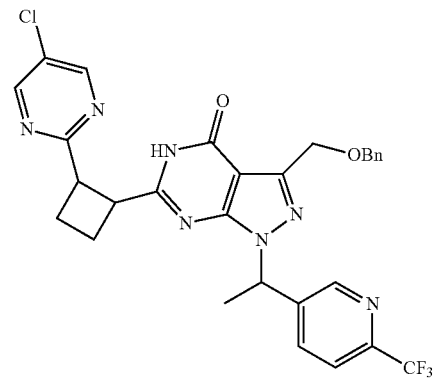 [SMILES: CC(c1ccc(C(F)(F)F)nc1)n1nc(COCc2ccccc2)c2c(=O)[nH]c(C3CCC3c3ncc(Cl)cn3)nc21]

3-((Benzyloxy)methyl)-6-(2-(5-chloropyrimidin-2-yl)cyclobutyl)-1-(1-(6-(trifluoromethyl)pyridin-3-yl)ethyl)-1H-pyrazolo[3,4-d]pyrimidin-4(5H)-one To a solution of 2-(3-((benzyloxy)methyl)-4-oxo-1-(1-(6-(trifluoromethyl)pyridin-3-yl)ethyl)-4,5-dihydro-1H-pyrazolo[3,4-d]pyrimidin-6-yl)cyclobutanecarboximidamide (0.50 g, 0.95 mmol) and 2-chloromalonaldehyde (0.20 g, 1.90 mmol) in AcOH (5 mL) was added sodium acetate (0.23 g, 2.85 mmol) at room temperature. Then the reaction mixture was stirred at 100° C. overnight. After cooling to room temperature, it was concentrated and quenched with sat. NaHCO$_3$ (aq.; 100 mL). The resulting mixture was extracted with EtOAc (3×100 mL). The combined organic layers were washed with brine (3×100 mL), dried over anhydrous Na$_2$SO$_4$, and filtered. The residue was purified by silica gel column chromatography, eluted with gradient 0%-60% EtOAc in petroleum ether. The fractions containing desired product were combined and concentrated to afford 3-((benzyloxy)methyl)-6-(2-(5-chloropyrimidin-2-yl)cyclobutyl)-1-(1-(6-(trifluoromethyl)pyridin-3-yl)ethyl)-1H-pyrazolo[3,4-d]pyrimidin-4(5H)-one. (ES, m/z): 596.2 [M+H]$^+$.

Intermediate 24

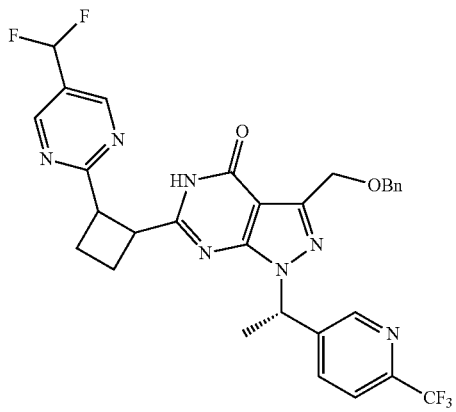 [SMILES: C[C@@H](c1ccc(C(F)(F)F)nc1)n1nc(COCc2ccccc2)c2c(=O)[nH]c(C3CCC3c3ncc(C(F)F)cn3)nc21]

3-((Benzyloxy)methyl)-6-(2-(5-(difluoromethyl)pyrimidin-2-yl)cyclobutyl)-1-((S)-1-(6-(trifluoromethyl)pyridin-3-yl)ethyl)-1H-pyrazolo[3,4-d]pyrimidin-4(5H)-one Step A: To a solution of 2-(3-((benzyloxy)methyl)-4-oxo-1-((S)-1-(6-(trifluoro-methyl)pyridin-3-yl)ethyl)-4,5-dihydro-1H-pyrazolo[3,4-d]pyrimidin-6-yl)cyclobutanecarboximidamide (0.10 g, 0.19 mmol) in MeOH (2 mL) were added sodium methanolate (0.41 g, 0.76 mmol) and [3-(dimethylamino)-2-[(dimethyliminiumyl)methyl]prop-2-en-1-ylidene]dimethyl-azanium diperclorate salt (0.73 g, 0.19 mmol) (prepared by Journal of Heterocyclic Chemistry, 28 (5), 1281-5; 1991) at room temperature under argon atmosphere. The reaction mixture was stirred at 80° C. for 16 h before being concentrated under vacuum. The residue was purified by silica gel column chromatography, eluted with gradient 63% EtOAc in petroleum ether. The fractions containing desired product were combined and concentrated under vacuum to afford 2-(2-(3-((benzyloxy)methyl)-4-oxo-1-((S)-1-(6-(trifluoromethyl)pyridin-3-yl)ethyl)-4,5-dihydro-1H-pyrazolo[3,4-d]pyrimidin-6-yl)cyclobutyl)pyrimidine-5-carbaldehyde. (ES, m/z): 590.2 [M+H]$^+$.

Step B: To a solution of 2-(2-(3-((benzyloxy)methyl)-4-oxo-1-((S)-1-(6-(trifluoro-methyl)pyridin-3-yl)ethyl)-4,5-dihydro-1H-pyrazolo[3,4-d]pyrimidin-6-yl)cyclobutyl)-pyrimidine-5-carbaldehyde (0.05 g, 0.08 mmol) in DCM (1 mL) was added Deoxo-Fluor (0.045 mL, 0.34 mmol) at ice bath under N$_2$. The reaction solution was degassed with N$_2$ for 3 times. The resulting solution was stirred overnight at room temperature under nitrogen. The resulted solution was quenched with MeOH at 0° C. and concentrated under vacuum. The residue was purified by silica gel column chromatography, eluted with gradient 50%-100% EtOAc in petroleum ether. The fractions containing desired product were combined and concentrated under vacuum to afford 3-((benzyloxy)methyl)-6-(2-(5-(difluoromethyl)pyrimidin-2-yl)cyclobutyl)-1-4S)-1-(6-(trifluoro-methyl)pyridin-3-yl)ethyl)-1H-pyrazolo[3,4-d]pyrimidin-4(5H)-one. (ES, m/z): 612.2 [M+H]$^+$.

Intermediate 25

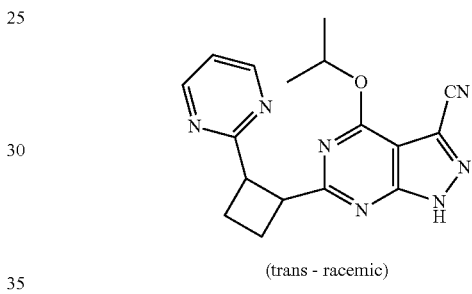

(trans - racemic)

4-Isopropoxy-6-((1S,2S and 1R,2R)-2-(pyrimidin-2-yl)cyclobutyl)-1H-pyrazolo[3,4-d]pyrimidine-3-carbonitrile Step A: Into a 10-L 4-necked round-bottom flask purged and maintained with an inert atmosphere of nitrogen, was placed [(4-methoxyphenyl)methyl]hydrazine dihydrochloride (100 g, 444.22 mmol, 1 equiv), ethanol (4 L), the mixture was cooled to 0° C. This was followed by the addition of a solution of sodium hydroxide (35.5 g, 888.43 mmol, 2 equiv) in ethanol (1.2 L) dropwise with stirring at 0° C. Eth-1-ene-1,1,2,2-tetracarbonitrile (62.6 g, 488.64 mmol, 1.1 equiv) was added. The resulting solution was stirred for 1 h at 0° C. The reaction mixture was quenched with water (1.5 L) and concentrated. The resulting solution was extracted with 3×2 L of ethyl acetate and the organic layers combined. The combined organic layer was washed with 2 L of brine, dried over anhydrous sodium sulfate and concentrated. The residue was first purified by a silica gel column with ethyl acetate/petroleum ether (1:1) then further to remove regioisomeric byproduct by chiral separation (SFC) to give 5-amino-1-[(4-methoxyphenyl)-methyl]-1H-pyrazole-3,4-dicarbonitrile (SFC conditions: EnantioPak-A1-5(02)5*25 cm, 5 um A1-122579-444M31595, MeOH:CO2=40:60). The second peak was the desired compound. The same process was repeated 3 times.

Step B: Into a 250-mL sealed tube purged and maintained with an inert atmosphere of nitrogen, was placed 5-amino-1-[(4-methoxyphenyl)methyl]-1H-pyrazole-3,4-dicarbonitrile (13 g, 51.33 mmol, 1 equiv), (1S,2S and 1R,2R)-2-

(pyrimidin-2-yl)cyclobutane-1-carboxylic acid (10.1 g, 0.06 mmol, 1.1 equiv), dichloroethane (130 mL, 1642.09 mmol, 31.99 equiv), phosphoryl trichloride (39.4 g, 0.26 mmol, 5 equiv). The resulting solution was stirred overnight at 80° C. in sealed tube. The resulting solution was diluted with 500 mL of ethyl acetate and quenched into an ice-cold solution of aqueous sodium hydrogen carbonate (1.3 L). The resulting solution was extracted with 3×1.3 L of ethyl acetate. The combined organic layer was washed with 5 L of brine, dried over anhydrous sodium sulfate and concentrated. The same process was repeated for 4 times and the residue was used to the next step directly.

Step C: Into a 3-L 3-necked round-bottom flask purged and maintained with an inert atmosphere of nitrogen, was placed i-PrOH (38.4 g, 638.99 mmol, 3.000 equiv), THF (920 mL), cooled to 0° C. This was followed by the portionwise addition of sodium hydride (17.0 g, 425.04 mmol, 1.995 equiv, 60%) at 0° C., and stirred the mixture for 0.5 h at 0° C. A solution of 4-chloro-1-[(4-methoxyphenyl)methyl]-6-[(1S,2S and 1R,2R)-2-(pyrimidin-2-yl)cyclobutyl]-1H-pyrazolo[3,4-d]pyrimidine-3-carbonitrile (92 g, 213.02 mmol, 1 equiv) in THF (920 mL) was added dropwise. The resulting solution was stirred for 1 h at 0° C. The reaction was then quenched by the addition of water. The resulting solution was extracted with 3×1.5 L of ethyl acetate, washed with 1×1.5 L of brine. The mixture was dried over anhydrous sodium sulfate and concentrated. The residue was applied onto a silica gel column with ethyl acetate/petroleum ether (1:1) to provide 1-[(4-methoxyphenyl)methyl]-4-(propan-2-yloxy)-6-[(1S,2S and 1R,2R)-2-(pyrimidin-2-yl)cyclobutyl]-1H-pyrazolo[3,4-d]pyrimidine-3-carbonitrile.

Step D: Into a 2-L 3-necked round-bottom flask purged and maintained with an inert atmosphere of nitrogen, was placed 1-[(4-methoxyphenyl)methyl]-4-(propan-2-yloxy)-6-[(1S,2S and 1R,2R)-2-(pyrimidin-2-yl)cyclobutyl]-1H-pyrazolo[3,4-d]pyrimidine-3-carbonitrile (28 g, 61.47 mmol, 1 equiv), ACN (700 mL), H$_2$O (160 mL), followed by an aqueous suspension of CAN (118.4 g, 215.18 mmol, 3.501 equiv) in H$_2$O (64 mL). The resulting solution was stirred for 3 h at room temperature. The reaction was then quenched by the addition of 620 mL of sat.NaHCO$_3$. Extracted with 4×1.5 L of ethyl acetate and the organic layers combined. Washed with 1×1.5 L of sat.NaCl. Dried over K$_2$CO$_3$ and concentrated. The residue was applied onto a silica gel column with ethyl acetate/petroleum ether (2:1). This resulted in 4-(propan-2-yloxy)-6-[(1S,2S and 1R,2R)-2-(pyrimidin-2-yl)cyclobutyl]-1H-pyrazolo[3,4-d]pyrimidine-3-carbonitrile. LCMS: (ES, m/z): 336 [M+H]$^+$; H-NMR: (300 MHz, CDCL$_3$, ppm): 14.43 (1H, s), 8.75-8.74 (2H, d), 7.29-7.20 (1H, t), 5.65 (1H, m), 4.38-4.24 (2H, mm), 2.66-2.48 (4H, m), 1.52-1.49 (6H, t)

Intermediate 26

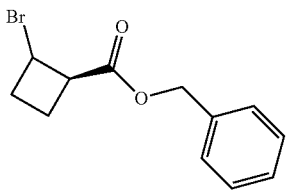 [SMILES: O=C(OCc1ccccc1)[C@H]1CCC1Br]

(1R)-benzyl 2-bromocyclobutanecarboxylate (1R,2S)-2-((benzyloxy)carbonyl)cyclobutanecarboxylic acid (50 g, 213 mmol), 1,3-dibromo-1,3,5-triazinane-2,4,6-trione (77 g, 267 mmol), dichloroethane (1000 ml) were charged into a 2000 ml three-necked bottle under N2. Ag(phen)2OTf (6.59 g, 10.67 mmol) was added. The resulting mixture was stirred at 70° C. for 2 h. Then the reaction mixture was diluted with MTBE, filter, washed with NaHCO3/Na2S2O3, brine, dried over MgSO4, concentrated under vacuum. The residue was purified by silica column (ethyl acetate:petroleum ether 1:50) to give (1R)-benzyl 2-bromocyclo-butane-carboxylate. LC-MS: (ESI, m/z): 291 [M+Na]$^+$.

Intermediates 27 and 28

INTERMEDIATE 27

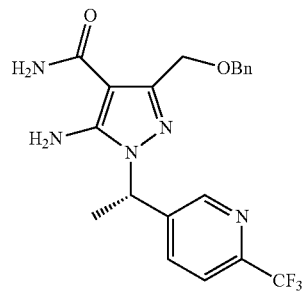

INTERMEDIATE 28

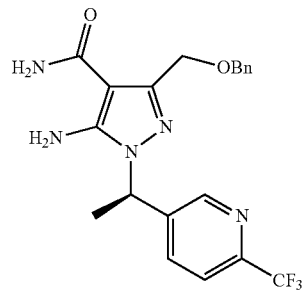

(S)-5-amino-3-((benzyloxy)methyl)-1-(1-(6-(trifluoromethyl)pyridin-3-yl)ethyl)-1H-pyrazole-4-carboxamide (INTERMEDIATE 27) and (R)-5-amino-3-((benzyloxy)methyl)-1-(1-(6-(trifluoromethyl)pyridin-3-yl)ethyl)-1H-pyrazole-4-carboxamide (INTERMEDIATE 28)

5-Amino-3-((benzyloxy)methyl)-1-(1-(6-(trifluoromethyl)pyridin-3-yl)ethyl)-1H-pyrazole-4-carboxamide preparation is described below for EXAMPLES 5-8, Steps A-D. This material was resolved using chiral preparative SFC (AS-H, 21×250 mm column, 40% MeOH co-solvent) to provide peak 1 (INTERMEDIATE 27, stereochemistry determined by VCD), LCMS (ES, m/z): 420.2 [M+H]$^+$ and peak 2 (INTERMEDIATE 28, stereochemistry determined by VCD), LCMS (ES, m/z): 420.2 [M+H]$^+$.

Intermediates 29 and 30

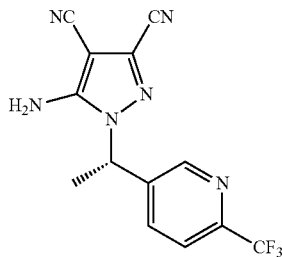

INTERMEDIATE 29

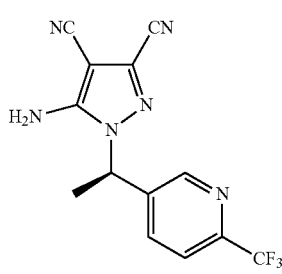

INTERMEDIATE 30

(S)-5-amino-1-(1-(6-(trifluoromethyl)pyridin-3-yl)ethyl)-1H-pyrazole-3,4-dicarbonitrile (INTERMEDIATE 29) and (R)-5-amino-1-(1-(6-(trifluoromethyl)pyridin-3-yl)ethyl)-1H-pyrazole-3,4-dicarbonitrile (INTERMEDIATE 30)

Step A: To a solution of 1-(6-(trifluoromethyl)pyridin-3-yl)ethan-1-one (10 g, 53 mmol), tert-butyl hydrazinecarboxylate (7.7 g, 58 mmol) in EtOH (250 mL) was added AcOH (1.1 g, 17 mmol) at room temperature. The reaction solution was stirred at 80° C. for 2 h. The reaction was concentrated under vacuum to afford tert-butyl 2-(1-(2-chloropyrimidin-5-yl)ethylidene)hydrazinecarboxylate and used directly in the next step.

Step B: To a solution of tert-butyl 2-(1-(6-(trifluoromethyl)pyridin-3-yl)ethylidene)hydrazine-1-carboxylate (15 g, 50 mmol) in AcOH (70 mL) and MeCN (160 ml) was added NaCNBH$_4$ (6.3 g, 100 mmol) at room temperature. The reaction solution was stirred at 80° C. for 1 h. The reaction mixture was concentrated, Et$_2$O (100 ml) added and 1N KOH was added to adjusted pH=13. The aqueous phase was extracted with Et$_2$O (2×100 ml) and the combined organic phase, washed with brine (100 ml), dried over with anhydrous Na$_2$SO$_4$ and filtered. The filtrate was concentrated under vacuum to give crude product of tert-butyl 2-(1-(6-(trifluoromethyl)pyridin-3-yl)ethyl)hydrazine-1-carboxylate which was used without further purification in the next step.

Step C: To a solution of tert-butyl 2-(1-(6-(trifluoromethyl)pyridin-3-yl)ethyl)hydrazine-1-carboxylate (15 g, 49 mmol) was added 4 N HCl in dioxane (75 ml, 300 mmol). The reaction was stirred at room temperature overnight and the solvent removed under vacuum. The residue was slurried in Et$_2$O (75 ml) and filtered to give crude product of 5-(1-hydrazinylethyl)-2-(trifluoromethyl)pyridine HCl salt which was used without further purification in the next step.

Step D: To a solution of 5-(1-hydrazinylethyl)-2-(trifluoromethyl)pyridine HCl salt (9 g, 49 mmol) in EtOH (360 mL) at 0° C. were added a solution of NaOH (2.6 g, 65 mmol) (in EtOH, 108 mL) and ethene-1,1,2,2-tetracarbonitrile (6.3 g, 49 mmol) at 0° C. The reaction mixture was stirred at 0° C. for 1 h, saturated NaHCO$_3$ (135 ml) added and the EtOH removed under vacuum. The resulting mixture was extracted with ethyl acetate (3×90 mL). The combined organic layer was dried over anhydrous Na$_2$SO$_4$ and filtered. The filtrate was concentrated under vacuum. The residue was purified by a silica gel column chromatography, eluted with gradient 25% ethyl acetate in petroleum ether to give 5-Amino-1-(1-(5-(trifluoromethyl)pyrazin-2-yl)ethyl)-1H-pyrazole-3,4-dicarbonitrile. This material was resolved using chiral preparative SFC (AS-H, 21×250 mm column, 20% MeOH co-solvent) to provide peak 1 (INTERMEDIATE 29, stereochemistry determined by VCD), LCMS (ES, m/z): 307.1 [M+H]$^+$ and peak 2 (INTERMEDIATE 30, stereochemistry determined by VCD), LCMS (ES, m/z): 307.1 [M+H]$^+$.

Intermediate 31

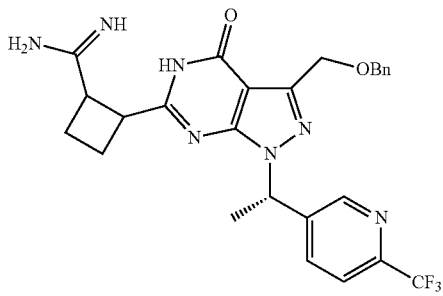 [SMILES: C[C@@H](c1ccc(C(F)(F)F)nc1)n1nc(COCc2ccccc2)c2c(=O)[nH]c(C3CCC3C(=N)N)nc21]

2-(3-((Benzyloxy)methyl)-4-oxo-1-((S)-1-(6-(trifluoromethyl)pyridin-3-yl)ethyl)-4,5-dihydro-1H-pyrazolo[3,4-d]pyrimidin-6-yl)cyclobutanecarboximidamide 2-(3-((Benzyloxy)methyl)-4-oxo-1-((S)-1-(6-(trifluoromethyl)pyridin-3-yl)ethyl)-4,5-dihydro-1H-pyrazolo[3,4-d]pyrimidin-6-yl)cyclobutanecarboximidamide (INTERMEDIATE 31) was prepared from (S)-5-amino-3-((benzyloxy)methyl)-1-(1-(6-(trifluoromethyl)pyridin-3-yl)ethyl)-1H-pyrazole-4-carboxamide (INTERMEDIATE 27) using procedures described for EXAMPLES 5-8, steps E and F, (ES, m/z): 526.2 [M+H]$^+$.

Intermediates 32 AND 33

INTERMEDIATE 32

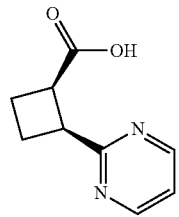

Cis-racemic

-continued

INTERMEDIATE 33

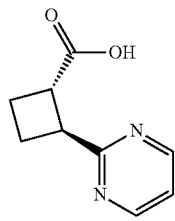

Trans-racemic (1R,2S and 1S,2R)-2-(pyrimidin-2-yl)cyclobutane-1-carboxylic acid (INTERMEDIATE 32) and (1S, 2S and 1R,2R)-2-(pyrimidin-2-yl)cyclobutane-1-carboxylic acid (INTERMEDIATE 33)

2-(Pyrimidin-2-yl)cyclobutane-1-carboxylic acid was prepared as described herein (see INTERMEDIATE 2). This mixture was separated by silica gel column chromatography eluting with ethyl acetate:MeOH (10:1 to 3:1) to provide peak 1 and peak 2. Peak 1 was further purified by precipitating from acetonitrile at 10-15° C. to provide INTERMEDIATE 32. LCMS (ES, m/z): 179.1 [M+H]+. Peak 2 was further purified by prep HPLC [Phenomenex Luna (2) C-18, 250×50 mm; 5% to 25% MeCN in water (0.09% TFA)] to provide INTERMEDIATE 33. LCMS (ES, m/z): 179.1 [M+H]+.

Examples 1-4

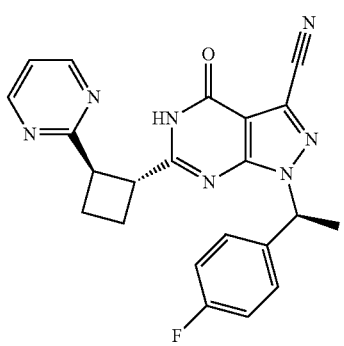

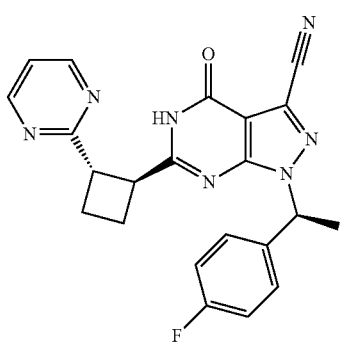

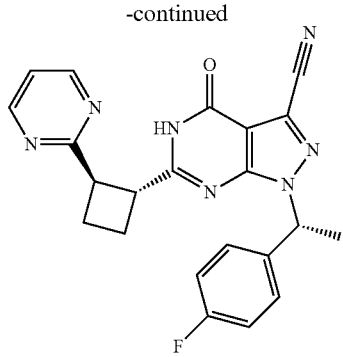

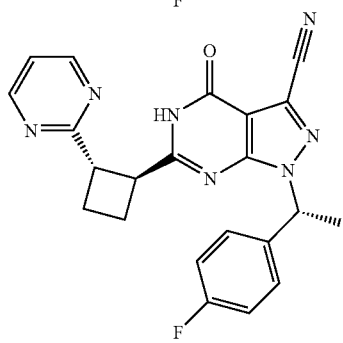

1-(1-(4-Fluorophenyl)ethyl)-4-oxo-6-((1,2-trans)-2-(pyrimidin-2-yl)cyclobutyl)-4,5-dihydro-1H-pyrazolo[3,4-d]pyrimidine-3-carbonitrile Step A: (E)-tert-Butyl 2-(1-(4-fluorophenyl)ethylidene)hydrazinecarboxylate. A round bottom flask (2 L) was charged with 1-(4-fluorophenyl)ethanone (50 g, 362 mmol) in Ethanol (1 L), followed by the addition of tert-butyl hydrazinecarboxylate (52.6 g, 398 mmol) and acetic acid (7.61 g, 127 mmol) and the contents were stirred at 90° C. for 4 h. After which, the reaction mixture was cooled to room temperature and concentrated under reduced pressure to get the crude which was washed with petroleum ether (2×50 mL) to afford the title compound which was used without further purification. $^1$H NMR (400 MHz, DMSO-$d_6$) δ 9.84 (s, 1H), 7.79-7.75 (m, 2H), 7.24-7.19 (m, 2H), 2.19 (s, 3H), 1.48 (s, 9H). LCMS (ES, m/z): 197 [M+H]+.

Step B: tert-Butyl 2-(1-(4-fluorophenyl)ethyl)hydrazinecarboxylate. To a solution of (E)-tert-butyl 2-(1-(4-fluorophenyl)ethylidene)hydrazinecarboxylate (85 g, 337 mmol) in Acetonitrile (850 mL), was added acetic acid (77 mL, 1348 mmol) and sodium cyanoborohydride (52.9 g, 842 mmol) sequentially and the contents were stirred at 80° C. for 2.5 h. The reaction mixture was then concentrated, water (400 mL) and 10% sodium hydroxide solution (150 mL) were added sequentially and reaction mixture was extracted with ethyl acetate (3×200 mL). The combined organic layers were washed with brine (300 mL), dried over anhydrous sodium sulfate, filtered and concentrated under reduced pressure. The residue was purified by column chromatography (silica gel 230-400 mesh, 5-10% Ethyl acetate/Hexane) to afford the title compound. $^1$H NMR (400 MHz, DMSO-$d_6$) δ 8.15 (s, 1H), 7.37-7.33 (m, 2H), 7.14-7.08 (m, 2H), 4.61 (s, 1H), 4.09 (d, J=7.60 Hz, 1H), 1.35 (s, 9H), 1.16 (d, J=8.80 Hz, 3H). LCMS (ES, m/z): 199 [M+H]+.

Step C: (1-(4-Fluorophenyl)ethyl)hydrazine dihydrochloride. A round bottom flask (1 L) containing a solution of tert-butyl 2-(1-(4-fluorophenyl)ethyl)hydrazinecarboxylate (71 g, 279 mmol) in dichloromethane (200 mL), was cooled to 0° C. and a solution of HCl in Dioxane (400 mL, 1600 mmol) was added and the contents were stirred at ambient temperature for 18 h. The reaction mixture was concentrated under reduced pressure to get the crude which was washed with diethyl ether (2×50 mL) to afford the title compound. $^1$H NMR (400 MHz, DMSO-d$_6$) δ 8.01-7.89 (m, 3H), 7.53-7.48 (m, 2H), 7.23-7.17 (m, 2H), 4.25 (q, J=8.80 Hz, 1H), 1.40 (d, J=8.80 Hz, 3H). LCMS (ES, m/z): 155 [M+H]$^+$.

Step D: 5-Amino-3-((benzyloxy)methyl)-1-(1-(4-fluorophenyl)ethyl)-1H-pyrazole-4-carbonitrile. To a pre-cooled solution of (1-(4-fluorophenyl)ethyl)hydrazine dihydrochloride (10 g, 44.0 mmol) in ethanol (100 mL) at 0° C. was added sodium methoxide (5.00 g, 92 mmol) and 2-(2-(benzyloxy)-1-methoxyethylidene)malononitrile (11.06 g, 48.4 mmol) sequentially and the contents were stirred at ambient temperature for 4 h. The reaction mixture was concentrated under reduced pressure, water (100 mL) was added and the mixture extracted with ethyl acetate (2×100 mL). The combined organic layers were washed with brine (100 mL), dried over anhydrous sodium sulfate, filtered and concentrated under reduced pressure. The residue was purified by column chromatography (silica gel 230-400 mesh, 20-25% Ethyl acetate/Hexane) to afford the title compound. $^1$H NMR (400 MHz, DMSO-d$_6$) δ 7.34-7.27 (m, 7H), 7.16 (t, J=12.00 Hz, 2H), 6.72 (br s, 2H), 5.54-5.52 (m, 1H), 4.49 (s, 2H), 4.37 (s, 2H), 1.68 (d, J=8.80 Hz, 3H). LCMS (ES, m/z): 351 [M+H]$^+$.

Step E: 5-Amino-3-((benzyloxy)methyl)-1-(1-(4-fluorophenyl)ethyl)-1H-pyrazole-4-carboxamide. To a solution of 5-amino-3-((benzyloxy)methyl)-1-(1-(4-fluorophenyl) ethyl)-1H-pyrazole-4-carbonitrile (10 g, 28.5 mmol) in DMSO (150.0 mL) cooled to 0° C. was added potassium carbonate (19.72 g, 143 mmol) and hydrogen peroxide (14.58 mL, 143 mmol) and the contents were stirred at ambient temperature for 10 h. The reaction mixture was cooled to 0° C. and potassium carbonate (19.72 g, 143 mmol) and hydrogen peroxide (14.58 mL, 143 mmol) were added and the contents were stirred at ambient temperature for 10 h. This cycle was repeated once more and the reaction was quenched with saturated sodium thiosulfate (100 mL) solution and extracted with ethyl acetate (2×100 mL). The combined organic layers were washed with brine (100 mL), dried over anhydrous sodium sulfate, filtered and concentrated under reduced pressure. The residue was purified by column chromatography (silica gel 230-400 mesh, 30-35% Ethyl acetate/Hexane) to afford the title compound. $^1$H NMR (400 MHz, DMSO-d$_6$) δ 7.39-7.26 (m, 7H), 7.15 (t, J=11.60 Hz, 2H), 6.92 (br s, 2H), 6.43 (br s, 2H), 5.54-5.49 (m, 1H), 4.54 (s, 2H), 4.50 (s, 2H), 1.70 (d, J=9.20 Hz, 3H). LCMS (ES, m/z): 369 [M+H]$^+$.

Step F: (1,2-trans)-2-(3-((Benzyloxy)methyl)-1-(1-(4-fluorophenyl)ethyl)-4-oxo-4,5-dihydro-1H-pyrazolo[3,4-d] pyrimidin-6-yl)cyclobutanecarbonitrile. A Sealed tube (100 mL) was charged with 5-amino-3-((benzyloxy)methyl)-1-(1-(4-fluorophenyl)ethyl)-1H-pyrazole-4-carboxamide (5 g, 13.57 mmol) in anhydrous ethanol (50.0 mL) and 60% dispersion of sodium hydride (1.628 g, 40.7 mmol) was added at 0° C. and the contents were stirred at room temperature for 1 h. Then (1,2-trans)-cyclobutane-1,2-dicarbonitrile (4.32 g, 40.7 mmol) was added. The mixture was stirred at 140° C. for 18 h, cooled to ambient temperature concentrated under reduced pressure, quenched with ice water and extracted with dichloromethane (2×100 ml). The combined organic layers were washed with brine (100 mL), dried over anhydrous sodium sulfate, filtered and concentrated under reduced pressure. The residue was purified by column chromatography (silica gel 230-400 mesh, 25-30% Ethyl acetate/Hexane) to afford the title compound. $^1$H NMR (400 MHz, DMSO-d$_6$) δ 12.21 (s, 1H), 7.45 (q, J=6.40 Hz, 2H), 7.35-7.26 (m, 5H), 7.19-7.13 (m, 2H), 6.11-6.06 (m, 1H), 4.84 (s, 2H), 4.56 (s, 2H), 3.87-3.80 (m, 2H), 2.33-2.26 (m, 4H), 1.89 (d, J=7.20 Hz, 3H). LCMS (ES, m/z): 458 [M+H]$^+$.

Step G: (1,2-trans)-2-(3-((Benzyloxy)methyl)-1-(1-(4-fluorophenyl)ethyl)-4-oxo-4,5-dihydro-1H-pyrazolo[3,4-d] pyrimidin-6-yl)cyclobutanecarboximidamide. To a mixture of dry ethanol (30 mL) and chloroform (30 mL) cooled at 0° C., was added acetyl chloride (14.51 mL, 203 mmol) slowly and mixture left under stirring for 20 min at 0° C. Then a solution of (1,2-trans)-2-(3-((benzyloxy)methyl)-1-(1-(4-fluorophenyl)ethyl)-4-oxo-4,5-dihydro-1H-pyrazolo[3,4-d] pyrimidin-6-yl)cyclobutanecarbonitrile (3.1 g, 6.78 mmol) in dry chloroform (30 mL) was added drop wise and the mixture stirred at ambient temperature for 18 h. The volatile's were evaporated under reduced pressure, the residue re-dissolved in dry ethanol (30 mL) and ammonia in methanol (48.4 mL, 6.78 mmol) was added. The mixture was stirred at ambient temperature for 24 h and the solvent evaporated under reduced pressure to obtained the title compound. $^1$H NMR (400 MHz, DMSO-d$_6$) δ 8.84 (s, 1H), 7.51-7.42 (m, 2H), 7.33-7.20 (m, 7H), 7.18-7.01 (m, 3H), 6.13-6.05 (m, 1H), 4.70 (s, 2H), 4.56 (s, 2H), 3.82-3.61 (m, 2H), 3.47-3.40 (m, 1H), 2.37-2.04 (m, 3H), 1.87 (d, J=9.20 Hz, 3H). LCMS (ES, m/z): 475 [M+H]$^+$.

Step H: 3-((Benzyloxy)methyl)-1-(1-(4-fluorophenyl) ethyl)-6-((1,2-trans)-2-(pyrimidin-2-yl)cyclobutyl)-1H-pyrazolo[3,4-d]pyrimidin-4(5H)-one. A sealed tube (50 mL) was charged with (1,2-trans)-2-(3-((benzyloxy)methyl)-1-(1-(4-fluorophenyl)ethyl)-4-oxo-4,5-dihydro-1H-pyrazolo [3,4-c]pyrimidin-6-yl)cyclobutanecarboximidamide (3.3 g, 6.95 mmol) and 1,1,3,3-tetramethoxypropane (14.0 mL, 6.95 mmol). The reaction mixture was stirred at 175° C. for 16 h, cooled to ambient temperature and the solvent concentrated under reduced pressure. The residue was treated with dichloromethane (50 mL) and the resulting mixture stirred for 10 min. The mixture was filtered and the resulting solution was concentrated under reduced pressure and purified by column chromatography (silica gel 230-400 mesh, 60-80% Ethyl acetate/Hexane) to afford the title compound. $^1$H NMR (400 MHz, DMSO-d$_6$) δ 12.07 (s, 1H), 8.81-8.78 (m, 2H), 7.44-7.40 (m, 3H), 7.40-7.26 (m, 5H), 7.17-7.08 (m, 2H), 6.06-6.03 (m, 1H), 4.70 (s, 2H), 4.56 (s, 2H), 4.27-4.22 (m, 1H), 3.88-3.86 (m, 1H), 2.32-2.26 (m, 4H), 1.88 (d, J=8.00 Hz, 3H). LCMS (ES, m/z): 511 [M+H]$^+$.

Step I: 1-(1-(4-Fluorophenyl)ethyl)-3-(hydroxymethyl)-6-((1,2-trans)-2-(pyrimidin-2-yl)cyclobutyl)-1H-pyrazolo [3,4-d]pyrimidin-4(5H)-one. A round bottom flask (100 mL) containing a solution of 3-((benzyloxy)methyl)-1-(1-(4-fluorophenyl)ethyl)-6-((1,2-trans)-2-(pyrimidin-2-yl)cyclobutyl)-1H-pyrazolo[3,4-d]pyrimidin-4(5H)-one (1.1 g, 2.154 mmol) in dichloromethane (20 mL) was cooled to −78° C. and boron trichloride (8.62 mL, 8.62 mmol) was added and the contents were stirred at 0° C. for 30 mins. The reaction mixture was cooled to −−78° C. and methanol (15.0 mL) added. The reaction was warmed to 0° C. and neutralized to pH 7 with ammonium hydroxide, diluted with dichloromethane, the layers separated and the organic layer dried over sodium sulfate, filtered and evaporated under reduced pressure to give the title compound. $^1$H NMR (400 MHz, DMSO-d$_6$) δ 8.81-8.78 (m, 2H), 7.45-7.34 (m, 3H), 7.17-7.10 (m, 2H), 6.04-6.01 (m, 1H), 5.15 (br s, 1H), 4.64

(d, J=4.80 Hz, 2H), 4.26-4.23 (m, 1H), 3.89-3.86 (m, 1H), 2.33-2.31 (m, 4H), 1.81 (d, J=8.00 Hz, 3H). LCMS (ES, m/z): 421 [M+H]$^+$.

Step J: 1-(1-(4-Fluorophenyl)ethyl)-4-oxo-6-((1,2-trans)-2-(pyrimidin-2-yl)cyclobutyl)-4,5-dihydro-1H-pyrazolo[3,4-d]pyrimidine-3-carbaldehyde. To a solution of 1-(1-(4-fluorophenyl)ethyl)-3-(hydroxymethyl)-6-((1,2-trans)-2-(pyrimidin-2-yl)cyclobutyl)-1H-pyrazolo[3,4-d]pyrimidin-4(5H)-one (1 g, 2.378 mmol) in dichloromethane (20 mL) was added Dess-Martin periodinane (1.211 g, 2.85 mmol) at ambient temperature and the contents were stirred for 30 mins. The reaction mixture was diluted with dichloromethane and quenched with saturated aqueous sodium bicarbonate and sodium thiosulfate solutions. The resulting mixture was stirred for an additional 30 mins. The organic layer was separated and dried over sodium sulfate, filtered and evaporated to give the title compound. $^1$H NMR (400 MHz, DMSO-d$_6$) δ 10.15 (s, 1H), 8.80-8.78 (m, 2H), 7.46-7.34 (m, 3H), 7.17-7.11 (m, 2H), 6.04-6.01 (m, 1H), 4.33-4.18 (m, 1H), 3.95-3.70 (m, 1H), 2.34-2.30 (m, 4H), 1.93 (d, J=8.00 Hz, 3H). LCMS (ES, m/z): 419 [M+H]$^+$.

Step K: 1-(1-(4-Fluorophenyl)ethyl)-4-oxo-6-((1,2-trans)-2-(pyrimidin-2-yl)cyclobutyl)-4,5-dihydro-1H-pyrazolo[3,4-d]pyrimidine-3-carbonitrile. A round bottom flask (100 mL) containing 1-(1-(4-fluorophenyl)ethyl)-4-oxo-6-((1,2-trans)-2-(pyrimidin-2-yl)cyclobutyl)-4,5-dihydro-1H-pyrazolo[3,4-d]pyrimidine-3-carbaldehyde (1 g, 2.390 mmol) in acetonitrile (20.0 mL) was treated with hydroxylamine hydrochloride (0.249 g, 3.58 mmol) and DIPEA (1.252 mL, 7.17 mmol). A 50% solution of propylphosphonic anhydride (3.80 g, 5.97 mmol) was added drop wise to the mixture and the resulting solution was heated at 80° C. for 16 h. The reaction mixture was cooled, evaporated in vacuo and quenched with saturated aqueous sodium bicarbonate solution, extracted with dichloromethane (2×25 mL), dried over anhydrous sodium sulfate, filtered and evaporated in vacuo. The residue was purified by column chromatography (silica gel 230-400 mesh, 80-100% Ethyl acetate/Hexane) to obtain the title compound as a mixture of four isomers. The isomers were separated by chiral SFC HPLC purification (20 mM ammonia in methanol, column: Lux C3, Flow: 3 mL) to yield the first eluting isomer, peak 1 as Example 1: $^1$H NMR (400 MHz, DMSO-d$_6$) δ 12.55 (s, 1H), 8.80 (d, J=4.80 Hz, 2H), 7.46 (q, J=5.60 Hz, 3H), 7.17 (t, J=8.80 Hz, 2H), 6.16-6.14 (m, 1H), 4.25-4.23 (m, 1H), 3.93-3.91 (m, 1H), 2.33-2.28 (m, 4H), 1.89 (d, J=6.80 Hz, 3H), LCMS (ES, m/z): 416 [M+H]$^+$, Chiral Purity: t$_R$: 3.06 (100% Pure); the second eluting isomer, peak 2 as Example 2: $^1$H NMR (400 MHz, DMSO-d$_6$) δ 12.46 (s, 1H), 8.79 (d, J=4.80 Hz, 2H), 7.45-7.38 (m, 3H), 7.14-7.09 (m, 2H), 6.17-6.15 (m, 1H), 4.28-4.26 (m, 1H), 3.94-3.89 (m, 1H), 2.33-2.31 (m, 4H), 1.89 (d, J=6.80 Hz, 3H). LCMS (ES, m/z): 416 [M+H]$^+$, Chiral Purity: t$_R$: 3.52 (99.12% Pure); the third eluting isomer, peak 3 as Example 3: $^1$H NMR (400 MHz, DMSO-d$_6$) δ 12.58 (s, 1H), 8.83-8.78 (m, 2H), 7.45-7.38 (m, 3H), 7.13-7.09 (m, 2H), 6.17 (q, J=7.20 Hz, 1H), 4.28-4.26 (m, 1H), 3.92-3.90 (m, 1H), 2.33-2.31 (m, 4H), 1.89 (d, J=7.20 Hz, 3H), LCMS (ES, m/z): 416 [M+H]$^+$, Chiral Purity: t$_R$: 4.83 (97.57% Pure); the fourth eluting isomer, peak 4 as Example 4: $^1$H NMR (400 MHz, DMSO-d$_6$) δ 12.57 (s, 1H), 8.80 (d, J=4.80 Hz, 2H), 7.48-7.45 (m, 2H), 7.40 (t, J=4.80 Hz, 1H), 7.20-7.16 (m, 2H), 6.16-6.14 (m, 1H), 4.25-4.23 (m, 1H), 3.93-3.91 (m, 1H), 2.33-2.28 (m, 4H), 1.90 (d, J=7.20 Hz, 2H), LCMS (ES, m/z): 416 [M+H]$^+$, Chiral Purity: t$_R$: 6.39 (97.82% Pure).

Examples 5-8

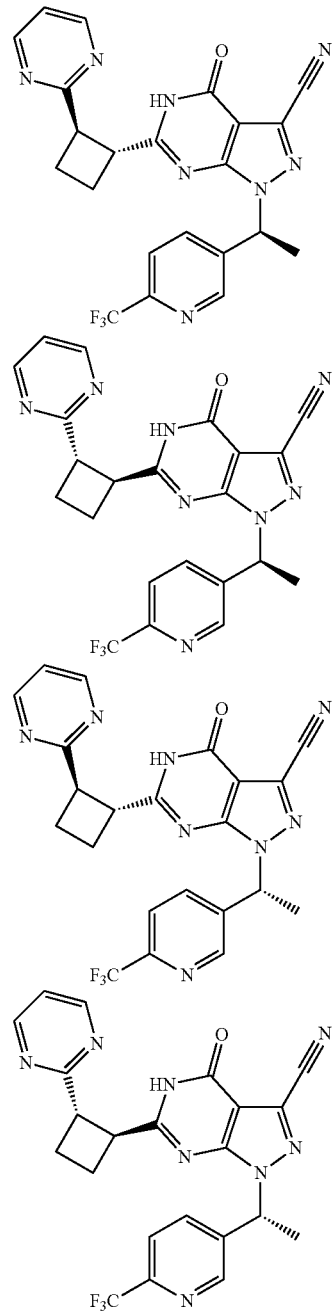

4-Oxo-6-((1,2-trans)-2-(pyrimidin-2-yl)cyclobutyl)-1-(1-(6-(trifluoromethyl)pyridin-3-yl)ethyl)-4,5-dihydro-1H-pyrazolo[3,4-d]pyrimidine-3-carbonitrile Step A: tert-Butyl 2-(1-(6-(trifluoromethyl)pyridin-3-yl)ethyl)hydrazinecarboxylate. Acetic acid (1.589 ml, 27.8 mmol) was added to a stirred mixture of tert-butyl carbazate (11.53 g, 87 mmol) and 1-(6-(trifluoromethyl)pyridine-3-yl)ethanone (15 g, 79 mmol) in ethanol (375 ml) at ambient temperature and the mixture was stirred at 80° C. for 2 h.

The solvent was removed under reduced pressure and acetonitrile (375 ml) and acetic acid (18.16 ml, 317 mmol) were added at ambient temperature followed by sodium cyanoborohydride (9.97 g, 159 mmol). The reaction was heated at 80° C. and after 48 hours at the solvent was removed under vacuum. The crude residue was dissolved in $Et_2O/H_2O$ (150:50 ml) and pH brought to 13 by carefully adding solid KOH. The organic layer was separated, washed with brine (1×100 mL) dried over $Na_2SO_4$ and concentrated under reduced pressure to afford the title compound. LCMS (ES, m/z): 305 $[M+H]^+$.

Step B: 5-(1-Hydrazinylethyl)-2-(trifluoromethyl)pyridine dihydrochloride. Tert-butyl 2-(1-(6-(trifluoromethyl)pyridin-3-yl)ethyl)hydrazine carboxylate (30 g, 63.9 mmol) was dissolved in dioxane (150 ml) and hydrogen chloride (192 ml, 766 mmol) was added. After 48 h a white precipitate formed and the mixture was concentrated under reduced pressure to afford the title compound. LCMS (ES, m/z): 205 $[M+H]^+$.

Step C: 5-Amino-3-((benzyloxy)methyl)-1-(1-(6-(trifluoromethyl)pyridin-3-yl)ethyl)-1H-pyrazole-4-carbonitrile. To a stirred, 0° C. solution of 5-(1-hydrazinylethyl)-2-(trifluoromethyl)pyridine dihydrochloride (20 g, 71.9 mmol) and 2-(2-(benzyloxy)-1-methoxyethylidene)malononitrile (19.7 g, 86 mmol) in methanol (25 ml) was added sodium methoxide solution (0.5M, 302 ml, 151 mmol). The ice bath was removed and the solution was allowed to stir at ambient temperature for 30 minutes. The solvent was removed under vacuum and the crude reaction mixture was diluted with 150 mL water and 500 mL ethyl acetate. The organic layer was separated and the aqueous phase was extracted with ethyl acetate (1×150 mL). The combined organic layers were dried over $Na_2SO_4$ and concentrated under vacuum. The crude was purified by silica gel chromatography (10-40% EtOAc in hexanes) to afford the title compound. LCMS (ES, m/z): 402.2 $[M+H]^+$.

Step D: 5-Amino-3-((benzyloxy)methyl)-1-(1-(6-(trifluoromethyl)pyridin-3-yl)ethyl)-1H-pyrazole-4-carboxamide. To 5-amino-3-((benzyloxy)methyl)-1-(1-(6-(trifluoromethyl)pyridin-3-yl)ethyl)-1H-pyrazole-4-carbonitrile (25.4 g, 63.3 mmol) in EtOH (90 ml) was added 30% aqueous hydrogen peroxide (32.6 ml, 316 mmol) solution followed by addition of ammonium hydroxide (85 ml, 633 mmol) at 0° C. The ice bath was removed and the solution was stirred at ambient temperature for 48 h. The reaction mixture was cooled to 0° C., slowly quenched with enough (~3 eq.) saturated aqueous sodium thiosulfate solution to quench the peroxide The solvent was removed under vacuum and to the crude residue was added 200 mL water, and extracted with ethyl acetate (2×250 mL). The combined orgainc layers were dried over $Na_2SO_4$, filtered and evaporated under vacuum to afford the title compound. LCMS (ES, m/z): 420.4 $[M+H]^+$.

Step E: (1,2-trans)-2-(3-((Benzyloxy)methyl)-4-oxo-1-(1-(6-(trifluoromethyl)pyridin-3-yl)ethyl)-4,5-dihydro-1H-pyrazolo[3,4-d]pyrimidin-6-yl)cyclobutanecarbonitrile. To a solution of 5-amino-3-((benzyloxy)methyl)-1-(1-(6-(trifluoromethyl)pyridin-3-yl)ethyl)-1H-pyrazole-4-carboxamide (22 g, 52.5 mmol) in EtOH (15 ml) was added 60% dispersion of sodium hydride (6.29 g, 157 mmol) under $N_2$ at ambient temperature. The reaction mixture was stirred at ambient temperature for 1 h and (1,2-trans)-cyclobutane-1,2-dicarbonitrile (16.70 g, 157 mmol) was added. The mixture was separated into 4 batches and microwaved at 150° C. for 30 minutes each. The reactions were combined, the solvent was removed under vacuum and the residue was diluted with 250 mL water and extracted with EtOAc (2×250 mL). The combined EtOAc layers were dried over $Na_2SO_4$, concentrated under vacuum and the residue purified by silica gel chromatography (30-50% EtOAc in hexanes) to yield the title compound. LCMS (ES, m/z): 509.4 $[M+H]^+$.

Step F: (1,2-trans)-2-(3-((Benzyloxy)methyl)-4-oxo-1-(1-(6-(trifluoromethyl)pyridin-3-yl)ethyl)-4,5-dihydro-1H-pyrazolo[3,4-d]pyrimidin-6-yl)cyclobutanecarboximidamide. A mixture of $CHCl_3$ (44.2 ml) and ethanol (44.2 ml) were cooled to 0° C. Acetyl chloride (14.47 ml, 204 mmol) was added drop wise to the solvent mixture and stirred at 0° C. for 20 minutes. (1,2-trans)-2-(3-((Benzyloxy)methyl)-4-oxo-1-(1-(6-(trifluoromethyl)pyridin-3-yl)ethyl)-4,5-dihydro-1H-pyrazolo[3,4-d]pyrimidin-6-yl)cyclobutanecarbonitrile (5 g, 8.85 mmol) in 35 mL $CHCl_3$ was added at 0° C. drop wise to the reaction mixture. After 48 hrs at ambient temperature the solvent removed under vacuum and the residue was dissolved in 25 mL EtOH and 25 mL 7 M solution of ammonia in MeOH was added. After 48 h the solvent was removed under reduced pressure to afford the title compound. LCMS (ES, m/z): 526.2 $[M+H]^+$.

Step G: 3-((Benzyloxy)methyl)-6-((1,2-trans)-2-(pyrimidin-2-yl)cyclobutyl)-1-(1-(6(trifluoromethyl)pyridin-3-yl)ethyl)-1H-pyrazolo[3,4-d]pyrimidin-4(5H)-one. To (1,2-trans)-2-(3-((benzyloxy)methyl)-4-oxo-1-(1-(6-(trifluoromethyl)pyridin-3-yl)ethyl)-4,5-dihydro-1H-pyrazolo[3,4-d]pyrimidin-6-yl)cyclobutanecarboximidamide (2.5 g, 1.665 mmol) in 1,1,3,3-tetramethoxypropane (10 ml, 60.7 mmol) was microwaved at 150° C. for 0.5 h as 3 separate batches. The solvent was removed under reduced pressure and the residue purified by silica gel chromatography (30-60% EtOAc in hexanes) to yield the title compound. LCMS (ES, m/z): 562.1 $[M+H]^+$.

Step H: 3-(Hydroxymethyl)-6-((1,2-trans)-2-(pyrimidin-2-yl)cyclobutyl)-1-(1-(6-(trifluoromethyl)pyridin-3-yl)ethyl)-1H-pyrazolo[3,4-d]pyrimidin-4(5H)-one. To 3-((benzyloxy)methyl)-6-((1,2-trans-rac)-2-(pyrimidin-2-yl)cyclobutyl)-1-(1-(6-(trifluoromethyl)pyridin-3-yl)ethyl)-1H-pyrazolo[3,4-d]pyrimidin-4(5H)-one (3.7 g, 6.59 mmol) in DCM (65.9 ml) at −78° C. was added trichloroborane (26.4 ml, 26.4 mmol). The solution was warmed to 0° C. and stirred at 0° C. for 15 minutes. The reaction was cooled to −78° C. and 2 mL MeOH was added, followed by warming to 0° C. and neutralizing to pH 7 with aq $NH_4OH$ solution, filtered, dried over $Na_2SO_4$ and the solvent was removed under vacuum to afford the title compound. LCMS (ES, m/z): 472.2 $[M+H]^+$.

Step I: 4-Oxo-6-((1,2-trans)-2-(pyrimidin-2-yl)cyclobutyl)-1-(1-(6-(trifluoromethyl)pyridin-3-yl)ethyl)-4,5-dihydro-1H-pyrazolo[3,4-d]pyrimidine-3-carbaldehyde. To 3-(hydroxymethyl)-6-((1,2-trans)-2-(pyrimidin-2-yl)cyclobutyl)-1-(1-(6-(trifluoromethyl)pyridin-3-yl)ethyl)-1H-pyrazolo[3,4-d]pyrimidin-4(5H)-one (3.8 g, 6.45 mmol) in DCM (215 ml) at ambient temperature was added Dess-Martin periodinane (2.74 g, 6.45 mmol). After 10 minutes the reaction was diluted with 25 mL DCM and quenched with 5 mL aq sat $NaHCO_3$ and 5 mL aq sat $Na_2S_2O_3$ solutions and the mixture stirred at ambient temperature for 30 minutes. The two layers were separated and the aqueous layer was extracted with 2×25 mL DCM. The combined DCM fractions were dried over $Na_2SO_4$ and concentrated in vacuuo. The residue was purified by silica gel chromatography (2-5% MeOH:DCM) to yield the title compound. LCMS (ES, m/z): 470.4 $[M+H]^+$.

Step J: 4-Oxo-6-((1,2-trans)-2-(pyrimidin-2-yl)cyclobutyl)-1-(1-(6-(trifluoromethyl)pyridin-3-yl)ethyl)-4,5-dihydro-1H-pyrazolo[3,4-d]pyrimidine-3-carbonitrile. To 4-oxo-6-((1,2-trans)-2-(pyrimidin-2-yl)cyclobutyl)-1-(1-(6-(trifluoromethyl)pyridin-3-yl)ethyl)-4,5-dihydro-1H-pyrazolo[3,4-d]pyrimidine-3-carbaldehyde (2.7 g, 5.75 mmol) in acetonitrile (57.5 ml) at ambient temperature under N₂ was added hydroxylamine hydrochloride (0.600 g, 8.63 mmol) followed by drop wise addition of N-ethyl-N-isopropylpropan-2-amine (2.004 ml, 11.50 mmol). The reaction was stirred at ambient temperature for 5 min then 50% solution of 2,4,6-tripropyl-1,3,5,2,4,6-trioxatriphosphinane 2,4,6-trioxide (6.85 ml, 11.50 mmol) was added drop wise to the reaction mixture. The reaction mixture was heated at 80° C. for 4 hrs. The solvent was removed under reduced pressure and the crude residue was purified by silica gel chromatography (2-5% MeOH:DCM) to yield the title compound as a mixture of four isomers. Separation of the isomers was done by chiral SFC (OJ-H, 50×250 mm column; 35% MeOH; 2.5 mL injection volume; 210 nm UV detection; 1.6 g in 100 mL MeOH/ACN 1:1 concentration) to afford four isomers. First eluting, peak 1 as Example 5: ¹H NMR (CDCl3) δ (ppm): 2.08 (d, 3H), 2.32 (q, t, 1H), 2.54 (m, 2H), 2.73 (m, 1H), 3.77 (q, 1H), 3.96 (q, 1H), 6.27 (q, 1H), 7.33 (t, 1H), 7.71 (d, 1H), 8.01 (d, d, 1H), 8.84 (t, 3H), 12.33 (s, 1H). LCMS (ES, m/z): 467.2 [M+H]⁺. Second eluting, peak 2 as Example 6: ¹H NMR (CDCl3) δ (ppm): 2.07 (d, 3H), 2.35 (m, 1H), 2.53 (m, 2H), 2.66 (d, q, 1H), 3.80 (d, t, 1H), 3.93 (q, 1H), 6.27 (q, 1H), 7.33 (t, d 1H), 7.74 (d, d 1H), 8.06 (d, d, 1H), 8.87 (d, d, 3H), 12.38 (s, 1H). LCMS (ES, m/z): 467.2 [M+H]⁺. Third eluting, peak 3 as Example 7: ¹H NMR (CDCl3) δ (ppm): 2.07 (d, 3H), 2.35 (q, d, 1H), 2.53 (d, t, 1H), 2.66 (d, 1H), 3.80 (q, 1H), 3.92 (q, 1H), 6.27 (q, 1H), 7.33 (s, 1H), 7.74 (d 1H), 8.06 (d, d, 1H), 8.87 (d, d, 3H), 12.38 (s, 1H). LCMS (ES, m/z): 467.2 [M+H]⁺. Fourth eluting, peak 4 as Example 8: ¹H NMR (CDCl3) δ (ppm): 2.07 (d, 3H), 2.33 (q, 1H), 2.55 (d, d, 2H), 2.72 (q, 1H), 3.77 (q, 1H), 3.96 (q, 1H), 6.27 (q, 1H), 7.30 (m, 1H), 7.72 (d, 1H), 8.01 (d, 1H), 8.85 (d, 3H), 12.32 (s, 1H). LCMS (ES, m/z): 467.2 [M+H]⁺.

Examples 9-10

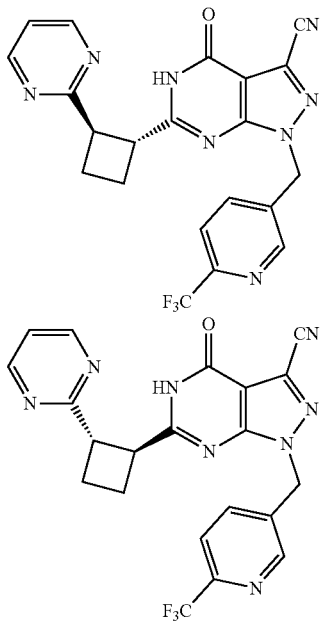

4-Oxo-6-((1,2-trans)-2-(pyrimidin-2-yl)cyclobutyl)-1-((6-(trifluoromethyl)pyridin-3-yl)methyl)-4,5-dihydro-1H-pyrazolo[3,4-d]pyrimidine-3-carbonitrile Step A: (E)-tert-Butyl 2-((6-(trifluoromethyl)pyridin-3-yl)methylene)hydrazinecarboxylate. A round bottom flask was charged with 6-(trifluoromethyl)nicotinaldehyde (10 g, 57.1 mmol) in ethanol (200 mL), followed by the addition of tert-butyl hydrazinecarboxylate (8.30 g, 62.8 mmol) and acetic acid (1.144 ml, 19.99 mmol). The mixture was stirred at ambient temperature for 1 h and the reaction mixture was concentrated under reduced pressure to afford the title compound. ¹H NMR (400 MHz, DMSO-d₆): δ 11.31 (s, 1H), 8.94 (s, 1H), 8.29-8.26 (m, 1H), 8.12 (s, 1H), 7.94 (d, J=11.20 Hz, 1H), 1.49 (s, 9H). LCMS (ES, m/z): 290 [M+H]⁺.

Step B: tert-Butyl 2-((6-(trifluoromethyl)pyridin-3-yl)methyl)hydrazinecarboxylate To a solution of (E)-tert-butyl 2-((6-(trifluoromethyl)pyridin-3-yl)methylene)-hydrazinecarboxylate (15.2 g, 52.5 mmol) in methanol (150 mL) precooled at 0° C., was added acetic acid (12.62 g, 210 mmol), followed by portion wise addition of sodium cyanoborohydride (33.0 g, 525 mmol). The resulting reaction mixture was warmed to ambient temperature over 30 min then heated at 85° C. for 8 h. The reaction mixture was cooled to ambient temperature, water (400 mL) added and the mixture extracted with ethyl acetate (3×100 mL). The combined organic layers were washed with brine (100 mL), dried over anhydrous sodium sulfate, filtered and concentrated under reduced pressure. The residue was purified by column chromatography (silica gel 230-400 mesh, 30% ethyl acetate/pet ether) to afford the title compound. LCMS (ES, m/z): 292 [M+H]⁺.

Step C: 5-(Hydrazinylmethyl)-2-(trifluoromethyl)pyridine dihydrochloride. A round bottom flask containing a solution of tert-butyl 2-((6-(trifluoromethyl)pyridin-3-yl)methyl)hydrazinecarboxylate (14.9 g, 51.2 mmol) in dichloromethane (30 mL), was cooled to 0° C. and a solution of HCl in Dioxane (150 ml, 600 mmol) was added and the contents stirred at ambient temperature for 18 h. The reaction mixture was concentrated under reduced pressure to afford the title compound which was used in the next step without further purification. ¹H NMR (400 MHz, DMSO-d₆): δ 8.78 (s, 1H), 8.72 (br s, 3H), 8.13 (d, J=7.92 Hz, 1H), 7.94 (d, J=8.00 Hz, 1H), 4.20 (s, 2H). LCMS (ES, m/z): 192 [M+H]⁺.

Step D: 5-Amino-1-((6-(trifluoromethyl)pyridin-3-yl)methyl)-1H-pyrazole-3,4-dicarbonitrile. To a pre-cooled solution of 5-(hydrazinylmethyl)-2-(trifluoromethyl)pyridine dihydrochloride (2 g, 7.57 mmol) in ethanol (20 mL) at 0° C. was added triethylamine (2.299 g, 22.72 mmol) and ethene-1,1,2,2-tetracarbonitrile (0.970 g, 7.57 mmol) sequentially. The reaction mixture was stirred at ambient temperature for 16 h, quenched with water (100 mL) and extracted with ethyl acetate (2×100 mL). The combined organic layers were washed with brine (100 mL), dried over anhydrous sodium sulfate, filtered and concentrated under reduced pressure. The residue was purified by column chromatography (silica gel 230-400 mesh, 35% ethyl acetate/pet ether) to afford the title compound. ¹H NMR (400 MHz, DMSO-d₆): δ 8.69-8.61 (m, 1H), 7.93-7.79 (m, 2H), 7.51 (s, 1H), 6.90 (s, 1H), 5.44 (s, 2H). LCMS (ES, m/z): 291 [M+H]⁺.

Step E: 4-Oxo-6-((1,2-trans)-2-(pyrimidin-2-yl)cyclobutyl)-1-((6-(trifluoromethyl)pyridin-3-yl)methyl)-4,5-dihydro-1H-pyrazolo[3,4-d]pyrimidine-3-carbonitrile. A pressure tube (10 mL) was charged with 5-amino-1-((6-

(trifluoromethyl)pyridin-3-yl)methyl)-1H-pyrazole-3,4-dicarbonitrile (800 mg, 2.74 mmol) in dichloroethane (16.0 mL) at room temperature, which was followed with the addition of trans-2-(pyrimidin-2-yl)cyclobutane-1-carboxylic acid (976 mg, 5.48 mmol) and phosphoryl trichloride (0.754 mL, 8.21 mmol) and the resulting contents were stirred at 80° C. for 18 h. The reaction mixture was cooled to ambient temperature and concentrated under reduced pressure. The residue was purified by preparative HPLC (method is A: 0.1% HCOOH in H$_2$O B: CH$_3$CN, column: Atlandis dC18 (150×4.6 mm) 5 Micron, Flow: 1.2 ml) to obtain the title compound as a mixture of enantiomers. The isomers were separated by chiral SFC HPLC purification (OJ-H, 21×250 mm column; 35% MeOH, with EtOH as a co-solvent; 0.5 mL injection volume; 210 nm UV detection; 72 in 12 mL MeOH/ACN 1:1 concentration) to yield the first eluting isomer, peak 1 as Example 9: $^1$H NMR (400 MHz, DMSO-d$_6$): δ 12.63 (s, 1H), 8.82 (s, 1H), 8.79-8.77 (m, 2H), 8.04 (d, J=8.00 Hz, 1H), 7.88 (d, J=8.00 Hz, 1H), 7.39 (t, J=4.80 Hz, 1H), 5.79 (s, 2H), 4.30-4.24 (m, 1H), 3.97-3.92 (m, 1H), 2.33-2.29 (m, 4H). LCMS (ES, m/z): 453.1 [M+H]$^+$. Second eluting isomer, peak 2 as Example 10: $^1$H NMR (400 MHz, DMSO-d$_6$): δ 12.63 (s, 1H), 8.82 (s, 1H), 8.79-8.77 (m, 2H), 8.04 (d, J=8.00 Hz, 1H), 7.88 (d, J=8.00 Hz, 1H), 7.39 (t, J=4.80 Hz, 1H), 5.79 (s, 2H), 4.30-4.24 (m, 1H), 3.97-3.92 (m, 1H), 2.33-2.29 (m, 4H). LCMS (ES, m/z): 453.1 [M+H]$^+$.

TABLE 2

| Example | Structure | Name | Exact Mass [M + H]+ | SFC Column; Peak # |
|---|---|---|---|---|
| 11 | 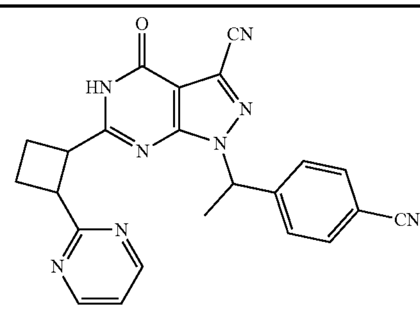 | 1-[1-(4-cyanophenyl)ethyl]-4-oxo-6-(2-pyrimidin-2-ylcyclobutyl)-4,5-dihydro-1H-pyrazolo[3,4-d]pyrimidine-3-carbonitrile | 423.4 | IF; 1 |
| 12 | 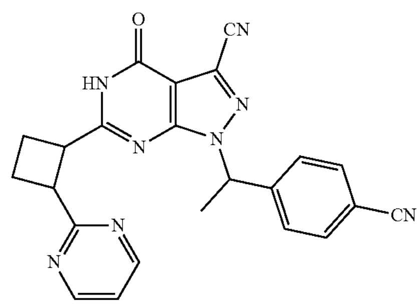 [SMILES: CC(c1ccc(C#N)cc1)n1nc(C#N)c2c(=O)[nH]c(C3CCC3c3ncccn3)nc21] | 1-[1-(4-cyanophenyl)ethyl]-4-oxo-6-(2-pyrimidin-2-ylcyclobutyl)-4,5-dihydro-1H-pyrazolo[3,4-d]pyrimidine-3-carbonitrile | 423.4 | IF; 2 |
| 13 | 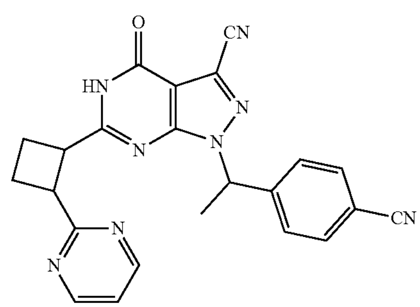 [SMILES: CC(c1ccc(C#N)cc1)n1nc(C#N)c2c(=O)[nH]c(C3CCC3c3ncccn3)nc21] | 1-[1-(4-cyanophenyl)ethyl]-4-oxo-6-(2-pyrimidin-2-ylcyclobutyl)-4,5-dihydro-1H-pyrazolo[3,4-d]pyrimidine-3-carbonitrile | 423.4 | IF; 3 |
| 14 | 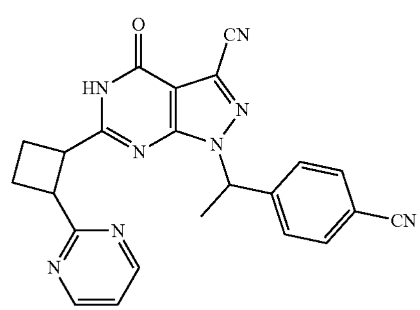 [SMILES: CC(c1ccc(C#N)cc1)n1nc(C#N)c2c(=O)[nH]c(C3CCC3c3ncccn3)nc21] | 1-[1-(4-cyanophenyl)ethyl]-4-oxo-6-(2-pyrimidin-2-ylcyclobutyl)-4,5-dihydro-1H-pyrazolo[3,4-d]pyrimidine-3-carbonitrile | 423.4 | IF; 4 |

TABLE 2-continued

| Example | Structure | Name | Exact Mass [M + H]+ | SFC Column; Peak # |
|---|---|---|---|---|
| 15 | 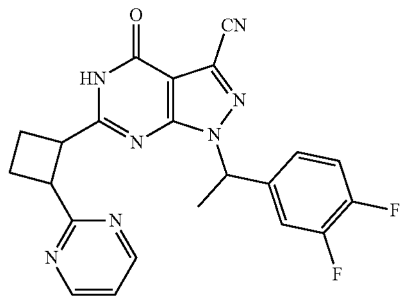 [SMILES: CC(c1ccc(F)c(F)c1)n1nc(C#N)c2c(=O)[nH]c(C3CCC3c3ncccn3)nc21] | 1-(1-(3,4-difluorophenyl)ethyl)-4-oxo-6-(2-(pyrimidin-2-yl)cyclobutyl)-4,5-dihydro-1H-pyrazolo[3,4-d]pyrimidine-3-carbonitrile | 434.2 | AD-H; 1 |
| 16 | 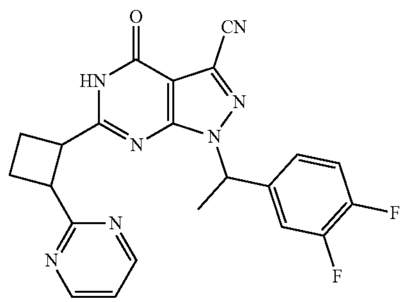 [SMILES: CC(c1ccc(F)c(F)c1)n1nc(C#N)c2c(=O)[nH]c(C3CCC3c3ncccn3)nc21] | 1-(1-(3,4-difluorophenyl)ethyl)-4-oxo-6-(2-(pyrimidin-2-yl)cyclobutyl)-4,5-dihydro-1H-pyrazolo[3,4-d]pyrimidine-3-carbonitrile | 434.2 | AD-H; 2 |
| 17 | 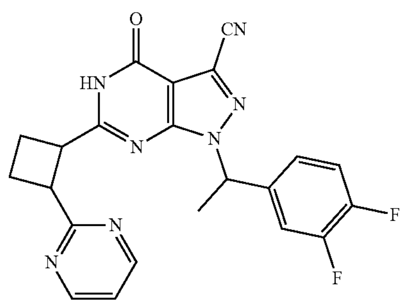 [SMILES: CC(c1ccc(F)c(F)c1)n1nc(C#N)c2c(=O)[nH]c(C3CCC3c3ncccn3)nc21] | 1-(1-(3,4-difluorophenyl)ethyl)-4-oxo-6-(2-(pyrimidin-2-yl)cyclobutyl)-4,5-dihydro-1H-pyrazolo[3,4-d]pyrimidine-3-carbonitrile | 434.2 | AD-H; 3 |
| 18 | 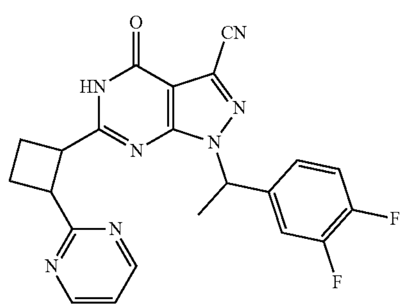 [SMILES: CC(c1ccc(F)c(F)c1)n1nc(C#N)c2c(=O)[nH]c(C3CCC3c3ncccn3)nc21] | 1-(1-(3,4-difluorophenyl)ethyl)-4-oxo-6-(2-(pyrimidin-2-yl)cyclobutyl)-4,5-dihydro-1H-pyrazolo[3,4-d]pyrimidine-3-carbonitrile | 434.2 | AD-H; 4 |
| 19 | 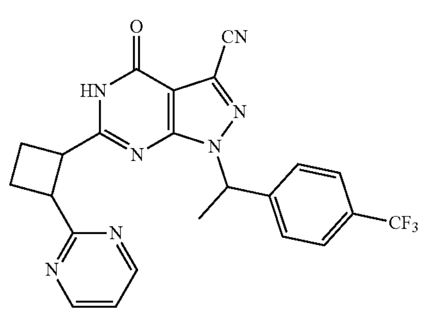 [SMILES: CC(c1ccc(C(F)(F)F)cc1)n1nc(C#N)c2c(=O)[nH]c(C3CCC3c3ncccn3)nc21] | 4-oxo-6-[2-pyrimidin-2-ylcyclobutyl]-1-{1-[4-(trifluoromethyl)phenyl]ethyl}-4,5-dihydro-1H-pyrazolo[3,4-d]pyrimidine-3-carbonitrile | 466.3 | OJ-H; 1 |

TABLE 2-continued

| Example | Structure | Name | Exact Mass [M + H]+ | SFC Column; Peak # |
|---|---|---|---|---|
| 20 | 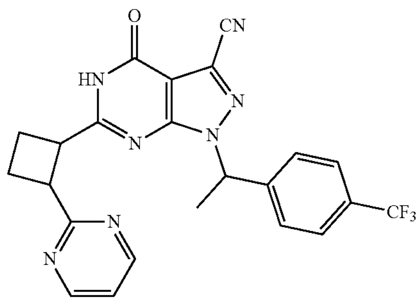 [SMILES: CC(c1ccc(C(F)(F)F)cc1)n1nc(C#N)c2c(=O)[nH]c(C3CCC3c3ncccn3)nc21] | 4-oxo-6-[2-pyrimidin-2-ylcyclobutyl]-1-{(1S)-1-[4-(trifluoromethyl)phenyl]ethyl}-4,5-dihydro-1H-pyrazolo[3,4-d]pyrimidine-3-carbonitrile | 466.3 | OJ-H; 2 |
| 21 | 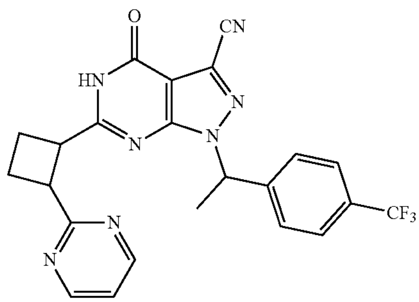 [SMILES: CC(c1ccc(C(F)(F)F)cc1)n1nc(C#N)c2c(=O)[nH]c(C3CCC3c3ncccn3)nc21] | 4-oxo-6-[2-pyrimidin-2-ylcyclobutyl]-1-{1-[4-(trifluoromethyl)phenyl]ethyl}-4,5-dihydro-1H-pyrazolo[3,4-d]pyrimidine-3-carbonitrile | 466.3 | OJ-H; 3 |
| 22 | 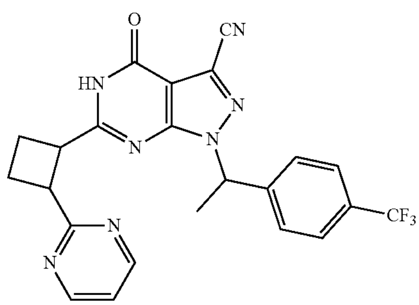 [SMILES: CC(c1ccc(C(F)(F)F)cc1)n1nc(C#N)c2c(=O)[nH]c(C3CCC3c3ncccn3)nc21] | 4-oxo-6-[2-pyrimidin-2-ylcyclobutyl]-1-{1-[4-(trifluoromethyl)phenyl]ethyl}-4,5-dihydro-1H-pyrazolo[3,4-d]pyrimidine-3-carbonitrile | 466.2 | OJ-H; 4 |
| 23 | 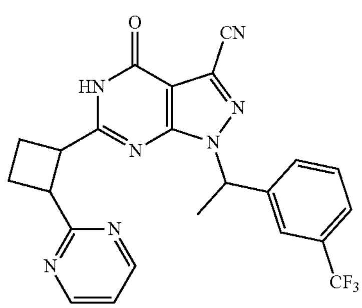 [SMILES: CC(c1cccc(C(F)(F)F)c1)n1nc(C#N)c2c(=O)[nH]c(C3CCC3c3ncccn3)nc21] | 4-oxo-6-[2-pyrimidin-2-ylcyclobutyl]-1-{1-[3-(trifluoromethyl)phenyl]ethyl}-4,5-dihydro-1H-pyrazolo[3,4-d]pyrimidine-3-carbonitrile | 466.4 | YMC Lux C2; 1 |
| 24 | 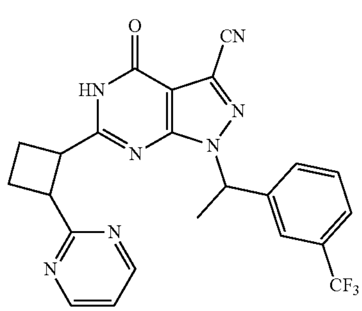 [SMILES: CC(c1cccc(C(F)(F)F)c1)n1nc(C#N)c2c(=O)[nH]c(C3CCC3c3ncccn3)nc21] | 4-oxo-6-[2-pyrimidin-2-ylcyclobutyl]-1-{1-[3-(trifluoromethyl)phenyl]ethyl}-4,5-dihydro-1H-pyrazolo[3,4-d]pyrimidine-3-carbonitrile | 466.4 | YMC Lux C2; 2 |

TABLE 2-continued

| Example | Structure | Name | Exact Mass [M + H]+ | SFC Column; Peak # |
|---|---|---|---|---|
| 25 | 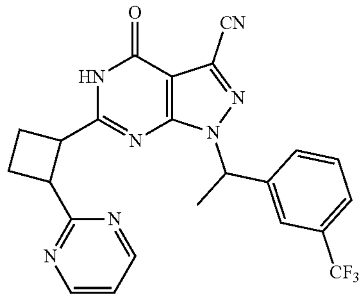 [SMILES: CC(c1cccc(C(F)(F)F)c1)n1nc(C#N)c2c(=O)[nH]c(C3CCC3c3ncccn3)nc21] | 4-oxo-6-[2-pyrimidin-2-ylcyclobutyl]-1-{1-[3-(trifluoromethyl)phenyl]ethyl}-4,5-dihydro-1H-pyrazolo[3,4-d]pyrimidine-3-carbonitrile | 466.4 | YMC Lux C2; 3 |
| 26 | 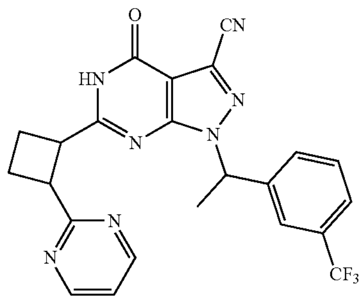 [SMILES: CC(c1cccc(C(F)(F)F)c1)n1nc(C#N)c2c(=O)[nH]c(C3CCC3c3ncccn3)nc21] | 4-oxo-6-[2-pyrimidin-2-ylcyclobutyl]-1-{1-[3-(trifluoromethyl)phenyl]ethyl}-4,5-dihydro-1H-pyrazolo[3,4-d]pyrimidine-3-carbonitrile | 466.4 | YMC Lux C2; 4 |

The following compounds were prepared according to the general procedure provided in the examples and procedures herein using known or prepared starting materials, as described in the reaction schemes and examples herein. The requisite starting materials are either prepared as described in the intermediates section, commercially available, or may be prepared from commercially available reagents using conventional reactions well known in the art without undue experimentation.

TABLE 3

| Ex. | Structure | Name | Exact Mass [M + H]+ | Prep-HPLC Condition; Peak # | Chiral HPLC Condition; Peak # |
|---|---|---|---|---|---|
| 27 | Isomer A | 4-oxo-6-(2-(pyrimidin-2-yl)cyclobutyl)-1-(1-(5-(trifluoromethyl)-pyrazin-2-yl)ethyl)-4,5-dihydro-1H-pyrazolo[3,4-d]pyrimidine-3-carbonitrile | 468.1 | Condition A | Condition B; 1 |
| 28 | Isomer B | 4-oxo-6-(2-(pyrimidin-2-yl)cyclobutyl)-1-(1-(5-(trifluoromethyl)-pyrazin-2-yl)ethyl)-4,5-dihydro-1H-pyrazolo[3,4-d]pyrimidine-3-carbonitrile | 468.1 | See above (Ex. 27) | Condition B; 2 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 29 | Isomer C | 4-oxo-6-(2-(pyrimidin-2-yl)cyclobutyl)-1-(1-(5-(trifluoromethyl)-pyrazin-2-yl)ethyl)-4,5-dihydro-1H-pyrazolo[3,4-d]pyrimidine-3-carbonitrile | 468.1 | See above (Ex. 27) | Condition B; 3 |
| 30 | Isomer D | 4-oxo-6-(2-(pyrimidin-2-yl)cyclobutyl)-1-(1-(5-(trifluoromethyl)-pyrazin-2-yl)ethyl)-4,5-dihydro-1H-pyrazolo[3,4-d]pyrimidine-3-carbonitrile | 468.1 | See above (Ex. 27) | Condition B; 4 |
| 31 | Isomer C | 6-(2-(5-methyl-pyrimidin-2-yl)cyclobutyl)-4-oxo-1-(1-(6-(trifluoromethyl)-pyridin-3-yl)ethyl)-4,5-dihydro-1H-pyrazolo[3,4-d]pyrimidine-3-carbonitrile | 481.2 | Condition A; Peak 2 was further purified (Condition A) to give 31 | — |
| 32 | Isomer D | 6-(2-(5-methyl-pyrimidin-2-yl)cyclobutyl)-4-oxo-1-(1-(6-(trifluoromethyl)-pyridin-3-yl)ethyl)-4,5-dihydro-1H-pyrazolo-[3,4-d]pyrimidine-3-carbonitrile | 481.2 | Condition A; 3 | Condition B; 1 |
| 33 | Isomer E | 6-(2-(5-methyl-pyrimidin-2-yl)cyclobutyl)-4-oxo-1-(1-(6-(trifluoromethyl)-pyridin-3-yl)ethyl)-4,5-dihydro-1H-pyrazolo-[3,4-d]pyrimidine-3-carbonitrile | 481.2 | Condition A; 3 | Condition B; 2 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 34 | Isomer A | 4-oxo-6-(2-(pyrimidin-2-yl)cyclobutyl)-1-(1-(2-(trifluoromethyl)-pyrimidin-5-yl)ethyl)-4,5-dihydro-1H-pyrazolo[3,4-d]pyrimidine-3-carbonitrile | 468.1 | — | Condition B; 1 |
| 35 | Isomer B | 4-oxo-6-(2-(pyrimidin-2-yl)cyclobutyl)-1-(1-(2-(trifluoromethyl)-pyrimidin-5-yl)ethyl)-4,5-dihydro-1H-pyrazolo[3,4-d]pyrimidine-3-carbonitrile | 468.1 | — | Condition B; 2 |
| 36 | Isomer C | 4-oxo-6-(2-(pyrimidin-2-yl)cyclobutyl)-1-(1-(2-(trifluoromethyl)-pyrimidin-5-yl)ethyl)-4,5-dihydro-1H-pyrazolo[3,4-d]pyrimidine-3-carbonitrile | 468.1 | — | Condition C; 1 |
| 37 | Isomer D | 4-oxo-6-(2-(pyrimidin-2-yl)cyclobutyl)-1-(1-(2-(trifluoromethyl)-pyrimidin-5-yl)ethyl)-4,5-dihydro-1H-pyrazolo[3,4-d]pyrimidine-3-carbonitrile | 468.1 | — | Condition C; 2 |
| 38 | Isomer AA (Obtained using Intermediate 12) | 1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 449.2 | Condition A; 1 | Condition D; 1 |

TABLE 3-continued

| Ex. | Structure | Name | Exact Mass [M + H]⁺ | Prep-HPLC Condition; Peak # | Chiral HPLC Condition; Peak # |
|---|---|---|---|---|---|
| 39 | Isomer AB (Obtained using Intermediate 12) | 1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 449.2 | Condition A; 1 | Condition D; 2 |
| 40 | Isomer BA (Obtained using Intermediate 12) | 1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 449.2 | Condition A; 2 | Condition C; 1 |
| 41 | Isomer BB (Obtained using Intermediate 12) | 1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 449.2 | Condition A; 2 | Condition C; 2 |
| 42 | Isomer CA (Obtained using Intermediate 13) | 1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 449.2 | Condition A; 1 | Condition E; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 43 | Isomer CB (Obtained using Intermediate 13) | 1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 449.2 | Condition A; 1 | Condition E; 2 |
| 44 | Isomer DA (Obtained using Intermediate 13) | 1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 449.2 | Condition A; 2 | Condition C; 1 |
| 45 | Isomer DB (Obtained using Intermediate 13) | 1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 449.2 | Condition A; 2 | Condition C; 2 |
| 46 | Isomer A | 4-oxo-6-(2-(pyrimidin-2-yl)cyclobutyl)-1-(1-(tetrahydro-2H-pyran-4-yl)ethyl)-4,5-dihydro-1H-pyrazolo[3,4-d]pyrimidine-3-carbonitrile | 406.2 | — | Condition B; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 47 | 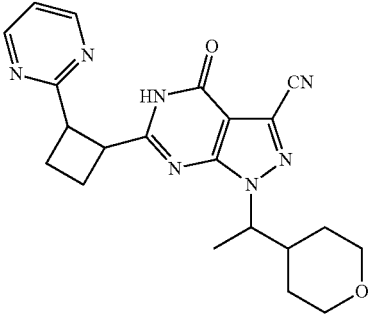 Isomer B | 4-oxo-6-(2-(pyrimidin-2-yl)cyclobutyl)-1-(1-(tetrahydro-2H-pyran-4-yl)ethyl)-4,5-dihydro-1H-pyrazolo[3,4-d]pyrimidine-3-carbonitrile | 406.2 | — | Condition B; 2 |
| 48 | 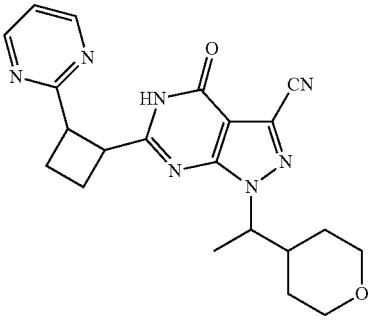 Isomer C | 4-oxo-6-(2-(pyrimidin-2-yl)cyclobutyl)-1-(1-(tetrahydro-2H-pyran-4-yl)ethyl)-4,5-dihydro-1H-pyrazolo[3,4-d]pyrimidine-3-carbonitrile | 406.2 | — | Condition F; 1 |
| 49 | 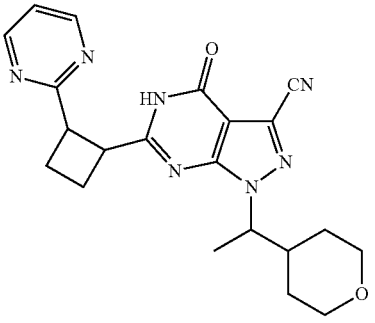 Isomer D | 4-oxo-6-(2-(pyrimidin-2-yl)cyclobutyl)-1-(1-(tetrahydro-2H-pyran-4-yl)ethyl)-4,5-dihydro-1H-pyrazolo[3,4-d]pyrimidine-3-carbonitrile | 406.2 | — | Condition F; 2 |
| 50 | 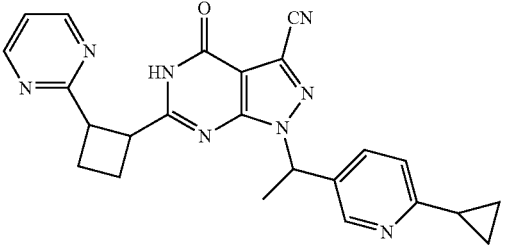 Isomer AA (Obtained using Intermediate 16) | 1-(1-(6-cyclopropylpyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 439.2 | Condition A; 1 | Condition B; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 51 | Isomer AB (Obtained using Intermediate 16) | 1-(1-(6-cyclopropylpyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 439.2 | Condition A; 1 | Condition B; 2 |
| 52 | Isomer BA (Obtained using Intermediate 16) | 1-(1-(6-cyclopropyl-pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 439.2 | Condition A; 2 | Condition G; 1 |
| 53 | Isomer BB (Obtained using Intermediate 16) | 1-(1-(6-cyclopropyl-pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 439.2 | Condition A; 2 | Condition G; 2 |
| 54 | Isomer CA (Obtained using Intermediate 17) | 1-(1-(6-cyclopropyl-pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 439.2 | Condition A; 1 | Condition G; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 55 | Isomer CB (Obtained using Intermediate 17) | 1-(1-(6-cyclopropyl-pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 439.2 | Condition A; 1 | Condition G; 2 |
| 56 | Isomer DA (Obtained using Intermediate 17 in Table 3) | 1-(1-(6-cyclopropyl-pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 439.2 | Condition A; 2 | Condition B; 1 |
| 57 | Isomer DB (Obtained using Intermediate 17) | 1-(1-(6-cyclopropyl-pyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 439.2 | Condition A; 2 | Condition B; 2 |
| 58 | Isomer A | 6-(2-(5-bromo-pyrimidin-2-yl)cyclobutyl)-4-oxo-1-((S)-1-(6-(trifluoro-methyl)pyridin-3-yl)ethyl)-4,5-dihydro-1H-pyrazolo[3,4-d]pyrimidine-3-carbonitrile | 545.1, 547.1 | — | Condition B; 1 |

TABLE 3-continued

| Ex. | Structure | Name | Exact Mass [M + H]⁺ | Prep-HPLC Condition; Peak # | Chiral HPLC Condition; Peak # |
|---|---|---|---|---|---|
| 59 | Isomer B | 6-(2-(5-bromo-pyrimidin-2-yl)cyclobutyl)-4-oxo-1-((S)-1-(6-(trifluoro-methyl)pyridin-3-yl)ethyl)-4,5-dihydro-1H-pyrazolo[3,4-d]pyrimidine-3-carbonitrile | 545.1, 547.1 | — | Condition B; 2 |
| 60 | Isomer A | 6-(2-(5-(difluoro-methoxy)pyrimidin-2-yl)cyclobutyl)-4-oxo-1-((S)-1-(6-(trifluoro-methyl)pyridin-3-yl)ethyl)-4,5-dihydro-1H-pyrazolo[3,4-d]pyrimidine-3-carbonitrile | 533.1 | — | Condition B; 1 |
| 61 | Isomer B | 6-(2-(5-(difluoro-methoxy)pyrimidin-2-yl)cyclobutyl)-4-oxo-1-((S)-1-(6-(trifluoro-methyl)pyridin-3-yl)ethyl)-4,5-dihydro-1H-pyrazolo[3,4-d]pyrimidine-3-carbonitrile | 533.1 | — | Condition B; 2 |

TABLE 3-continued

| Ex. | Structure | Name | Exact Mass [M + H]⁺ | Prep-HPLC Condition; Peak # | Chiral HPLC Condition; Peak # |
|---|---|---|---|---|---|
| 62 | Isomer A | 6-(2-(5-ethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile | 495.2 | — | Condition H; 1 |
| 63 | Isomer B | 6-(2-(5-ethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile | 495.2 | — | Condition H; 2 |
| 64 | Isomer AA | 1-(1-(5-fluoropyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 417.2 | — | Condition I; Peak 1 was further separated by Condition B; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 65 | Isomer AB | 1-(1-(5-fluoropyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 417.2 | — | Condition I; Peak 1 was further separated by Condition B; 2 |
| 66 | Isomer B | 1-(1-(5-fluoropyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 417.2 | — | Condition I; 2 |
| 67 | Isomer C | 1-(1-(5-fluoropyridin-3-yl)ethyl)-4-oxo-6-(2-(pyrimidin-2-yl)cyclobutyl)-4,5-dihydro-1H-pyrazolo[3,4-d]pyrimidine-3-carbonitrile | 417.2 | — | Condition I; 3 |
| 68 | Isomer AA | 1-(1-(1-methyl-1H-pyrazol-4-yl)ethyl)-4-oxo-6-(2-(pyrimidin-2-yl)cyclobutyl)-4,5-dihydro-1H-pyrazolo[3,4-d]pyrimidine-3-carbonitrile | 402.2 | — | Condition J; Peak 1 was further separated by Condition G; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 69 | Isomer AB | 1-(1-(1-methyl-1H-pyrazol-4-yl)ethyl)-4-oxo-6-(2-(pyrimidin-2-yl)cyclobutyl)-4,5-dihydro-1H-pyrazolo[3,4-d]pyrimidine-3-carbonitrile | 402.2 | — | Condition J; Peak 1 was further separated by Condition G; 2 |
| 70 | Isomer B | 1-(1-(1-methyl-1H-pyrazol-4-yl)ethyl)-4-oxo-6-(2-(pyrimidin-2-yl)cyclobutyl)-4,5-dihydro-1H-pyrazolo[3,4-d]pyrimidine-3-carbonitrile | 402.2 | — | Condition J; 2 |
| 71 | Isomer C | 1-(1-(1-methyl-1H-pyrazol-4-yl)ethyl)-4-oxo-6-(2-(pyrimidin-2-yl)cyclobutyl)-4,5-dihydro-1H-pyrazolo[3,4-d]pyrimidine-3-carbonitrile | 402.2 | — | Condition J; 3 |
| 72 | Isomer A | 1-(1-(6-cyclopropyl-pyridin-3-yl)ethyl)-6-(2-(5-fluoropyrimidin-2-yl)cyclobutyl)-4-oxo-4,5-dihydro-1H-pyrazolo[3,4-d]pyrimidine-3-carbonitrile | 457.2 | — | Condition B; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 73 | Isomer B | 1-(1-(6-cyclopropyl-pyridin-3-yl)ethyl)-6-(2-(5-fluoropyrimidin-2-yl)cyclobutyl)-4-oxo-4,5-dihydro-1H-pyrazolo[3,4-d]pyrimidine-3-carbonitrile | 457.2 | — | Condition B; 2 |
| 74 | Isomer C | 1-(1-(6-cyclopropyl-pyridin-3-yl)ethyl)-6-(2-(5-fluoropyrimidin-2-yl)cyclobutyl)-4-oxo-4,5-dihydro-1H-pyrazolo[3,4-d]pyrimidine-3-carbonitrile | 457.2 | — | Condition B; 1 |
| 75 | Isomer D | 1-(1-(6-cyclopropyl-pyridin-3-yl)ethyl)-6-(2-(5-fluoropyrimidin-2-yl)cyclobutyl)-4-oxo-4,5-dihydro-1H-pyrazolo[3,4-d]pyrimidine-3-carbonitrile | 457.2 | — | Condition B; 2 |
| 76 | Isomer A | 4-oxo-6-(2-(pyrimidin-2-yl)cyclobutyl)-1-(1-(2-(trifluoromethyl)thiazol-5-yl)ethyl)-4,5-dihydro-1H-pyrazolo[3,4-d]pyrimidine-3-carbonitrile | 473.1 | — | Condition B; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 77 | Isomer BA | 4-oxo-6-(2-(pyrimidin-2-yl)cyclobutyl)-1-(1-(2-(trifluoromethyl)thiazol-5-yl)ethyl)-4,5-dihydro-1H-pyrazolo[3,4-d]pyrimidine-3-carbonitrile | 473.1 | — | Condition B; Peak 2 was further separated by Condition F; 1 |
| 78 | Isomer BB | 4-oxo-6-(2-(pyrimidin-2-yl)cyclobutyl)-1-(1-(2-(trifluoromethyl)thiazol-5-yl)ethyl)-4,5-dihydro-1H-pyrazolo[3,4-d]pyrimidine-3-carbonitrile | 473.1 | — | Condition B; Peak 2 was further separated by Condition F; 2 |
| 79 | Isomer C | 4-oxo-6-(2-(pyrimidin-2-yl)cyclobutyl)-1-(1-(2-(trifluoromethyl)thiazol-5-yl)ethyl)-4,5-dihydro-1H-pyrazolo[3,4-d]pyrimidine-3-carbonitrile | 473.1 | — | Condition B; 3 |
| 80 | Isomer A | 1-(1-(2-cyclopropyl-pyrimidin-5-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile | 458.2 | — | Condition B; 1 |

TABLE 3-continued

| Ex. | Structure | Name | Exact Mass [M + H]+ | Prep-HPLC Condition; Peak # | Chiral HPLC Condition; Peak # |
|---|---|---|---|---|---|
| 81 | Isomer B | 1-(1-(2-cyclopropyl-pyrimidin-5-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile | 458.2 | — | Condition B; 2 |

The following compounds were prepared according to the general procedure provided in the examples and procedures herein using known or prepared starting materials, as described in the reaction schemes and examples herein, such as described for Examples 9-10. The reaction mixture was concentrated after treatment with phosphoryl trichloride. The crude residue was dissolved in ACN/H$_2$O (~3:1 ratio) at room temperature. The reaction solution was stirred at 50° C. overnight and concentrated under vacuum. The residue thus obtained was purified by reverse phase HPLC, and then chiral HPLC if required. The requisite starting materials are either prepared as described in the intermediates section, commercially available, or may be prepared from commercially available reagents using conventional reactions well known in the art without undue experimentation. General purification condition for Prep HPLC (Condition A): X Bridge C18 OBD Prep Column 100 Å, 10 μm, 19 mm×250 mm; Mobile Phase A: water with 20 mmol/L NH$_4$HCO$_3$, Mobile Phase B: ACN; Flow rate: 20 mL/min; Gradient: 20-50% B to 50-80% B. Chiral HPLC conditions: Condition B: CHIRALPAK-IC, 2×25 cm, 5 μm; Mobile Phase A: Hex:DCM=3:1 or Hex:DCM=1:1 or Hex or EtOH:DCM=3:1; Mobile Phase B: EtOH: 15-50% or IPA 40-50% or MeOH:IPA=1:1, 60%. Condition C: Chiralpak IA, 2×25 cm, 5 μm; Mobile Phase A: Hex:DCM=3:1 or Hex; Mobile Phase B: EtOH: 20-100%. Condition D: CHIRALPAK IE, 2×25 cm, 5 μm; Mobile Phase A: Hex, Mobile Phase B: EtOH: 23%. Condition E: (R,R)-WHELK-O1-Kromasil, 5×25 cm, 5 μm; Mobile Phase A: Hex, Mobile Phase B: EtOH: 30%. Condition F: CHIRAL ART Cellulose-SB, 2×25 cm, 5 μm; Mobile Phase A: Hex, Mobile Phase B: IPA: 40% or EtOH 30%. Condition G: CHIRALPAK AD-H, 2×25 cm; Mobile Phase A: Hex, Mobile Phase B: EtOH: 15-20%. Condition H: CHIRALPAK AS-H, 5×25 cm, 5 μm; Mobile Phase A: Hex, Mobile Phase B: EtOH: 30% or IPA 50%. Condition I: CHIRALPAK ID-03, 2×25 cm, 5 μm; Mobile Phase A: Hex, Mobile Phase B: IPA: 40%. Condition J: CHIRALPAK IG UL001, 2×25 cm, 5 μm; Mobile Phase A: Hex, Mobile Phase B: EtOH: 40-50%.

Example 82

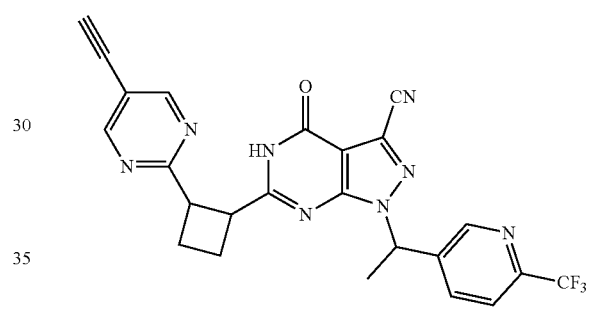

6-(2-(5-ethynylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile Step A: To a solution of 1-tributylstannyl-2-trimethylsilylacetylene (34.5 mg, 0.089 mmol) in DMF (500 μl), was added 6-(2-(5-bromopyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile (24.3 mg, 0.045 mmol) and PdCl2(dppf) (3.26 mg, 4.46 μmol) at room temperature. The reaction mixture was stirred at 100° C. for 2 h. The mixture was cooled, aqueous ammonium chloride (saturated, 10 mL) was added and the mixture was extracted with ethyl acetate (3×15 mL). The combined organic fractions were washed with aqueous ammonium chloride (saturated, 15 mL), dried (MgSO$_4$), filtered and the solvent was evaporated under reduced pressure. The residue was purified by preparative reverse phase LC (C-18) RediSep Rf 50 g HP, eluting with Acetonitrile/Water from 5 to 100%, wavelength 254 mm, to give 4-oxo-1-(1-(6-(trifluoromethyl)pyridin-3-yl)ethyl)-6-(2-(5-(((trimethylsilyl)ethyl)pyrimidin-2-yl)cyclobutyl)-4,5-dihydro-1H-pyrazolo[3,4-d]pyrimidine-3-carbonitrile. LCMS (ES, m/z): 653.3 [M+H]+. $^1$H NMR (500 MHz, Chloroform-d) δ 11.98 (s, 1H), 8.85 (d, J=1.8 Hz, 1H), 8.82 (s, 2H), 8.02 (dd, J=2.0, 8.2 Hz, 1H), 7.71 (d, J=8.2 Hz, 1H), 6.23 (q, J=7.1 Hz, 1H), 3.89 (q, J=9.4 Hz, 1H), 3.76 (q, J=9.7 Hz, 1H), 2.63 (p, J=10.3 Hz, 1H), 2.48 (td, J=5.7, 9.9, 10.5 Hz, 2H), 2.32 (ddd, J=5.2, 10.6, 13.7 Hz, 1H), 2.04 (d, J=7.2 Hz, 3H), 0.28 (s, 9H).

Step B: To a solution of 4-oxo-1-(1-(6-(trifluoromethyl)pyridin-3-yl)ethyl)-6-(2-(5-((trimethylsily)ethynl)pyrimidin-2-yl)cyclobutyl)-4,5-dihydro-1H-pyrazolo[3,4-d]pyrimidine-3-carbonitrile (16.1 mg, 0.029 mmol) in acetonitrile (500 µl), was added TBAF (60 µl, 0.060 mmol) at room temperature. The reaction mixture was stirred at room temperature for 1 h. The mixture was cooled, aqueous ammonium chloride (saturated, 10 mL) was added and the mixture was extracted with ethyl acetate (3×15 mL). The combined organic fractions were washed with aqueous ammonium chloride (saturated, 15 mL), dried (MgSO$_4$), filtered and the solvent was evaporated under reduced pressure. The residue was purified by preparative LC Reverse phase (C-18) RediSep Rf 50 g HP, eluting with Acetonitrile/Water from 5 to 100% wavelength 254 mm. This was further purified by preparative LC Reverse phase (C-18), eluting with Acetonitrile/Water from 7 to 100%, to give EXAMPLE 82, 6-(2-(5-ethynylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile. LCMS (ES, m/z): 491.2 [M+H]$^+$. $^1$H NMR (500 MHz, Chloroform-d) δ 8.87 (s, 2H), 8.86-8.84 (m, 1H), 8.03 (d, J=6.9 Hz, 1H), 7.71 (d, J=8.2 Hz, 1H), 6.23 (q, J=7.1 Hz, 1H), 3.91 (q, J=9.4 Hz, 1H), 3.77 (q, J=9.6 Hz, 1H), 3.42 (s, 1H), 2.64 (p, J=10.2 Hz, 1H), 2.49 (dt, J=4.6, 9.3 Hz, 2H), 2.32 (tt, J=5.1, 10.7 Hz, 1H), 2.04 (d, J=7.2 Hz, 3H).

Examples 83-84

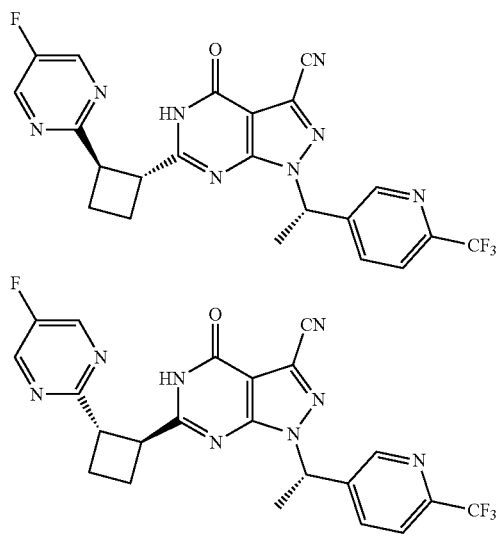

6-((1R,2R)-2-(5-fluoropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile 6-((1S,2S)-2-(5-fluoropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile In a 20 mL vial, a suspension of 2-(5-fluoropyrimidin-2-yl)cyclobutanecarboxylic acid (0.961 g, 4.90 mmol) and (S)-5-amino-1-(1-(6-(trifluoromethyl)pyridin-3-yl)ethyl)-1H-pyrazole-3,4-dicarbonitrile (1.25 g, 4.08 mmol) in dichloroethane (17 ml) was charged with POCl$_3$ (1.141 ml, 12.25 mmol). The vial was capped, and the reaction mixture was heated to 60° C. over night. The reaction mixture was cooled to room temperature. The reaction mixture was transferred to a flask and the solvent was removed under vacuum. Acetonitrile (12.0 mL) and water (5 mL) were charged to the reaction mixture, which was then heated to 50° C. for 3 hours. The reaction mixture was cooled down to room temperature and charged with aqueous sodium hydrogen carbonate (saturated, 30 mL). It was extracted with ethyl acetate (3×30 mL). The combined organic fractions were dried (Na$_2$SO$_4$), filtered and the solvent was evaporated under reduced pressure. The residue was purified by column chromatography on silica gel RediSep Gold 120 g silica, eluting with MeOH/DCM 0-8% to give 6-(2-(5-fluoropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile. The title compounds were obtained by chiral preparative SFC (Chiralpak OJ-H, 21×250 mm, 20% MeOH). The faster-eluting isomer of the title compound (EXAMPLE 83). LCMS (ES, m/z): 485.4 [M+H]$^+$. $^1$H NMR (500 MHz, Chloroform-d) δ 11.67 (s, 1H), 8.81 (s, 1H), 8.70 (s, 2H), 7.99 (d, J=8.5 Hz, 1H), 7.69 (d, J=8.1 Hz, 1H), 6.24 (q, J=7.1 Hz, 1H), 3.91 (q, J=9.4 Hz, 1H), 3.72 (q, J=9.7 Hz, 1H), 2.71 (dt, J=20.8, 11.0 Hz, 1H), 2.49 (dq, J=21.2, 10.6, 9.7 Hz, 2H), 2.30 (q, J=8.9, 8.3 Hz, 1H), 2.06 (d, J=7.2 Hz, 3H). The slower-eluting isomer of the title compound (EXAMPLE 84). LCMS (ES, m/z): 485.4 [M+H]$^+$. $^1$H NMR (500 MHz, Chloroform-d) δ 11.74 (s, 1H), 8.86 (s, 1H), 8.69 (s, 2H), 8.04 (d, J=7.9 Hz, 1H), 7.72 (d, J=8.2 Hz, 1H), 6.23 (q, J=7.2 Hz, 1H), 3.87 (q, J=9.3 Hz, 1H), 3.75 (q, J=9.4 Hz, 1H), 2.64 (dt, J=20.4, 10.7 Hz, 1H), 2.56-2.40 (m, 2H), 2.37-2.26 (m, 1H), 2.04 (d, J=7.2 Hz, 3H).

Example 85

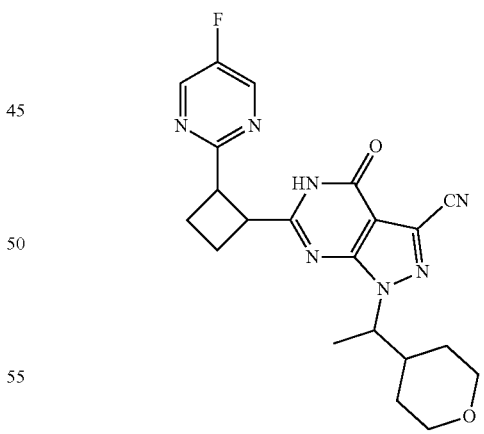

6-(2-(5-fluoropyrimidin-2-yl)cyclobutyl)-4-oxo-1-(1-(tetrahydro-2H-pyran-4-yl)ethyl)-4,5-dihydro-1H-pyrazolo[3,4-d]pyrimidine-3-carbonitrile The title compound was prepared using procedures similar to those described for EXAMPLE 83 and 84 utilizing 5-amino-1-(1-(tetrahydro-2H-pyran-4-yl)ethyl)-1H-pyrazole-3,4-dicarbonitrile (single isomer, peak 1 from SFC separation) and 2-(5-fluoropyrimidin-2-yl)cyclobutane carboxylic acid to afford the title compound (EXAMPLE 85, single isomer) by chiral preparative SFC (Chiralpak AD-H, 21×250 mm, 10% MeOH). LCMS (ES, m/z): 424.2 [M+H]$^+$.
$^1$H NMR (500 MHz, CDCl$_3$): δ 10.70 (s, 1H), 8.68 (s, 2H), 4.09-3.94 (m, 3H), 3.88 (dd, J=11.5, 3.9 Hz, 1H), 3.45 (q, J=9.9, 9.2 Hz, 1H), 3.38 (t, J=11.8 Hz, 1H), 3.28 (t, J=11.7 Hz, 1H), 2.47 (ddd, J=21.9, 11.4, 6.3 Hz, 3H), 2.22 (t, J=8.4 Hz, 1H), 2.16-2.04 (m, 1H), 1.57 (d, 3H), 1.31 (dq, J=20.3, 7.9, 6.3 Hz, 2H), 1.16 (qd, J=12.3, 4.6 Hz, 2H).

Example 86

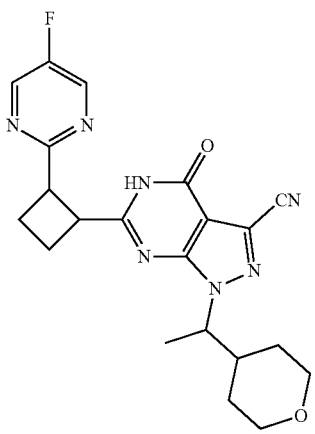 [SMILES: CC(C1CCOCC1)n1nc(C#N)c2c(=O)[nH]c(C3CCC3c3ncc(F)cn3)nc21]

6-(2-(5-fluoropyrimidin-2-yl)cyclobutyl)-4-oxo-1-(1-(tetrahydro-2H-pyran-4-yl)ethyl)-4,5-dihydro-1H-pyrazolo[3,4-d]pyrimidine-3-carbonitrile The title compound was prepared using procedures similar to those described for EXAMPLE 83 and 84 utilizing 5-amino-1-(1-(tetrahydro-2H-pyran-4-yl)ethyl)-1H-pyrazole-3,4-dicarbonitrile (single isomer, peak 2 from SFC separation) and 2-(5-fluoropyrimidin-2-yl)cyclobutane carboxylic acid to afford the title compound (EXAMPLE 86, single isomer) by chiral preparative SFC (Chiralpak AD-H, 21×250 mm, 10% MeOH). LCMS (ES, m/z): 424.2 [M+H]$^+$.
$^1$H NMR (500 MHz, CDCl$_3$): δ 10.55 (s, 1H), 8.64 (s, 2H), 4.06-3.99 (m, 2H), 3.99-3.87 (m, 2H), 3.49 (q, J=9.3 Hz, 1H), 3.38 (t, J=11.6 Hz, 1H), 3.30 (t, J=11.9 Hz, 1H), 2.60-2.49 (m, 1H), 2.46 (q, J=9.8, 8.9 Hz, 2H), 2.21-2.04 (m, 2H), 1.37-1.27 (m, 2H), 1.18 (qd, J=12.1, 4.4 Hz, 2H). (CH$_3$ under solvent peak)

Examples 87-88

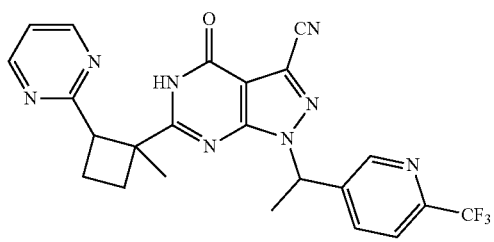

87

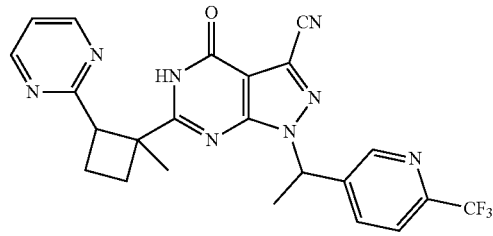

88

6-(1-methyl-2-(pyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile Step A: To a slurry of 2-(pyrimidin-2-yl)cyclobutanecarboxylic acid (cis-racemic, 980 mg, 5.5 mmol) in MeOH/Toluene (5 ml/22 ml) at 0° C. was added TMS diazomethane (2M in hexanes, 2.9 ml, 5.77 mmol) dropwise. The reaction mixture was warmed to ambient temperature over 3.5 hrs. Added 1 ml of trimethylsilyl diazomethane (2M in hexanes). The reaction was continued at ambient temperature for 30 min more. The solvent was then concentrated. The residue was purified by column chromatography on silica gel (Redisep gold 40 g silica cartridge), eluting with 0-100% of EtOAc/hexanes to provide the methyl ester. LCMS (ES, m/z): 193.2 [M+H]$^+$.

To the methyl ester from above [methyl 2-(pyrimidin-2-yl)cyclobutanecarboxylate, 192 mg, 1 mmol], in THF (4 ml) at −78° C., under N2 atmosphere, was added LHMDS (1M in THF, 1.2 ml, 1.2 mmol). Maintained reaction at −78° C. for 1 hr. Then added MeI (0.1 ml, 1.6 mmol) dropwise. Slowly warmed reaction to 0° C., over 2 hr. Quenched the reaction by addition of satd NH4Cl solution (40 ml). Extracted with EtOAc (2×30 ml). The combined org layer was dried (Na2SO4), filtered and concentrated. Crude residue was purified by column chromatography on silica gel (Redisep gold 24 g silica cartridge), eluting with 20-100% of EtOAc/hexanes to provide methyl 1-methyl-2-(pyrimidin-2-yl)cyclobutanecarboxylate. LCMS (ES, m/z): 207.2 [M+H]$^+$.

Step B: To methyl 1-methyl-2-(pyrimidin-2-yl)cyclobutanecarboxylate (95 mg, 0.461 mmol) in THF/MeOH/water (1/1/0.5 ml) was added aq 1M LiOH (0.92 ml, 0.92 mmol). Stirred reaction at ambient temperature for 4.5 hrs. At this time added more aq 1M LiOH (~0.5 ml, ~0.5 mmol), and stirred at ambient temperature overnight. Then concentrated most of the solvent, diluted with water (15 ml). Added aq 1M HCl (till pH=1-2, by pH paper). Extracted the with EtOAc (2×20 ml). The combined org layer was dried (Na2SO4), filtered, concentrated to provide 1-methyl-2-(pyrimidin-2-yl)cyclobutanecarboxylic acid). LCMS (ES, m/z): 193.2 [M+H]$^+$.

Step C: To 1-methyl-2-(pyrimidin-2-yl)cyclobutanecarboxylic acid (50 mg, 0.26 mmol) in dichloroethane (1.5 ml) was added (S)-5-amino-1-(1-(6-(trifluoromethyl)pyridin-3-yl)ethyl)-1H-pyrazole-3,4-dicarbonitrile (80 mg, 0.26 mmol) in a vial. Added more dichloroethane (1.5 ml) followed by POCl$_3$ (0.1 ml, 1.07 mmol). The vial was capped and heated at 75° C., overnight. Cooled to the reaction to ambient temperature, added MeCN (~5 ml) and water (1 ml) into rxn mix, and stirred vigorously at 50° C. for 2.5 hrs (total time). Then cooled the reaction to 0° C., diluted with EtOAc (10 ml), added satd NaHCO3 (10 ml), slowly with stirring. Further diluted with EtOAc (30 ml total), and added water (20 ml). Separated org layer, extracted aq layer with EtOAc (30 ml). The combined org layer was washed with brine (50 ml), dried (Na2SO4), filtered and concentrated. The crude material was dissolved in MeCN (10 ml), added aq 1M NaOH (4 ml), and stirred at ambient temperature for ~30 min. Then diluted the mixture with CH2Cl2 (30 ml), added sat'd NH4Cl (25 ml)/brine (5 ml). Stirred, and separated org layer. Extracted aq layer with CH2Cl2 (30 ml). The combined org layer was dried (Na2SO4), filtered and concentrated. The crude residue was purified by reverse phase HPLC. Conditions: Sunfire Prep C-18, 10 uM, 30×150 mm OBD column, flow rate 30 ml/min, gradient=10-90% CH3CN(0.05% TFA) in water (0.05% TFA). Isolated a mixture of peak 3 and peak 4 (containing approx 1:2.5 ratio of peak 3:peak 4). This mixture was further separated by SFC (conditions—OJ-H, 21×250 mm column, 20% MeOH) to provide, Peak 2:Single isomer—6-(1-methyl-2-(pyrimidin-2-yl)cyclobutyl)-4-oxo-1-(1-(6(trifluoromethyl)pyridin-3-yl)ethyl)-4,5-dihydro-1H-pyrazolo[3,4-d]pyrimidine-3-carbonitrile, EXAMPLE 87. LCMS (ES, m/z): 481.3 [M+H]$^+$; $^1$H NMR (400 MHz, Chloroform-d) δ 12.65 (s, 1H), 8.85 (d, J=4.9 Hz, 2H), 8.82 (d, J=1.7 Hz, 1H), 8.02 (dd, J=1.8, 8.2 Hz, 1H), 7.70 (d, J=8.2 Hz, 1H), 7.31 (t, J=4.9 Hz, 1H), 6.23 (q, J=7.0 Hz, 1H), 4.03 (t, J=8.7 Hz, 1H), 2.85-2.66 (m, 2H), 2.43-2.28 (m, 1H), 2.10-1.98 (m, 1H), 2.05 (d, J=7.2 Hz, 3H), 1.18 (s, 3H). Peak 3: Single isomer—6-(1-methyl-2-(pyrimidin-2-yl)cyclobutyl)-4-oxo-1-(1-(6(trifluoromethyl)pyridin-3-yl)ethyl)-4,5-dihydro-1H-pyrazolo[3,4-d]pyrimidine-3-carbonitrile, EXAMPLE 88. LCMS (ES, m/z): 481.3 [M+H]$^+$. $^1$H NMR (400 MHz, Chloroform-d) δ 12.66 (s, 1H), 8.91-8.79 (m, 3H), 8.04 (dd, J=2.1, 8.2 Hz, 1H), 7.72 (d, J=8.1 Hz, 1H), 7.31 (t, J=4.9 Hz, 1H), 6.23 (q, J=7.4 Hz, 1H), 3.99 (t, J=9.2 Hz, 1H), 2.82-2.58 (m, 2H), 2.37-2.29 (m, 1H), 2.11-1.97 (m, 1H), 2.05 (d, J=7.2 Hz, 3H), 1.23 (s, 3H).

Examples 89-90

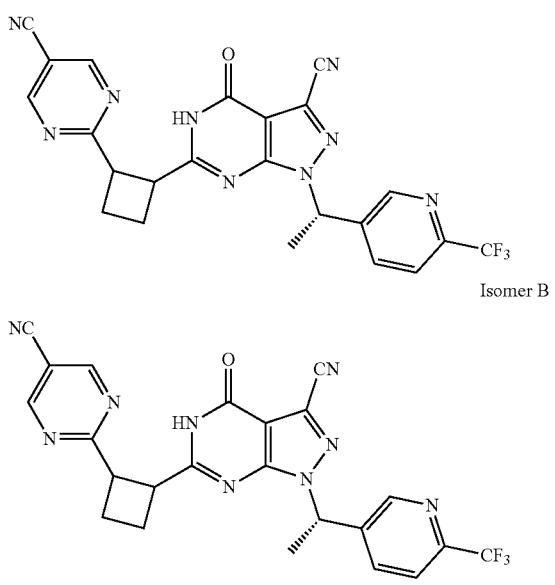

Isomer A

Isomer B 6-(2-(5-cyanopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile Step A: To a solution of 6-(2-(5-bromopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (0.05 g, 0.092 mmol) in 1,4-dioxane (0.5 mL) and water (0.1 mL) were added t-BuBrettphos Pd G$_3$ (0.023 g, 0.027 mmol) and Zn(CN)$_2$ (0.022 g, 0.18 mmol) at room temperature. The reaction mixture was degassed with N$_2$ for 3 times and stirred at 55° C. for 16 h under N$_2$. The resulting solution was diluted with water (20 mL) and extracted with EtOAc (3×20 mL). The combined organic layer was washed with brine (50 mL), dried over anhydrous Na$_2$SO$_4$ and filtered. The filtrate was concentrated under vacuum. The residue was purified by Prep-HPLC with the following conditions: column: X Bridge C18 OBD Prep Column 100 Å, 10 μm, 19 mm×250 mm; Mobile Phase A: water with 20 mmol/L NH$_4$HCO$_3$, Mobile Phase B: ACN; Flow rate: 20 mL/min; Gradient: 58% B to 76% B in 6 min; 254/210 nm. The fractions containing desired product were combined and concentrated under vacuum to afford 6-(2-(5-cyanopyrimidin-2-yl) cyclobutyl)-4-oxo-1-((S)-1-(6-(trifluoromethyl) pyridin-3-yl)ethyl)-4,5-dihydro-1H-pyrazolo[3,4-d]pyrimidine-3-carbonitrile. LCMS (ES, m/z): 492.2 [M+H]$^+$.

Step B: 6-(2-(5-Cyanopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile was separated by Prep-Chiral-HPLC with the following conditions: column: CHIRALPAK IC, 2×25 cm, 5 μm; Mobile Phase A: HEX:DCM=3:1, Mobile Phase B: EtOH; Flow rate: 16 mL/min; Gradient: 50% B to 50% B in 26 min; 254/220 nm. The fractions containing desired product were combined and concentrated under vacuum to afford 6-(2-(5-cyanopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (peak 1, Isomer A, EXAMPLE 89). LCMS (ES, m/z): 492.2 [M+H]$^+$. $^1$H NMR (400 MHz, CDCl$_3$) δ 11.24 (brs, 1H), 9.09 (s, 2H), 8.81 (d, J=1.6 Hz, 1H), 7.99 (dd, J=8.4 Hz, 2.0 Hz, 1H), 7.69 (d, J=8.0 Hz, 1H), 6.23 (q, J=7.2 Hz, 1H), 4.05 (q, J=9.2 Hz, 1H), 3.81 (q, J=9.6 Hz, 1H), 2.77-2.69 (m, 1H), 2.57-2.49 (m, 2H), 2.38-2.31 (m, 1H), 2.06 (d, J=7.2 Hz, 3H), and 6-(2-(5-cyanopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (peak 2, Isomer B, EXAMPLE 90). LCMS (ES, m/z): 492.2 [M+H]$^+$. $^1$H NMR (400 MHz, CDCl$_3$) δ11.28 (brs, 1H), 9.08 (s, 2H), 8.84 (d, J=1.6 Hz, 1H), 8.03 (dd, J=8.0 Hz, 2.0 Hz, 1H), 7.71 (d, J=8.0 Hz, 1H), 6.23 (q, J=7.2 Hz, 1H), 4.02 (q, J=9.6 Hz, 1H), 3.82 (q, J=9.2 Hz, 1H), 2.71-2.63 (m, 1H), 2.56-2.49 (m, 2H), 2.40-2.33 (m, 1H), 2.05 (d, J=6.8 Hz, 3H).

Example 91

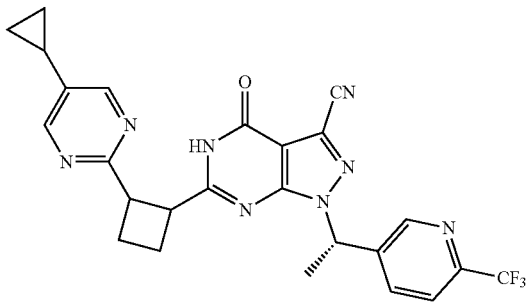

Isomer B 6-(2-(5-cyclopropylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile To a solution of 6-(2-(5-bromopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (EXAMPLE 59, Isomer B) (40.00 mg, 0.073 mmol) in toluene (0.8 mL) and water (0.2 mL) were added cyclopropylboronic acid (9.45 mg, 0.11 mmol), $Cs_2CO_3$ (35.8 mg, 0.11 mmol), diacetoxypalladium (1.65 mg, 7.34 μmol) and XPhos (3.50 mg, 7.34 μmol) at room temperature. The reaction mixture was degassed with $N_2$ for 3 times irradiated with microwave radiation at 140° C. for 4 h. After cooling to room temperature, the resulting mixture was concentrated under vacuum. The residue was diluted with water (10 mL) and extracted with EtOAc (3×10 mL). The combined organic layers were concentrated under vacuum. The residue was purified by Prep-HPLC with the following conditions: column: X Select CSH Prep C18 OBD Column, 19×250 mm, 5 μm; Mobile Phase A: water with 0.05% TFA, Mobile Phase B: ACN; Flow rate: 20 mL/min; Gradient: 20% B to 34% B in 15 min; 254/210 nm. The collected fractions were combined and concentrated under vacuum to afford 6-(2-(5-cyclopropylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (EXAMPLE 91). LCMS (ES, m/z): 507.4. $[M+H]^+$. $^1$H NMR (400 MHz, $CDCl_3$) δ 12.46 (brs, 1H), 8.86 (d, J=2.0 Hz, 1H), 8.58 (s, 2H), 8.03 (dd, J=8.0 Hz, 1.6 Hz, 1H), 7.71 (d, J=8.0 Hz, 1H), 6.24 (q, J=7.2 Hz, 1H), 3.87 (q, J=9.2 Hz, 1H), 3.73 (q, J=9.2 Hz, 1H), 2.65-2.48 (m, 1H), 2.47-2.44 (m, 2H), 2.34-2.27 (m, 1H), 2.04 (d, J=7.2 Hz, 3H), 1.94-1.87 (m, 1H), 1.16-1.12 (m, 2H), 0.84-0.79 (m, 2H).

Example 92

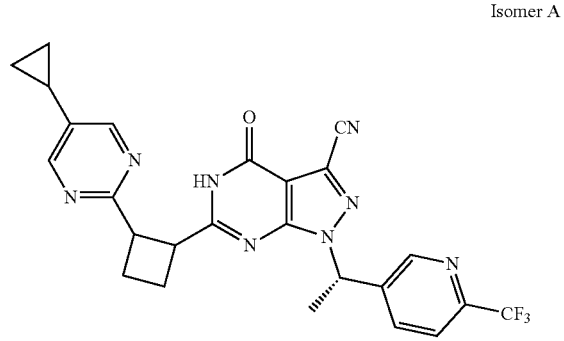 [SMILES: C[C@@H](c1ccc(C(F)(F)F)nc1)n1nc(C#N)c2c(=O)[nH]c(C3CCC3c3ncc(C4CC4)cn3)nc21]

Isomer A 6-(2-(5-cyclopropylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile The title compound EXAMPLE 92 was prepared as described for EXAMPLE 91 using 6-(2-(5-bromopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (EXAMPLE 58, Isomer A). LCMS (ES, m/z): 507.4 $[M+H]^+$. $^1$H NMR (400 MHz, $CDCl_3$) δ 12.46 (brs, 1H), 8.86 (d, J=2.0 Hz, 1H), 8.58 (s, 2H), 8.03 (dd, J=8.0 Hz, 1.6 Hz, 1H), 7.71 (d, J=8.0 Hz, 1H), 6.24 (q, J=7.2 Hz, 1H), 3.87 (q, J=9.2 Hz, 1H), 3.73 (q, J=9.2 Hz, 1H), 2.65-2.48 (m, 1H), 2.47-2.44 (m, 2H), 2.34-2.27 (m, 1H), 2.04 (d, J=7.2 Hz, 3H), 1.94-1.87 (m, 1H), 1.16-1.12 (m, 2H), 0.84-0.79 (m, 2H).

Examples 93, 94, 95, 96

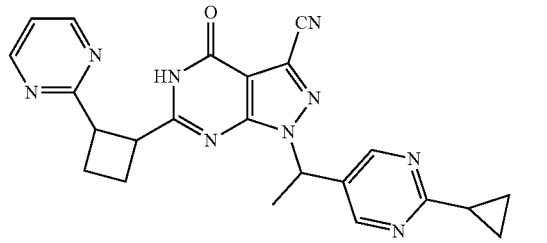

Isomer A

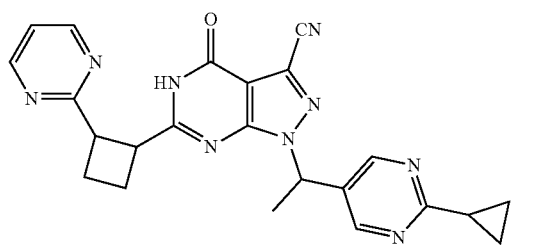

Isomer C

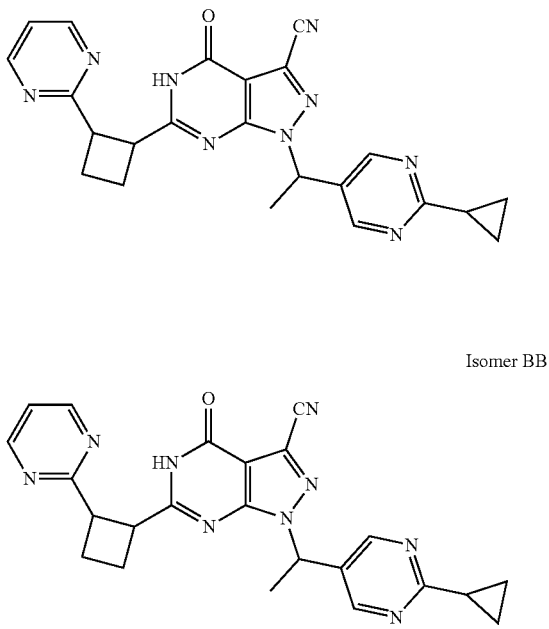

Isomer BA

Isomer BB 1-(1-(2-Cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile (Isomer A)—EXAMPLE 93

1-(1-(2-Cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile (Isomer C)—EXAMPLE 94

1-(1-(2-Cyclopropylpyrimidin-5-yl)ethyl)-4-oxo-6-(2-(pyrimidin-2-yl)cyclobutyl-4,5-dihydro-1H-pyrazolo[3,4-d]pyrimidine-3-carbonitrile (Isomer BA)—EXAMPLE 95

1-(1-(2-Cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile (Isomer BB)—EXAMPLE 96

Step A: To a solution of 1-(2-cyclopropylpyrimidin-5-yl)ethanone (1.00 g, 6.17 mmol) in MeOH (10 mL) was added NaBH4 (0.467 g, 12.33 mmol) at 0° C. The reaction mixture was stirred at room temperature for 2 h. The reaction was then quenched by the addition of 2 mL of water. The residue was diluted with water, and was extracted with ethyl acetate (3×60 mL). The combined organic layer was washed with brine (3×50 mL), dried over anhydrous Na$_2$SO$_4$ and filtered. The filtrate was concentrated under reduced pressure, the residue was purified by a silica gel column chromatography, eluted with gradient 0%-50% ethyl acetate in petroleum ether. The fractions containing desired product were combined and concentrated to afford 1-(2-cyclopropylpyrimidin-5-yl)ethanol. LCMS (ES, m/z): 165.2 [M+H]$^+$.

Step B: To a solution of 1-(2-cyclopropylpyrimidin-5-yl)ethanol (0.150 g, 0.913 mmol) and 4-isopropoxy-6-(2-(pyrimidin-2-yl)cyclobutyl)-1H-pyrazolo[3,4-d]pyrimidine-3-carbonitrile (0.306 g, 0.913 mmol) in toluene (1.5 mL) was added triphenylphosphine (0.599 g, 2.284 mmol) and diisopropyl azodicarboxylate (0.355 mL, 1.827 mmol) at room temperature. The reaction solution was stirred at room temperature for 3 h. The resulting reaction was concentrated under reduced pressure and was extracted with ethyl acetate (3×50 mL). The combined organic layer was washed with brine (3×30 mL), dried over anhydrous Na$_2$SO$_4$ and filtered. The filtrate was concentrated under reduced pressure, the residue was purified by a silica gel column chromatography, eluted with gradient 0%-70% ethyl acetate in petroleum ether. The fractions containing desired product were combined and concentrated to afford 1-(1-(2-cyclopropylpyrimidin-5-yl)ethyl)-4-isopropoxy-6-(2-(pyrimidin-2-yl)cyclobutyl)-1H-pyrazolo[3,4-d]pyrimidine-3-carbonitrile. LCMS (ES, m/z): 482.3 [M+H]$^+$.

Step C: A solution of 1-(1-(2-cyclopropylpyrimidin-5-yl)ethyl)-4-isopropoxy-6-(2-(pyrimidin-2-yl)cyclobutyl)-1H-pyrazolo[3,4-d]pyrimidine-3-carbonitrile (0.350 g, 0.00 mmol) in TFA (4 mL) was stirred at room temperature for 16 h. The resulting solution was filtered and the filtrate was purified by Prep-HPLC with the following conditions: Column: XBridge C18 OBD Prep Column 100 Å, 10 μm, 19 mm×250 mm; Mobile Phase A: Water (20 mmol/L NH$_4$HCO$_3$), Mobile Phase B: ACN; Flow rate: 25 mL/min; Gradient: 33% B to 55% B in 8 min; 254/210 nm; to afford 1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile. LCMS (ES, m/z): 440.3 [M+H]$^+$.

Step D: 1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile (0.210 g, 0.478 mmol) was separated by PREP CHIRAL HPLC with the following conditions: Column: CHIRALPAK IG, 20*250 mm, 5 um; Mobile Phase A:Hex-HPLC, Mobile Phase B: EtOH-HPLC; Flow rate: 20 mL/min; Gradient: 40 B to 40 B in 29 min; 220/254 nm; RT1:16.751 min; RT2:18.655 min; RT:23.755 min. The fractions containing desired product were combined and concentrated under vacuum to afford isomer A 1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile (peak 1), isomer B 1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile (peak 2) and isomer C 1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile (peak 3). Isomer A (Peak 1, EXAMPLE 93): LCMS (ES, m/z): 440.3 [M+H]$^+$. $^1$H NMR (400 MHz, CDCl$_3$) δ 12.34 (s, 1H), 8.85 (d, J=4.9 Hz, 2H), 8.74 (s, 2H), 7.37-7.30 (m, 1H), 6.11 (q, J=7.1 Hz, 1H), 3.93 (q, J=9.4 Hz, 1H), 3.80 (q, J=9.5 Hz, 1H), 2.77-2.62 (m, 1H), 2.59-2.48 (m, 2H), 2.38-2.25 (m, 2H), 2.05 (d, J=7.3 Hz, 3H), 1.22-1.08 (m, 4H). Isomer C (Peak 3, EXAMPLE 94): LCMS (ES, m/z): 440.3 [M+H]$^+$. $^1$H NMR (400 MHz, CDCl$_3$) δ 12.29 (s, 1H), 8.85 (d, J=5.0 Hz, 2H), 8.69 (s, 2H), 7.37-7.30 (m, 1H), 6.12 (q, J=7.2 Hz, 1H), 3.95 (q, J=9.5 Hz, 1H), 3.78 (q, J=9.4 Hz, 1H), 2.81-2.66 (m, 1H), 2.59-2.48 (m, 2H), 2.40-2.20 (m, 2H), 2.05 (d, J=7.2 Hz, 3H), 1.20-1.06 (m, 4H).

Step E: Isomer B (peak 2 of step D) 1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile (90 mg, 0.205 mmol) was separated by PREP CHIRAL HPLC with the following conditions: Column: (R,R)-WHELK-O1-Kromasil, 5 cm*25 cm(5 um); Mobile Phase A:Hex-HPLC, Mobile Phase B: EtOH-HPLC; Flow rate: 20 mL/min; Gradient: 30 B to 30 B in 22 min; 254/220 nm. The collected fractions were combined and concentrated under vacuum to afford the faster eluting isomer BA 1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile. The collected fractions were combined and concentrated under vacuum to afford the slower eluting isomer BB 1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile. Isomer BA (Faster eluting, Peak 1, EXAMPLE 95): LCMS (ES, m/z): 440.3 [M+H]$^+$. $^1$H NMR (400 MHz, CDCl$_3$) δ 12.34 (s, 1H), 8.85 (d, J=4.9 Hz, 2H), 8.73 (s, 2H), 7.37-7.30 (m, 1H), 6.11 (q, J=7.2 Hz, 1H), 3.93 (q, J=9.4 Hz, 1H), 3.80 (q, J=9.5 Hz, 1H), 2.76-2.62 (m, 1H), 2.59-2.48 (m, 2H), 2.40-2.23 (m, 2H), 2.04 (d, J=7.2 Hz, 3H), 1.21-1.07 (m, 4H). Isomer BB (Slower eluting, Peak 2, EXAMPLE 96): LCMS (ES, m/z): 440.3 [M+H]$^+$. $^1$H NMR (400 MHz, CDCl$_3$) δ 12.28 (s, 1H), 8.85 (d, J=5.0 Hz, 2H), 8.69 (s, 2H), 7.37-7.30 (m, 1H), 6.12 (q, J=7.2 Hz, 1H), 3.95 (q, J=9.5 Hz, 1H), 3.78 (q, J=9.4 Hz, 1H), 2.73 (p, J=10.3 Hz, 1H), 2.59-2.48 (m, 2H), 2.39-2.22 (m, 2H), 2.05 (d, J=7.2 Hz, 3H), 1.20-1.06 (m, 4H).

Example 97

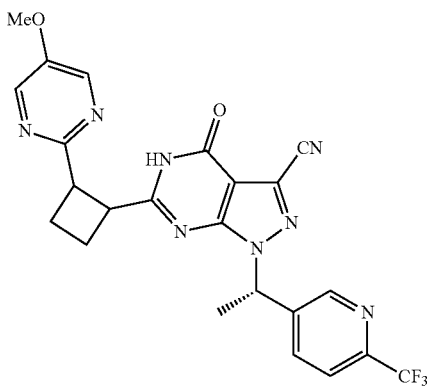 [SMILES: COc1cnc(C2CCC2c2nc3c(c(C#N)nn3[C@@H](C)c3ccc(C(F)(F)F)nc3)c(=O)[nH]2)nc1]

6-(2-(5-Methoxypyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile Step A: To a solution of 3-((benzyloxy)methyl)-6-(2-(5-methoxypyrimidin-2-yl)cyclobutyl)-1-((S)-1-(6-(trifluoromethyl)pyridin-3-yl)ethyl)-1H-pyrazolo[3,4-d]pyrimidin-4(5H)-one (0.05 g, 0.085 mmol) in DCM (2 mL) was added boron trichloride (0.34 mL, 0.34 mmol) at −78° C. The reaction solution was stirred −40° C. for 2 h. The resulted solution was quenched with MeOH at −78° C. and concentrated under vacuum. The residue was purified by Column: XBridge C18 OBD Prep Column, 100 Å, 5 μm, 19 mm×250 mm; Mobile Phase A: water with 20 mmol/L NH$_4$HCO$_3$, Mobile Phase B: ACN; Flow rate: 20 mL/min; Gradient: 20% B to 80% B in 9 min; 254/210 nm. The fractions containing desired product were combined and concentrated to afford 3-(hydroxymethyl)-6-(2-(5-methoxypyrimidin-2-yl)cyclobutyl)-1-((S)-1-(6-(trifluoromethyl)pyridin-3-yl)ethyl)-1H-pyrazolo[3,4-d]pyrimidin-4(5H)-one. LCMS (ES, m/z): 502.2 [M+H]$^+$.

Step B: To a solution of 3-(hydroxymethyl)-6-(2-(5-methoxypyrimidin-2-yl)cyclobutyl)-1-((S)-1-(6-(trifluoromethyl)pyridin-3-yl)ethyl)-1H-pyrazolo[3,4-d]pyrimidin-4(5H)-one (0.10 g, 0.20 mmol) in DCM (4 mL) was added Dess-Martin Periodinane (0.09 g, 0.20 mmol). The reaction mixture was stirred at room temperature for 1 h. The reaction mixture was quenched with aq. NaHCO3 (sat., 3 mL) and aq. Na2S2O3 (sat., 3 mL). The resulting mixture was stirred for 30 min. The reaction mixture was extracted with DCM (3×10 mL). The combined organic layers was dried over anhydrous Na2SO4 and filtered. The filtrate was concentrated under vacuum. The residue was purified by silica gel column chromatography, eluted with gradient 50%-100% EtOAc in Petroleum ether. The fractions containing desired product were combined and concentrated under vacuum to afford 6-(2-(5-methoxypyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbaldehyde. LCMS (ES, m/z): 500.1 [M+H]$^+$.

Step C: To a solution of 6-(2-(5-methoxypyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbaldehyde (45.00 mg, 0.090 mmol) in ACN (0.5 mL) at room temperature under N$_2$ were added hydroxylamine hydrochloride (9.39 mg, 0.14 mmol) and DIPEA (0.063 mL, 0.36 mmol). The reaction mixture was stirred at room temperature for 5 min. A 50% solution of 2,4,6-tripropyl-1,3,5,2,4,6-trioxatriphosphinane 2,4,6-trioxide (115 mg, 0.36 mmol) was added dropwise to the reaction mixture. The reaction mixture was stirred at 80° C. for 8 h. The solvent was removed under vacuum. The residue was purified by Prep-HPLC with the following conditions: column: X Bridge BEH C18 OBD Prep Column, 5 μm, 19 mm×250 mm; Mobile Phase A: water with 10 mmol/L NH$_4$HCO$_3$ and 0.1% NH$_3$.H$_2$O, Mobile Phase B: ACN; Flow rate: 20 mL/min; Gradient: 20% B to 70% B in 9 min; 254/210 nm. The fractions containing desired product were combined and concentrated under vacuum to afford 6-(2-(5-methoxypyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile. LCMS (ES, m/z): 497.2 [M+H]$^+$.

TABLE 4

| Ex. | Structure | Name | Exact Mass [M + H]⁺ | Chiral HPLC Condition; Peak # |
|---|---|---|---|---|
| 98 | 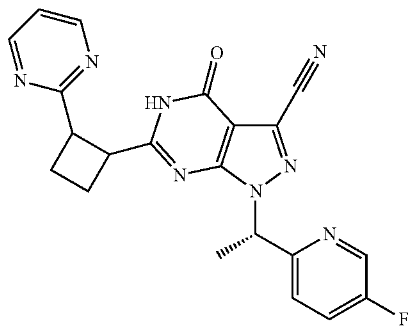 [SMILES: C[C@@H](c1ccc(F)cn1)n1nc(C#N)c2c(=O)[nH]c(C3CCC3c3ncccn3)nc21] | 1-((S)-1-(5-fluoropyridin-2-yl)ethyl)-4-oxo-6-(2-(pyrimidin-2-yl)cyclobutyl)-4,5-dihydro-1H-pyrazolo[3,4-d]pyrimidine-3-carbonitrile | 417.2 | From final reaction mixture the first eluted peak using Condition J was further separated by Condition H; 1 |
| 99 | 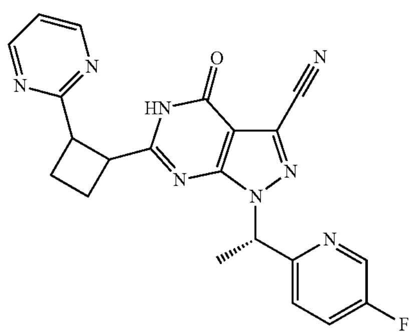 [SMILES: C[C@@H](c1ccc(F)cn1)n1nc(C#N)c2c(=O)[nH]c(C3CCC3c3ncccn3)nc21] | 1-((S)-1-(5-fluoropyridin-2-yl)ethyl)-4-oxo-6-(2-(pyrimidin-2-yl)cyclobutyl)-4,5-dihydro-1H-pyrazolo[3,4-d]pyrimidine-3-carbonitrile | 417.2 | From final reaction mixture the first eluted peak using Condition J was further separated by Condition H; 2 |
| 100 | 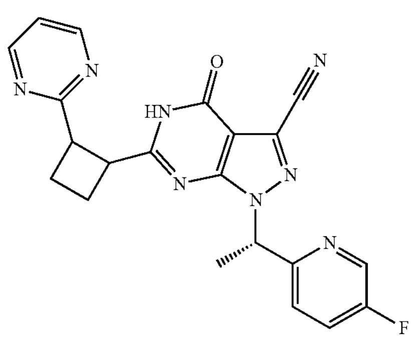 [SMILES: C[C@@H](c1ccc(F)cn1)n1nc(C#N)c2c(=O)[nH]c(C3CCC3c3ncccn3)nc21] | 1-((S)-1-(5-fluoropyridin-2-yl)ethyl)-4-oxo-6-(2-(pyrimidin-2-yl)cyclobutyl)-4,5-dihydro-1H-pyrazolo[3,4-d]pyrimidine-3-carbonitrile | 417.2 | Condition J; 2 |
| 101 | 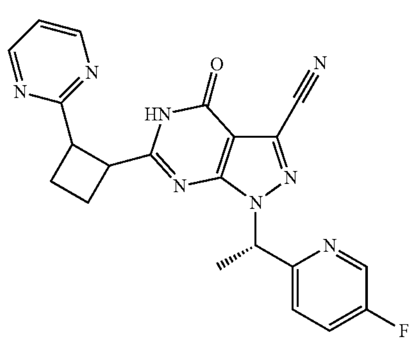 [SMILES: C[C@@H](c1ccc(F)cn1)n1nc(C#N)c2c(=O)[nH]c(C3CCC3c3ncccn3)nc21] | 1-((S)-1-(5-fluoropyridin-2-yl)ethyl)-4-oxo-6-(2-(pyrimidin-2-yl)cyclobutyl)-4,5-dihydro-1H-pyrazolo[3,4-d]pyrimidine-3-carbonitrile | 417.2 | Condition J; 3 |

TABLE 4-continued

| Ex. | Structure | Name | Exact Mass [M + H]+ | Chiral HPLC Condition; Peak # |
|---|---|---|---|---|
| 102 | 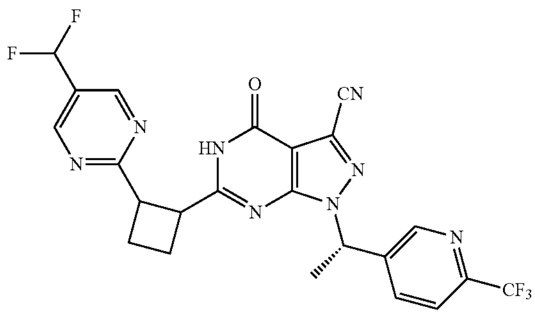 [SMILES: C[C@@H](c1ccc(C(F)(F)F)nc1)n1nc(C#N)c2c(=O)[nH]c(C3CCC3c3ncc(C(F)F)cn3)nc21] | 6-(2-(5-(difluoromethyl)-pyrimidin-2-yl)cyclo-butyl)-4-oxo-1-((S)-1-(6-(trifluoromethyl)pyridin-3-yl)ethyl)-4,5-dihydro-1H-pyrazolo[3,4-d]pyrimidine-3-carbonitrile | 517.1 | Condition B; 1 |
| 103 | 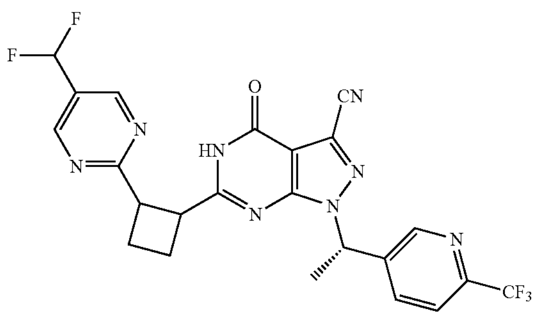 [SMILES: C[C@@H](c1ccc(C(F)(F)F)nc1)n1nc(C#N)c2c(=O)[nH]c(C3CCC3c3ncc(C(F)F)cn3)nc21] | 6-(2-(5-(difluoromethyl)-pyrimidin-2-yl)cyclo-butyl)-4-oxo-1-((S)-1-(6-(trifluoromethyl)pyridin-3-yl)ethyl)-4,5-dihydro-1H-pyrazolo[3,4-d]pyrimidine-3-carbonitrile | 517.1 | From final reaction mixture the second eluted peak on Condition B was further separated by Condition C; 1 |
| 104 | 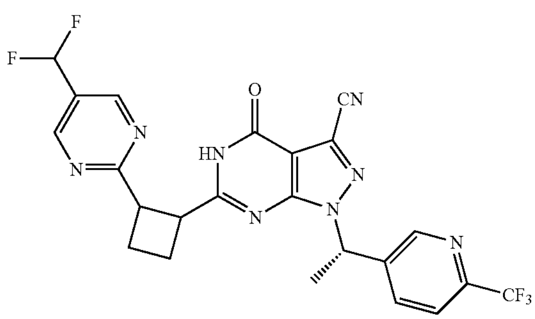 [SMILES: C[C@@H](c1ccc(C(F)(F)F)nc1)n1nc(C#N)c2c(=O)[nH]c(C3CCC3c3ncc(C(F)F)cn3)nc21] | 6-(2-(5-(difluoromethyl)-pyrimidin-2-yl)cyclo-butyl)-4-oxo-1-((S)-1-(6-(trifluoromethyl)pyridin-3-yl)ethyl)-4,5-dihydro-1H-pyrazolo[3,4-d]pyrimidine-3-carbonitrile | 517.1 | From final reaction mixture the second eluted peak on Condition B was further separated by Condition C; 2 |
| 105 | 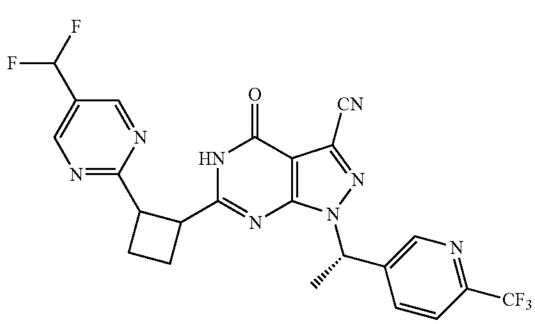 [SMILES: C[C@@H](c1ccc(C(F)(F)F)nc1)n1nc(C#N)c2c(=O)[nH]c(C3CCC3c3ncc(C(F)F)cn3)nc21] | 6-(2-(5-(difluoromethyl)-pyrimidin-2-yl)cyclo-butyl)-4-oxo-1-((S)-1-(6-(trifluoromethyl)pyridin-3-yl)ethyl)-4,5-dihydro-1H-pyrazolo[3,4-d]pyrimidine-3-carbonitrile | 517.1 | Condition B; 3 |

TABLE 4-continued

| Ex. | Structure | Name | Exact Mass [M + H]+ | Chiral HPLC Condition; Peak # |
|---|---|---|---|---|
| 106 | 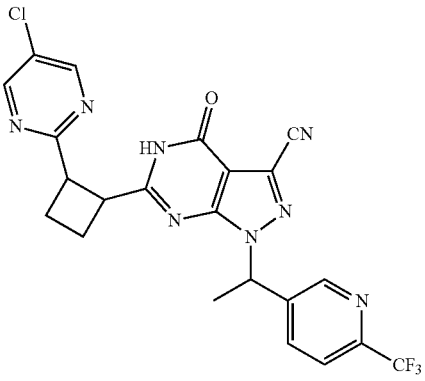 Isomer A | 6-(2-(5-chloropyrimidin-2-yl)cyclobutyl)-4-oxo-1-(1-(6-(trifluoromethyl)-pyridin-3-yl)ethyl)-4,5-dihydro-1H-pyrazolo[3,4-d]pyrimidine-3-carbonitrile | 501.1 | Condition B; 1 |
| 107 | 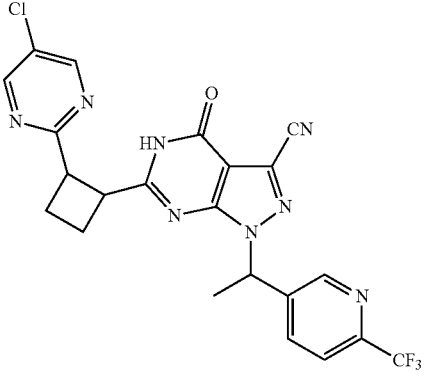 Isomer BA | 6-(2-(5-chloropyrimidin-2-yl)cyclobutyl)-4-oxo-1-(1-(6-(trifluoromethyl)-pyridin-3-yl)ethyl)-4,5-dihydro-1H-pyrazolo[3,4-d]pyrimidine-3-carbonitrile | 501.1 | From final reaction mixture the second eluted peak on Condition B was further separated by Condition C; 1 |
| 108 | 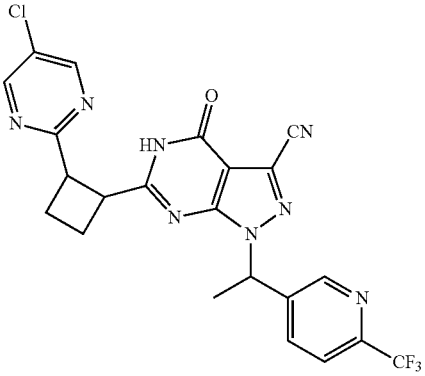 Isomer BB | 6-(2-(5-chloropyrimidin-2-yl)cyclobutyl)-4-oxo-1-(1-(6-trifluoromethyl)-pyridin-3-yl)ethyl)-4,5-dihydro-1H-pyrazolo[3,4-d]pyrimidine-3-carbonitrile | 501.1 | From final reaction mixture the second eluted peak on Condition B was further separated by Condtion C; 2 |

TABLE 4-continued

| Ex. | Structure | Name | Exact Mass [M + H]+ | Chiral HPLC Condition; Peak # |
|---|---|---|---|---|
| 109 | Isomer C | 6-(2-(5-chloropyrimidin-2-yl)cyclobutyl)-4-oxo-1-(1-(6-(trifluoromethyl)-pyridin-3-yl)ethyl)-4,5-dihydro-1H-pyrazolo[3,4-d]pyrimidine-3-carbonitrile | 501.1 | Condition B; 3 |

The following compounds were prepared according to the general procedure provided in the examples and procedures herein using known or prepared starting materials, as described in the reaction schemes and examples herein, such as described for Example 97, using appropriate starting materials and purification conditions. The requisite starting materials are either prepared as described in the intermediates section, commercially available, or may be prepared from commercially available reagents using conventional reactions well known in the art without undue experimentation.

Examples 110-111

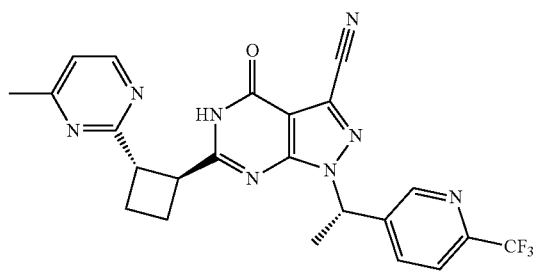

Example 110

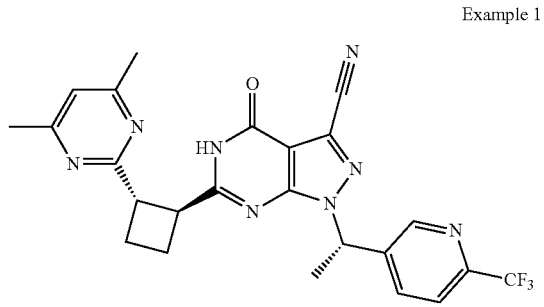

Example 111

6-((1S,2S)-2-(4-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (EXAMPLE 110) and 6-((1S,2S)-2-(4,6-dimethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (Example 111)

To a solution of 6-((1S,2S)-2-(4-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (9 mg, 0.02 mmol), Ir(dF (CF$_3$) ppy)$_2$(dtbbpy)]PF$_6$ photocatalyst (1.09 mg, 0.96 μmol, 5 mol %) in CAN (106 μL)/TFA (106 μL), tert-butylperacetate (10.8 μL, 0.058 mmol) was added and the mixture was stirred at room temperature for 12 hours under blue LED lights (Merck G2 photoreactor, 82% LED intensity). After 12 hours, LCMS showed some amount of product formation. Another round of tert-butylperacetate (10.8 μL, 0.058 mmol) was added and the solution was stirred at room temperature for further 12 hours under blue LED lights. LCMS indicated formation of the bis-methylated product along with significant amount of the mono-methylated product. The reaction mixture was concentrated under reduced pressure, dissolved in 1.5 mL DMSO, filtered through a 0.45 micron HPLC frit and purified by reverse phase chromatography (Column: Waters Xbridge C18 Column, 130 Å, 19×150 mm, 5 um, Flow=25 ml/min, linear gradient: starting with 30% CAN/water to 70% CAN/water buffered with 0.16% ammonium hydroxide (pH 10)) to give the product EXAMPLE 110 and EXAMPLE 111. EXAMPLE 110: $^1$H NMR (500 MHz, CDCl$_3$) δ 13.03 (s, 1H), 8.89 (s, 1H), 8.67 (d, J=5.1 Hz, 1H), 8.06 (d, J=8.1 Hz, 1H), 7.74 (d, J=8.2 Hz, 1H), 7.17 (d, J=5.0 Hz, 1H), 6.27 (q, J=7.1 Hz, 1H), 3.88 (q, J=9.6 Hz, 1H), 3.77 (q, J=9.4 Hz, 1H), 2.68 (s, 3H), 2.61 (q, J=9.8 Hz, 1H), 2.51 (dt, J=9.6, 16.7 Hz, 2H), 2.34 (d, J=8.3 Hz, 1H), 2.07 (d, J=7.1 Hz, 3H). LCMS (ES, m/z): [M+H]$^+$: 481.4. EXAMPLE 111: $^1$H NMR (500 MHz, CDCl$_3$) δ 13.03 (br s, 1H), 8.90 (s, 1H), 8.05 (d, J=6.5 Hz, 1H), 7.73 (d, J=8.2 Hz, 1H), 7.04 (s, 1H), 6.35 (m, 1H), 4.09-3.48 (m, 2H), 2.62 (s, 6H), 2.53-2.44 (m, 2H), 2.34 (d, J=8.0 Hz, 1H), 2.06 (d, J=7.1 Hz, 3H). LCMS (ES, m/z): [M+H]$^+$: 495.4

Example 112

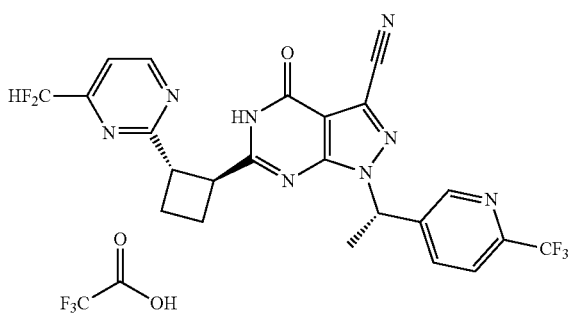

6-((1S,2S)-2-(4-(difluoromethyl)pyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile trifluoroacetic acid salt To a solution of 6-((1S,2S)-2-(4-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile (9 mg, 0.02 mmol), 10-methyl-9-(2,4,6-trimethylphenyl) acridinium tetrafluoroborate photocatalyst (0.38 mg, 0.96 μmol, 5 mol %), zinc difluoromethanesulfinate (17.11 mg, 0.058 mmol) in CAN (150 μL)/water (150 μL), potassium persulfate (15.65 mg, 0.058 mmol) and TFA (1.48 μL, 0.02 mmol) were added and the mixture was stirred at room temperature for 12 hours under blue LED lights (Merck G2 photoreactor, 91% LED intensity). After 12 hours, LCMS showed some amount of product formation. Another round of zinc difluoromethane-sulfinate (17.11 mg, 0.058 mmol) and potassium persulfate (15.65 mg, 0.058 mmol) were added and the solution was stirred at room temperature for further 12 hours under blue LED lights (Merck G2 photoreactor, 100% LED intensity). The reaction mixture was concentrated under reduced pressure, dissolved in 1.5 mL DMSO, filtered through a 0.45 micron HPLC frit and purified by reverse phase chromatography (Column: Waters CSH C18 Column, 130 Å, 19×150 mm, 5 um, Flow=25 ml/min, linear gradient: starting with 40% CAN/water to 85% CAN/water buffered with 0.1% TFA) to give the product EXAMPLE 112 TFA salt. $^1$H NMR (500 MHz, CDCl$_3$) δ 11.96 (s, 1H), 8.06 (dd, J=8.2, 1.9 Hz, 1H), 7.74 (d, J=8.2 Hz, 1H), 7.62 (d, J=5.1 Hz, 1H), 6.66 (t, J=54.5 Hz, 1H), 6.26 (q, J=7.1 Hz, 1H), 3.98 (q, J=9.4 Hz, 1H), 3.83 (q, J=9.5 Hz, 1H), 2.68 (p, J=10.0 Hz, 1H), 2.60-2.48 (m, 2H), 2.37 (q, J=8.4 Hz, 1H), 2.07 (d, J=7.2 Hz, 3H). LCMS (ES, m/z): [M+H]$^+$: 517.4

TABLE 5

| Example | Structure | Name | LCMS (M + H)$^+$ |
|---|---|---|---|
| 113 | 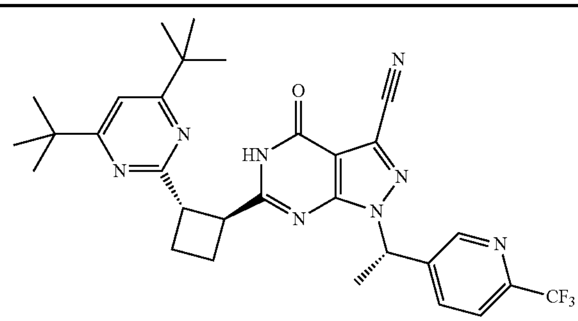 | 6-((1S,2S)-2-(4,6-di-tert-butylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile | 579.4 |
| 114 | 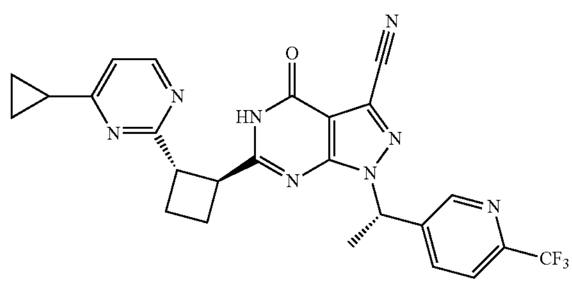 [SMILES: C[C@@H](c1ccc(C(F)(F)F)nc1)n1nc(C#N)c2c(=O)[nH]c([C@H]3CC[C@@H]3c3nccc(C4CC4)n3)nc21] | 6-((1S,2S)-2-(4-cyclopropyl-pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile | 507.3 |
| 115 | 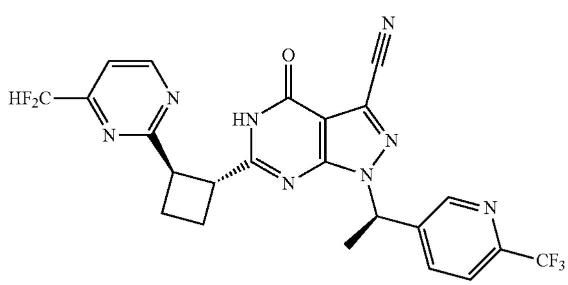 | 6-((1R,2R)-2-(4-(difluoromethyl)pyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile | 517.5 |

TABLE 5-continued

| Example | Structure | Name | LCMS (M + H)+ |
|---|---|---|---|
| 116 | 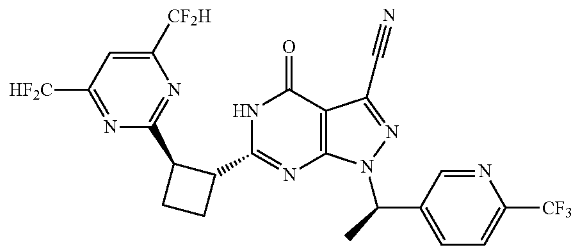 | 6-((1R,2R)-2-(4,6-bis(difluoromethyl)pyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile | 567.4 |
| 117 | 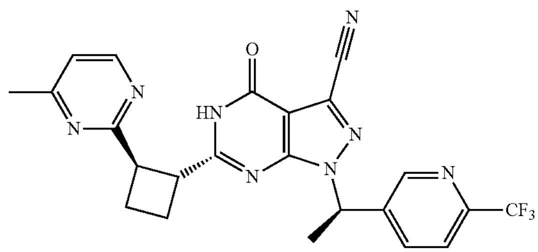 | 6-((1R,2R)-2-(4-methylpyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile | 481.2 |
| 118 | 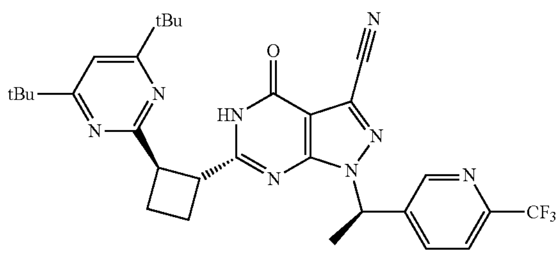 | 6-((1R,2R)-2-(4,6-di-tert-butylpyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile | 579.5 |
| 119 | 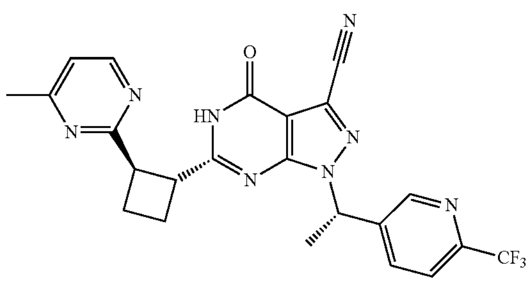 | 6-((1R,2R)-2-(4-methylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile | 481.3 |
| 120 | 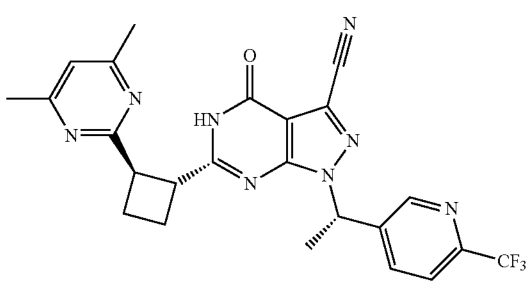 | 6-((1R,2R)-2-(4,6-dimethylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile | 495.3 |

TABLE 5-continued

| Example | Structure | Name | LCMS (M + H)+ |
|---|---|---|---|
| 121 | 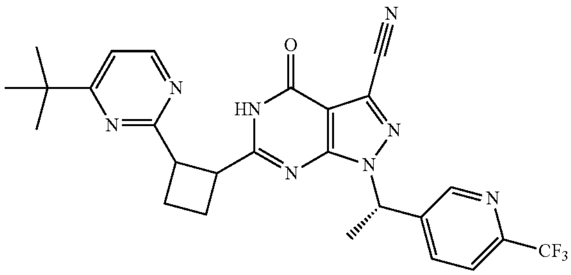 [SMILES: C[C@@H](c1ccc(C(F)(F)F)nc1)n1nc(C#N)c2c(=O)[nH]c(C3CCC3c3nccc(C(C)(C)C)n3)nc21] | 6-(2-(4-(tert-butyl)pyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile | 523.4 |
| 122 | 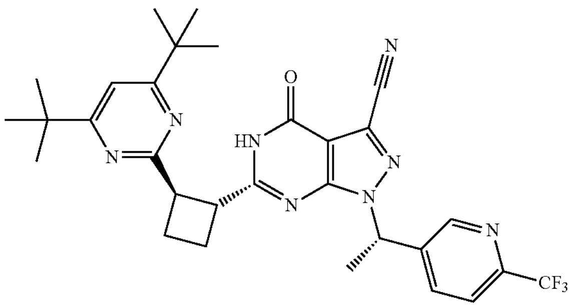 | 6-((1R,2R)-2-(4,6-di-tert-butylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile | 579.5 |
| 123 | 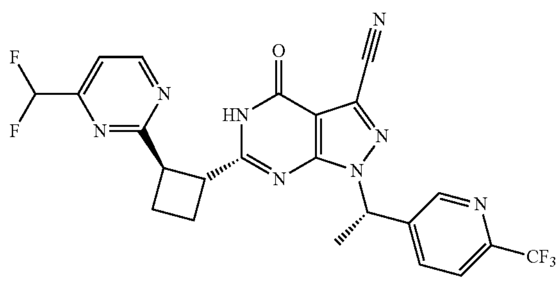 | 6-((1R,2R)-2-(4-(difluoromethyl)pyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile | 517.3 |
| 124 | 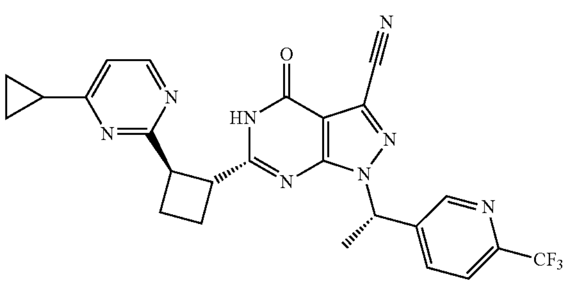 | 6-((1R,2R)-2-(4-cyclopropylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile | 507.1 |

The following compounds were prepared according to the general procedure provided in the examples and procedures herein using known or prepared starting materials, as described in the reaction schemes and examples herein, such as described for Examples 110-112, using appropriate starting materials and purification conditions. The compounds were isolated as the 2,2,2-trifluoroacetate salt. The requisite starting materials are either prepared as described in the intermediates section, commercially available, or may be prepared from commercially available reagents using conventional reactions well known in the art without undue experimentation.

TABLE 6

| Example | PDE9 IMAP Ki (nM) |
|---|---|
| 1 | 27.3 |
| 2 | 0.2 |
| 3 | 32.1 |
| 4 | 4.8 |
| 5 | 15.9 |
| 6 | 0.1 |
| 7 | 2.8 |
| 8 | 4.7 |
| 9 | 123.7 |
| 10 | 4.8 |

TABLE 6-continued

| Example | PDE9 IMAP Ki (nM) |
|---|---|
| 11 | 44.3 |
| 12 | 9.3 |
| 13 | 0.1 |
| 14 | 1.5 |
| 15 | 109.5 |
| 16 | 3 |
| 17 | 0.4 |
| 18 | 11.3 |
| 19 | 12.1 |
| 20 | 0.01 |
| 21 | 4.5 |
| 22 | 1.8 |
| 23 | 25 |
| 24 | 1.8 |
| 25 | 31.9 |
| 26 | 0.1 |
| 27 | 19.6 |
| 28 | 0.5 |
| 29 | 271.8 |
| 30 | 2.3 |
| 31 | 2.2 |
| 32 | 154.5 |
| 33 | 0.04 |
| 34 | 318.6 |
| 35 | 1.2 |
| 36 | 329.2 |
| 37 | 50.4 |
| 38 | >607.5 |
| 39 | >607.5 |
| 40 | 0.13 |
| 41 | 8 |
| 42 | >607.5 |
| 43 | 2 |
| 44 | 82.3 |
| 45 | 8.9 |
| 46 | 164.2 |
| 47 | 0.22 |
| 48 | 0.9 |
| 49 | 103.9 |
| 50 | >607.5 |
| 51 | >607.5 |
| 52 | 147.8 |
| 53 | 0.8 |
| 54 | >607.5 |
| 55 | 493.4 |
| 56 | 12.6 |
| 57 | 0.01 |
| 58 | 26.9 |
| 59 | 0.12 |
| 60 | 86.7 |
| 61 | 0.08 |
| 62 | 0.01 |
| 63 | 5.6 |
| 64 | >67.5 |
| 65 | >67.5 |
| 66 | >67.5 |
| 67 | >67.5 |
| 68 | >67.5 |
| 69 | >67.5 |
| 70 | >67.5 |
| 71 | >67.5 |
| 72 | 54.6 |
| 73 | 2 |
| 74 | 6.2 |
| 75 | 0.02 |
| 76 | 353.5 |
| 77 | 153.3 |
| 78 | 1.1 |
| 79 | 17.3 |
| 80 | 0.09 |
| 81 | 1.6 |
| 82 | 0.23 |
| 83 | 10.8 |
| 84 | 0.25 |
| 85 | >607 |
| 86 | >607 |
| 87 | 249.5 |
| 88 | 0.7 |
| 89 | 139.8 |
| 90 | 0.3 |
| 91 | 0.01 |
| 92 | 55.7 |
| 93 | 0.03 |
| 94 | 1.3 |
| 95 | 1.5 |
| 96 | 37.8 |
| 97 | 0.15 |
| 98 | 321.4 |
| 99 | 392.2 |
| 100 | 1.7 |
| 101 | 16 |
| 102 | 164.8 |
| 103 | 33.9 |
| 104 | 0.18 |
| 105 | 21.8 |
| 106 | 26.7 |
| 107 | 175.1 |
| 108 | 0.2 |
| 109 | 24 |
| 110 | 0.05 |
| 111 | 0.04 |
| 112 | 0.13 |
| 113 | 0.27 |
| 114 | 0.04 |
| 115 | 25.3 |
| 116 | 8.3 |
| 117 | 3.9 |
| 118 | 74.7 |
| 119 | 36.7 |
| 120 | 23.3 |
| 121 | 23.7 |
| 122 | 321.4 |
| 123 | 19.2 |
| 124 | 28.9 |

The following table shows representative data for the compounds of the Examples as PDE9 inhibitors as determined by the assays described herein. In this table, the PDE9 $K_i$ is a measure of the ability of the test compound to inhibit the action of the PDE9 enzyme. Such results are indicative of the intrinsic activity of the compounds for use as inhibitors of the PDE9 enzyme.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula I:

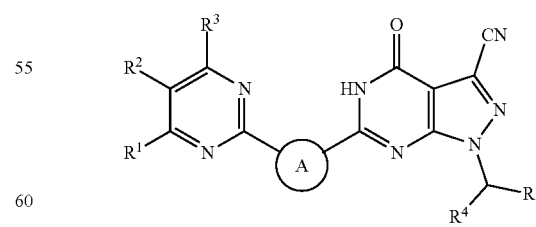

or a pharmaceutically acceptable salt thereof, wherein:
A is cyclobutyl, which is optionally substituted with one or more substituents independently selected from the group consisting of fluoro and methyl;

$R^1$, $R^2$ and $R^3$ are independently hydrogen, halogen, hydroxy, cyano, $C_{1-6}$alkyl, —O—$C_{1-6}$alkyl, $C_{2-6}$alkynyl, or $C_{3-6}$ cycloalkyl, wherein the $C_{1-6}$alkyl is optionally substituted with one or more substituents independently selected from the group consisting of hydroxy and fluoro, and further wherein the —O—$C_{1-6}$ alkyl is optionally substituted with one or more fluoro substituents;

$R^4$ is hydrogen, methyl, trifluoromethyl, hydroxymethyl, ethyl or carboxy;

$R^5$ is cyclohexyl, tetrahydropyranyl, phenyl, pyrazolyl, thiazolyl, pyridyl, pyridazinyl, pyrimidinyl, or pyrazinyl, wherein the cyclohexyl, tetrahydropyranyl, phenyl, pyrazolyl, thiazolyl, pyridyl, pyridazinyl, pyrimidinyl, or pyrazinyl is substituted with one or more substituents independently selected from the group consisting of $R^{1a}$, $R^{1b}$ and $R^{1c}$; and $R^{1a}$, $R^{1b}$ and $R^{1c}$ are independently hydrogen, halogen, hydroxy, cyano, $C_{1-6}$alkyl, —O—$C_{1-6}$alkyl, or $C_{3-6}$cycloalkyl, wherein the $C_{1-6}$alkyl is optionally substituted with one or more substituents independently selected from the group consisting of hydroxy and fluoro, and further wherein the —O—$C_{1-6}$alkyl is optionally substituted with one or more fluoro substituents;

with the proviso that the compound is other than:
1-((S)-1-(4-fluorophenyl)ethyl)-4-oxo-6((1S,2S)-2-(pyrmidin-2-yl) cyclobutyl)-4,5-dihydro-1H-pyrazolo[3,4-d]pyrimidine-3-carbonitrile;
4-oxo-6-((1S,2S-2-(pyrimidin-2-yl)cyclobutyl)-1-((S)-1-(6-(trifluoromethyl) pyridin-3-yl)ethyl)-4,5-dihydro-1H-pyrazolo[3,4-d]pyrimidine-3-carbonitrile;
6-((1S,2S)-2-(5-(difluoromethoxy)pyrimidin-2-yl)cyclobuty)-4-oxo-1-((S)-1-(6-(trifluoromethyl) pyridin-3-yl)ethyl)-4,5-dihydro-1H-pyrazolo[3,4-d]pyrimidine-3-carbonitrile;
6-((1S,2S)-2-(5-(fluoropyrimidin-2-yl)cyclobutyl)-4-oxo-1-((S)-1-(6-(trifluoromethyl) pyridin-3-yl)ethyl)-4,5-dihydro-1H-pyrazolo[3,4-d]pyrimidine-3-carbonitrile;
1-((S)-1-(2-cyclopropylpyrimidin-5-yl)ethyl)-4-oxo-6-((1S,2S)-2-(pyrimidin-2-yl) cyclobuty)-4,5-dihydro-1H-pyrazolo[3,4-d]pyrimidine-3-carbonitrile; or
6-((1S,2S)-2-(4-cyclopropylpyrimidin-2-yl)cyclobutyl)-4-oxo-1-((S)-1-(6-(trifluoromethyl) pyridin-3-yl)ethyl)-4,5-dihydro-1H-pyrazolo[3,4-d]pyrimidine-3-carbonitrile.

2. The compound of claim 1, wherein the compound is of formula Ia:

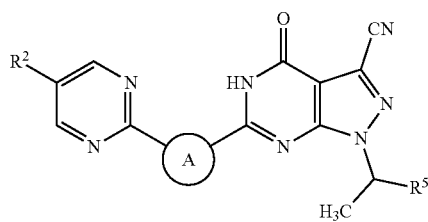

or a pharmaceutically acceptable salt thereof.

3. The compound of claim 1, or a pharmaceutically acceptable salt thereof, wherein A is cyclobutyl, which is optionally substituted with one or more fluoro substituents.

4. The compound of claim 1, or a pharmaceutically acceptable salt thereof, wherein $R^1$, $R^2$ and $R^3$ are independently hydrogen, halogen, hydroxy, cyano, $C_{1-6}$alkyl, —O—$C_{1-6}$alkyl, $C_{2-4}$alkynyl, or $C_{3-6}$cycloalkyl, wherein the $C_{1-6}$alkyl is optionally substituted with one or more substituents independently selected from the group consisting of hydroxy and fluoro, and further wherein the —O—$C_{1-6}$ alkyl is optionally substituted with one or more fluoro substituents.

5. The compound of claim 1, or a pharmaceutically acceptable salt thereof, wherein:
$R^1$ is hydrogen;
$R^2$ is hydrogen, fluoro, chloro, bromo, hydroxy, methyl, ethyl, isopropyl, tert-butyl, difluoromethyl, trifluoromethyl, methoxy, difluoromethoxy, trifluoromethoxy, ethynyl or cyclopropyl; and
$R^3$ is hydrogen.

6. The compound of claim 1, or a pharmaceutically acceptable salt thereof, wherein $R^4$ is methyl.

7. The compound of claim 1, or a pharmaceutically acceptable salt thereof, wherein;
$R^{1a}$ is hydrogen, fluoro, cyano, methyl, difluoromethyl, trifluoromethyl, difluoromethoxy, or trifluoromethoxy;
$R^{1b}$ is hydrogen; and
$R^{1c}$ is hydrogen.

8. A pharmaceutical composition comprising an inert carrier and a compound of claim 1, or a pharmaceutically acceptable salt thereof.

9. A method for inhibiting phosphodiesterase 9 activity in a mammalian patient, comprising administering to the mammalian patient a therapeutically effective amount of a compound of claim 1, or a pharmaceutically acceptable salt thereof.

10. The method of claim 9, wherein the mammalian patient has a disorder or disease associated with phosphodiesterase 9 dysfunction.

11. The method of claim 10, wherein the disorder or disease associated with phosphodiesterase 9 dysfunction is selected from the group consisting of drug induced psychosis, a psychotic disorder, a delusional disorder, a movement disorder, a neurodegenerative disorder and an anxiety disorder.

12. The method of claim 10, wherein the disorder or disease associated with phosphodiesterase 9 dysfunction is selected from the group consisting of hypertension, heart failure, a cardiovascular disease, a cerebrovascular disease, and a chronic kidney disease.

13. A compound selected from the group consisting of:
1-(1-(4-fluorophenyl)ethyl)-4-oxo-6-(2-(pyrimidin-2-yl) cyclobutyl)-4,5-dihydro-1H-pyrazolo[3,4-d]pyrimidine-3-carbonitrile;
1-((S)-1-(4-fluorophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;
1-((S)-1-(4-fluorophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;
1-((R)-1-(4-fluorophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;
1-((R)-1-(4-fluorophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;
4-oxo-6-(2-(pyrimidin-2-yl)cyclobutyl)-1-(1-(6-(trifluoromethyl)pyridin-3-yl)ethyl)-4,5-dihydro-1H-pyrazolo[3,4-d]pyrimidine-3-carbonitrile;
4-oxo-6-((1R,2R)-2-(pyrimidin-2-yl)cyclobutyl)-1-((S)-1-(6-(trifluoromethyl)pyridin-3-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(6-(trifluoromethyl)pyridin-3-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(6-(trifluoromethyl)pyridin-3-yl)ethyl)-4,5-dihydro-1H-pyrazolo[3,4-d]pyrimidine-3-carbonitrile;

4-oxo-6-((1 S, 2 S)-2-(pyrimidin-2-yl)cyclobutyl)-1-((R)-1-(6-(trifluoromethyl)pyridin-3-yl)ethyl)-4,5-dihydro-1H-pyrazolo[3,4-d]pyrimidine-3-carbonitrile;

4-oxo-6-(2-(pyrimidin-2-yl)cyclobutyl)-1-((6-(trifluoromethyl)pyridin-3-yl)methyl)-4,5-dihydro-1H-pyrazolo[3,4-d]pyrimidine-3-carbonitrile;

4-oxo-6-((1R,2R)-2-(pyrimidin-2-yl)cyclobutyl)-1-((6-(trifluoromethyl)pyridin-3-yl)methyl)-4,5-dihydro-1H-pyrazolo[3,4-d]pyrimidine-3-carbonitrile;

4-oxo-6-((1S,2S)-2-(pyrimidin-2-yl)cyclobutyl)-1-((6-(trifluoromethyl)pyridin-3-yl)methyl)-4,5-dihydro-1H-pyrazolo[3,4-d]pyrimidine-3-carbonitrile;

1-[1-(4-cyanophenyl)ethyl]-4-oxo-6-(2-pyrimidin-2-yl-cyclobutyl)-4,5-dihydro-1H-pyrazolo[3,4-d]pyrimidine-3-carbonitrile;

1-((S)-1-(4-cyanophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(4-cyanophenyl)ethyl)-4-oxo-6-((1 S,2S)-2-(pyrimidin-2-yl)cyclobutyl)-4,5-dihydro-1H-pyrazolo[3,4-d]pyrimidine-3-carbonitrile;

1-((R)-1-(4-cyanophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(4-cyanophenyl)ethyl)-4-oxo-6-((1 S, 2 S)-2-(pyrimidin-2-yl)cyclobutyl)-4,5-dihydro-1H-pyrazolo[3,4-d]pyrimidine-3-carbonitrile;

1-(1-(3,4-difluorophenyl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(3,4-difluorophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(3,4-difluorophenyl)ethyl)-4-oxo-6-((1 S,2S)-2-(pyrimidin-2-yl)cyclobutyl)-4,5-dihydro-1H-pyrazolo[3,4-d]pyrimidine-3-carbonitrile;

1-((R)-1-(3,4-difluorophenyl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(3,4-difluorophenyl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

4-oxo-6-[2-pyrimidin-2-ylcyclobutyl]-1-{1-[4-(trifluoromethyl)phenyl]ethyl}-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(4-(trifluoromethyl)phenyl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(4-(trifluoromethyl)phenyl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(4-(trifluoromethyl)phenyl)ethyl)-4,5-dihydro-1H-pyrazolo[3,4-d]pyrimidine-3-carbonitrile;

4-oxo-6-((1 S, 2 S)-2-(pyrimidin-2-yl)cyclobutyl)-1-((R)-1-(4-(trifluoromethyl)phenyl)ethyl)-4,5-dihydro-1H-pyrazolo[3,4-d]pyrimidine-3-carbonitrile;

4-oxo-6-[2-pyrimidin-2-ylcyclobutyl]-1-{1-[3-(trifluoromethyl)phenyl]ethyl}-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(3-(trifluoromethyl)phenyl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(3-(trifluoromethyl)phenyl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(3-(trifluoromethyl)phenyl)ethyl)-4,5-dihydro-1H-pyrazolo[3,4-d]pyrimidine-3-carbonitrile;

4-oxo-6-((1 S, 2 S)-2-(pyrimidin-2-yl)cyclobutyl)-1-((R)-1-(3-(trifluoromethyl)phenyl)ethyl)-4,5-dihydro-1H-pyrazolo[3,4-d]pyrimidine-3-carbonitrile;

4-oxo-6-(2-(pyrimidin-2-yl)cyclobutyl)-1-(1-(5-(trifluoromethyl)pyrazin-2-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(5-(trifluoromethyl)pyrazin-2-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(5-(trifluoromethyl)pyrazin-2-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(5-(trifluoromethyl)pyrazin-2-yl)ethyl)-4,5-dihydro-1H-pyrazolo[3,4-d]pyrimidine-3-carbonitrile;

4-oxo-6-((1 S, 2 S)-2-(pyrimidin-2-yl)cyclobutyl)-1-((R)-1-(5-(trifluoromethyl)pyrazin-2-yl)ethyl)-4,5-dihydro-1H-pyrazolo[3,4-d]pyrimidine-3-carbonitrile;

6-(2-(5-methylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1 S, 2 S)-2-(5-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-methylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-methylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

4-oxo-6-(2-(pyrimidin-2-yl)cyclobutyl)-1-(1-(2-(trifluoromethyl)pyrimidin-5-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(2-(trifluoromethyl)pyrimidin-5-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(2-(trifluoromethyl)pyrimidin-5-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(2-(trifluoromethyl)pyrimidin-5-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(2-(trifluoromethyl)pyrimidin-5-yl)ethyl)-4,5-dihydro-1H-pyrazolo[3,4-d]pyrimidine-3-carbonitrile;

1-(1-(6-(difluoromethyl)pyridin-3-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(6-(difluoromethyl)pyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(6-(difluoromethyl)pyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(6-(difluoromethyl)pyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(6-(difluoromethyl)pyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((S)-1-(6-(difluoromethyl)pyridin-3-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((S)-1-(6-(difluoromethyl)pyridin-3-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

1-((R)-1-(6-(difluoromethyl)pyridin-3-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((R)-1-(6-(difluoromethyl)pyridin-3-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

4-oxo-6-(2-(pyrimidin-2-yl)cyclobutyl)-1-(1-(tetrahydro-2H-pyran-4-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((S)-1-(tetrahydro-2H-pyran-4-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((S)-1-(tetrahydro-2H-pyran-4-yl)ethyl)-4,5-dihydro-1H-pyrazolo[3,4-d]pyrimidine-3-carbonitrile;

4-oxo-6-((1R,2R)-2-(pyrimidin-2-yl)cyclobutyl)-1-((R)-1-(tetrahydro-2H-pyran-4-yl)ethyl)-4,5-dihydro-1H-pyrazolo[3,4-d]pyrimidine-3-carbonitrile;

4-oxo-6-((1S,2S)-2-(pyrimidin-2-yl)cyclobutyl)-1-((R)-1-(tetrahydro-2H-pyran-4-yl)ethyl)-4,5-dihydro-1H-pyrazolo[3,4-d]pyrimidine-3-carbonitrile;

1-(1-(6-cyclopropylpyridin-3-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(6-cyclopropylpyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(6-cyclopropylpyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(6-cyclopropylpyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(6-cyclopropylpyridin-3-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((S)-1-(6-cyclopropylpyridin-3-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((S)-1-(6-cyclopropylpyridin-3-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

1-((R)-1-(6-cyclopropylpyridin-3-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((R)-1-(6-cyclopropylpyridin-3-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

6-(2-(5-bromopyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-bromopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-bromopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-bromopyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-bromopyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-(difluoromethoxy)pyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-(difluoromethoxy)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-(difluoromethoxy)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-(difluoromethoxy)pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-(difluoromethoxy)pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-ethylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-ethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1 S, 2 S)-2-(5-ethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-ethylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1 S, 2 S)-2-(5-ethylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

1-(1-(5-fluoropyridin-3-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(5-fluoropyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(5-fluoropyridin-3-yl)ethyl)-4-oxo-6-((1 S, 2 S)-2-(pyrimidin-2-yl)cyclobutyl)-4,5-dihydro-1H-pyrazolo[3,4-d]pyrimidine-3-carbonitrile;

1-((R)-1-(5-fluoropyridin-3-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(5-fluoropyridin-3-yl)ethyl)-4-oxo-6-((1 S, 2 S)-2-(pyrimidin-2-yl)cyclobutyl)-4,5-dihydro-1H-pyrazolo[3,4-d]pyrimidine-3-carbonitrile;

1-(1-(1-methyl-1H-pyrazol-4-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(1-methyl-1H-pyrazol-4-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;
1-((S)-1-(1-methyl-1H-pyrazol-4-yl)ethyl)-4-oxo-6-((1S,2 S)-2-(pyrimidin-2-yl)cyclobutyl)-4,5-dihydro-1H-pyrazolo[3,4-d]pyrimidine-3-carbonitrile;
1-((R)-1-(1-methyl-1H-pyrazol-4-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;
1-((R)-1-(1-methyl-1H-pyrazol-4-yl)ethyl)-4-oxo-6-((1 S, 2 S)-2-(pyrimidin-2-yl)cyclobutyl)-4,5-dihydro-1H-pyrazolo[3,4-d]pyrimidine-3-carbonitrile;
1-(1-(6-cyclopropylpyridin-3-yl)ethyl)-6-(2-(5-fluoropyrimidin-2-yl)cyclobutyl)-4-oxo-4,5-dihydro-1H-pyrazolo[3,4-d]pyrimidine-3-carbonitrile;
1-((S)-1-(6-cyclopropylpyridin-3-yl)ethyl)-6-((1R,2R)-2-(5-fluoropyrimidin-2-yl)cyclobutyl)-4-oxo-4,5-dihydro-1H-pyrazolo[3,4-d]pyrimidine-3-carbonitrile;
1-((S)-1-(6-cyclopropylpyridin-3-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile;
1-((R)-1-(6-cyclopropylpyridin-3-yl)ethyl)-6-((1R,2R)-2-(5-fluoropyrimidin-2-yl)cyclobutyl)-4-oxo-4,5-dihydro-1H-pyrazolo[3,4-d]pyrimidine-3-carbonitrile;
1-((R)-1-(6-cyclopropylpyridin-3-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile;
4-oxo-6-(2-(pyrimidin-2-yl)cyclobutyl)-1-(1-(2-(trifluoromethyl)thiazol-5-yl)ethyl)-4,5-dihydro-1H-pyrazolo[3,4-d]pyrimidine-3-carbonitrile;
4-oxo-6-((1R,2R)-2-(pyrimidin-2-yl)cyclobutyl)-1-((S)-1-(2-(trifluoromethyl)thiazol-5-yl)ethyl)-4,5-dihydro-1H-pyrazolo[3,4-d]pyrimidine-3-carbonitrile;
4-oxo-6-((1S,2S)-2-(pyrimidin-2-yl)cyclobutyl)-1-((S)-1-(2-(trifluoromethyl)thiazol-5-yl)ethyl)-4,5-dihydro-1H-pyrazolo[3,4-d]pyrimidine-3-carbonitrile;
4-oxo-6-((1R,2R)-2-(pyrimidin-2-yl)cyclobutyl)-1-((R)-1-(2-(trifluoromethyl)thiazol-5-yl)ethyl)-4,5-dihydro-1H-pyrazolo[3,4-d]pyrimidine-3-carbonitrile;
4-oxo-6-((1S,2S)-2-(pyrimidin-2-yl)cyclobutyl)-1-((R)-1-(2-(trifluoromethyl)thiazol-5-yl)ethyl)-4,5-dihydro-1H-pyrazolo[3,4-d]pyrimidine-3-carbonitrile;
1-(1-(2-cyclopropylpyrimidin-5-yl)ethyl)-6-(2-(5-fluoropyrimidin-2-yl)cyclobutyl)-4-oxo-4,5-dihydro-1H-pyrazolo[3,4-d]pyrimidine-3-carbonitrile;
1-((S)-1-(2-cyclopropylpyrimidin-5-yl)ethyl)-6-((1R,2R)-2-(5-fluoropyrimidin-2-yl)cyclobutyl)-4-oxo-4,5-dihydro-1H-pyrazolo[3,4-d]pyrimidine-3-carbonitrile;
1-((S)-1-(2-cyclopropylpyrimidin-5-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile;
1-((R)-1-(2-cyclopropylpyrimidin-5-yl)ethyl)-6-((1R,2R)-2-(5-fluoropyrimidin-2-yl)cyclobutyl)-4-oxo-4,5-dihydro-1H-pyrazolo[3,4-d]pyrimidine-3-carbonitrile;
1-((R)-1-(2-cyclopropylpyrimidin-5-yl)ethyl)-6-((1S,2S)-2-(5-fluoropyrimidin-2-yl)cyclobutyl)-4-oxo-4,5-dihydro-1H-pyrazolo[3,4-d]pyrimidine-3-carbonitrile;
6-(2-(5-ethynylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;
6-((1R,2R)-2-(5-ethynylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;
6-((1S,2S)-2-(5-ethynylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;
6-((1R,2R)-2-(5-ethynylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;
6-((1S,2S)-2-(5-ethynylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;
6-(2-(5-fluoropyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;
6-((1R,2R)-2-(5-fluoropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;
6-((1S,2S)-2-(5-fluoropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;
6-((1R,2R)-2-(5-fluoropyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;
6-((1S,2S)-2-(5-fluoropyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;
6-(2-(5-fluoropyrimidin-2-yl)cyclobutyl)-4-oxo-1-(1-(tetrahydro-2H-pyran-4-yl)ethyl)-4,5-dihydro-1H-pyrazolo[3,4-d]pyrimidine-3-carbonitrile;
6-((1R,2R)-2-(5-fluoropyrimidin-2-yl)cyclobutyl)-4-oxo-1-((S)-1-(tetrahydro-2H-pyran-4-yl)ethyl)-4,5-dihydro-1H-pyrazolo[3,4-d]pyrimidine-3-carbonitrile;
6-((1S,2S)-2-(5-fluoropyrimidin-2-yl)cyclobutyl)-4-oxo-1-((S)-1-(tetrahydro-2H-pyran-4-yl)ethyl)-4,5-dihydro-1H-pyrazolo[3,4-d]pyrimidine-3-carbonitrile;
6-((1R,2R)-2-(5-fluoropyrimidin-2-yl)cyclobutyl)-4-oxo-1-((R)-1-(tetrahydro-2H-pyran-4-yl)ethyl)-4,5-dihydro-1H-pyrazolo[3,4-d]pyrimidine-3-carbonitrile;
6-((1S,2S)-2-(5-fluoropyrimidin-2-yl)cyclobutyl)-4-oxo-1-((R)-1-(tetrahydro-2H-pyran-4-yl)ethyl)-4,5-dihydro-1H-pyrazolo[3,4-d]pyrimidine-3-carbonitrile;
6-(1-methyl-2-(pyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;
6-((1R,2R)-1-methyl-2-(pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;
6-((1S,2S)-1-methyl-2-(pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;
6-((1R,2R)-1-methyl-2-(pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;
6-((1S,2S)-1-methyl-2-(pyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;
6-(2-(5-cyanopyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;
6-((1R,2R)-2-(5-cyanopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-cyanopyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-cyanopyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-cyanopyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-(2-(5-cyclopropylpyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-cyclopropylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-cyclopropylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-cyclopropylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-cyclopropylpyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

1-(1-(2-cyclopropylpyrimidin-5-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(2-cyclopropylpyrimidin-5-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(2-cyclopropylpyrimidin-5-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((R)-1-(2-cyclopropylpyrimidin-5-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((R)-1-(2-cyclopropylpyrimidin-5-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

6-(2-(5-methoxypyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-methoxypyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-methoxypyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-methoxypyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-methoxypyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

1-(1-(5-fluoropyridin-2-yl)ethyl)-4-oxo-6-(2-(pyrimidin-2-yl)cyclobutyl)-4,5-dihydro-1H-pyrazolo[3,4-d]pyrimidine-3-carbonitrile;

1-((S)-1-(5-fluoropyridin-2-yl)ethyl)-4-oxo-6-((1R,2R)-2-(pyrimidin-2-yl)cyclobutyl)-4,5-dihydro-1H-pyrazolo[3,4-d]pyrimidine-3-carbonitrile;

1-((S)-1-(5-fluoropyridin-2-yl)ethyl)-4-oxo-6-((1S,2S)-2-(pyrimidin-2-yl)cyclobutyl)-4,5-dihydro-1H-pyrazolo[3,4-d]pyrimidine-3-carbonitrile;

1-((S)-1-(5-fluoropyridin-2-yl)ethyl)-4-oxo-6-((1R,2S)-2-(pyrimidin-2-yl)cyclobutyl)-4,5-dihydro-1H-pyrazolo[3,4-d]pyrimidine-3-carbonitrile;

1-((S)-1-(5-fluoropyridin-2-yl)ethyl)-4-oxo-6-((1S,2R)-2-(pyrimidin-2-yl)cyclobutyl)-4,5-dihydro-1H-pyrazolo[3,4-d]pyrimidine-3-carbonitrile;

6-(2-(5-(difluoromethyl)pyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-(difluoromethyl)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-(difluoromethyl)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2S)-2-(5-(difluoromethyl)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2R)-2-(5-(difluoromethyl)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-(2-(5-chloropyrimidin-2-yl)cyclobutyl)-4-oxo-1-(1-(6-(trifluoromethyl)pyridin-3-yl)ethyl)-4,5-dihydro-1H-pyrazolo[3,4-d]pyrimidine-3-carbonitrile;

6-((1R,2R)-2-(5-chloropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-chloropyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(5-chloropyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(5-chloropyrimidin-2-yl)cyclobutyl)-4-oxo-1-((R)-1-(6-(trifluoromethyl)pyridin-3-yl)ethyl)-4,5-dihydro-1H-pyrazolo[3,4-d]pyrimidine-3-carbonitrile;

6-((1S,2S)-2-(4-methylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(4,6-dimethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1S,2S)-2-(4-(difluoromethyl)pyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;

6-((1S,2S)-2-(4,6-di-tert-butylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;

6-((1S,2S)-2-(4-cyclopropylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;

6-((1R,2R)-2-(4-(difluoromethyl)pyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile;

6-((1R,2R)-2-(4,6-bis(difluoromethyl)pyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile;

6-((1R,2R)-2-(4-methylpyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile;

6-((1R,2R)-2-(4,6-di-tert-butylpyrimidin-2-yl)cyclobutyl)-4-oxo-1-((R)-1-(6-(trifluoromethyl)-pyridin-3-yl)ethyl)-4,5-dihydro-1H-pyrazolo[3,4-d]pyrimidine-3-carbonitrile;

6-((1R,2R)-2-(4-methylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;

6-((1R,2R)-2-(4,6-dimethylpyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-(2-(4-(tert-butyl)pyrimidin-2-yl)cyclobutyl)-4-oxo-1-((S)-1-(6-(trifluoromethyl)pyridin-3-yl)ethyl)-4,5-dihydro-1H-pyrazolo[3,4-d]pyrimidine-3-carbonitrile;

6-((1R,2R)-2-(4,6-di-tert-butylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;

6-((1R,2R)-2-(4-(difluoromethyl)pyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile; and 6-((1R,2R)-2-(4-cyclopropylpyrimidin-2-yl)cyclobutyl)-4-oxo-1-((S)-1-(6-(trifluoromethyl)-pyridin-3-yl)ethyl)-4,5-dihydro-1H-pyrazolo[3,4-d]pyrimidine-3-carbonitrile;

or a pharmaceutically acceptable salt thereof.

* * * * *

UNITED STATES PATENT AND TRADEMARK OFFICE
CERTIFICATE OF CORRECTION

PATENT NO. : 10,934,294 B2
APPLICATION NO. : 16/001295
DATED : March 2, 2021
INVENTOR(S) : Ashok Arasappan et al.

It is certified that error appears in the above-identified patent and that said Letters Patent is hereby corrected as shown below:

In the Claims

Claim 1, Column 129, Line 27, should read:
(pyrimidin-2-yl) cyclobutyl)-4,5-dihydro-1H-pyra- Claim 1, Column 129, Line 33, should read:
clobutyl)-4-oxo-1-((S)-1-(6-(trifluoromethyl) pyri- Claim 1, Column 129, Line 41, should read:
((1S,2S)-2-(pyrimidin-2-yl) cyclobutyl)-4,5-dihydro- Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*